(12) United States Patent
Frost et al.

(10) Patent No.: US 6,384,051 B1
(45) Date of Patent: May 7, 2002

(54) METHOD OF TREATING OR INHIBITING COLONIC POLYPS

(75) Inventors: Philip Frost, Morris Township, NJ (US); Carolyn M. Discafani-Marro, Corlandt Manor, NY (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/805,070

(22) Filed: Mar. 13, 2001

Related U.S. Application Data

(60) Provisional application No. 60/304,198, filed on Mar. 13, 2000.

(51) Int. Cl.$^7$ .............................................. A61K 31/47
(52) U.S. Cl. ....................................... 514/313; 514/311
(58) Field of Search .................................. 514/313, 311

(56) References Cited

U.S. PATENT DOCUMENTS

| | | | | |
|---|---|---|---|---|
| 6,002,008 A | * | 12/1999 | Wissner et al. .............. | 546/160 |
| 6,015,814 A | * | 1/2000 | Barker ........................ | 514/259 |
| 6,127,374 A | * | 10/2000 | Bridges ...................... | 514/259 |

FOREIGN PATENT DOCUMENTS

| | | |
|---|---|---|
| WO | WO 9843960 A | 10/1998 |
| WO | WO 01 12227 A | 2/2001 |

\* cited by examiner

*Primary Examiner*—Zohreh Fay
*Assistant Examiner*—Brian-Yong Kwon
(74) *Attorney, Agent, or Firm*—John W. Hogan, Jr.

(57) ABSTRACT

This invention provides a method of treating or inhibiting colonic polyps which comprises providing a compound of formula 1

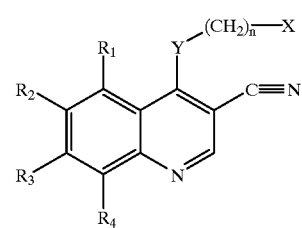

wherein:
$R_1$, $R_2$, $R_3$, $R_4$, X, Y, and n are as defined hereinbefore, or a pharmaceutically acceptable salt thereof.

21 Claims, No Drawings

METHOD OF TREATING OR INHIBITING COLONIC POLYPS

CROSS REFERENCE TO RELATED APPLICATIONS

This application claims the benefit of U.S. Provisional Application No. 60/304,198, which was converted from U.S. patent application Ser. No. 09/524,196, filed Mar. 13, 2000, pursuant to a petition filed Aug. 2, 2000 under 37 C.F.R. 1.53(c)(2).

This invention relates to the use of certain cyanoquinoline compounds in the treatment and inhibition of colonic polyps.

Colonic Polyps occur in both a familial pattern (Familial Adenomatous Polyps (FAP) and sporadically. FAP afflicts approximately 25,000 patients in the U.S.; while it is estimated that sporadic adenomatous polyps (SAP) occur in approximately 2 million people per year in the U.S. alone. All these patients are at risk for developing adenocarcinoma of the colon. In the case of FAP, that risk is virtually 100% and these patients usually undergo a colectomy at an early age. Patients with sporadic polyps are treated with polypectomy and require periodic colonoscopic examination because of their inherent risk of developing recurrent polyps. In fact, parents and siblings of these patients are also at increased risk for developing colorectal cancer.

The genetic basis for FAP has been linked to the presence of mutations in the APC gene. Similar APC mutations have been found in patients with sporadic polyps. Biochemically, the APC mutation occurs in conjunction with the increased expression of cyclooxygenase enzymes, particularly COX-2. These enzymes are essential for the production of prostenoids, (prostaglandin's; (PG's)) that mediate a number of functions in the bowel including motility, vascular tone, angiogenesis and mucosal protection. PG's are also purported to discourage apoptosis and this is proposed as an explanation for polyp formation.

The therapy of FAP and SAP has focused on inhibiting COX enzymes. Considerable evidence exists for the efficacy of COX inhibitors in reducing polyp formation. These COX inhibitors are predominantly NSAID's such as clinoril, sulindac, piroxicam and etodoloc, all of which appear to be equivalent in their action. A major problem with NSAID therapy has been the development of serious side effects including peptic ulceration, and cholestatic hepatitis and renal papillary necrosis. Long term therapy with NSAIDs for the treatment of polyps is therefore considered to be impractical. It has recently been proposed that the activation and overexpression of COX-2 in adenomatous polyps is due to activation of the epidermal growth factor receptor (EGFR). EGFR stimulation by one of it's ligands-amphiregulin (AR), induces the nuclear targeting of COX-2, release of PG's and subsequent mitogenesis, in polarized colonic epithelial cells. COX-2 inhibitors have been shown to prevent this series of events.

DESCRIPTION OF THE INVENTION

This invention provides a method of treating or inhibiting colonic polyps in a mammal in need thereof which comprises providing to said mammal an effective amount of a compound of formula 1:

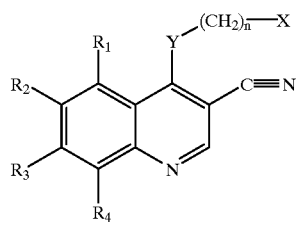

wherein:
X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

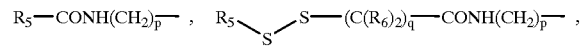

-continued

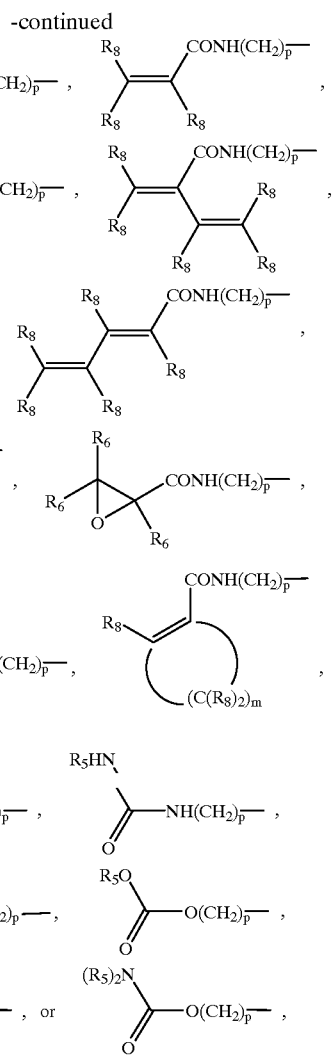

R$_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

R$_6$ is hydrogen, alkyl of 1–6 carbon atoms, or alkenyl of 2–6 carbon atoms;

R$_7$ is chloro or bromo;

R$_8$ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents R$_1$, R$_2$, R$_3$, or R$_4$ that are located on contiguous carbon atoms can together be the divalent radical —O—C(R$_8$)$_2$—O—;

or a pharmaceutically acceptable salt thereof with the proviso that when Y is —NH—, R$_1$, R$_2$, R$_3$, and R$_4$ are hydrogen, and n is O, X is not 2-methylphenyl.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains. The cycloalkyl portions of N-cycloalkyl-N-alkylaminoalkyl and N,N-dicycloalkylaminoalkyl substituents include both simple carbocycles as well as carbocycles containing alkyl substituents. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —CO$_2$H radical. Carboalkoxy of 2–7 carbon atoms is defined as a —CO$_2$R" radical, where R" is an alkyl radical of 1–6 carbon atoms. Carboalkyl is defined as a —COR" radical, where R" is an alkyl radical of 1–6 carbon atoms. Alkanoyloxy is defined as a —OCOR" radical, where R" is an alkyl radical of 1–6 carbon atoms. Alkanoyloxymethyl is defined as R"CO$_2$CH$_2$— radical, where R" is an alkyl radical of 1–6 carbon atoms. Alkoxymethyl is defined as R"OCH$_2$— radical, where R" is an alkyl radical of 1–6 carbon atoms. Alkylsulphinyl is defined as R"SO— radical, where R" is an alkyl radical of 1–6 carbon atoms. Alkylsulphonyl is defined as R"SO$_2$— radical, where R" is an alkyl radical of 1–6 carbon atoms. Alkylsulfonamido, alkenylsulfonamido, alkynylsulfonamido are defined as R"SO$_2$NH— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R" R'NCO— radical, where R" is an alkyl radical of 1–6 carbon atoms, R' is an alkyl radical of 1–6 carbon atoms and R', and R" may be the same or different. When X is substituted, it is preferred that it is mono-, di-, or tri-substituted, with monosubstituted being most preferred. It is preferred that of the substituents R$_1$, R$_2$, R$_3$, and R$_4$, at least one is hydrogen and it is most preferred that two or three be hydrogen. An azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A piperidino-N-alkyl substituent is a piperidine ring substituted on one of the nitrogen atoms with a straight or branch chain alkyl radical. A N-alkyl-piperidino-N-alkyl substituent is a piperidine ring substituted on one of the nitrogen atoms with a straight or branched chain alkyl group and on the other nitrogen atom with a straight or branch chain alkyl radical.

The compounds of this invention may contain an asymmetric carbon; in such cases, the compounds of this invention cover the racemate and the individual R and S entantiomers, and in the case were more than one asymmetric carbon exists, the individual diasteromers, their racemates and individual entantiomers.

As used in accordance with this invention, the term providing an effective amount means either directly administering such a compound of this invention, or administering a prodrug, derivative, or analog which will form an effective amount of the compound of this invention within the body.

The preparation of the compounds of this invention encompassed by Formula 5 is described below in Flowsheet A where Y and n are as described above and X' is cycloalkyl or phenyl optionally substituted with one or more substituents selected from the group consisting of hydrogen, halogeno, alkyl of 1–6 carbon atoms, alkenyl of 2–6 carbon atoms, alkynyl of 2–6 carbon atoms, halomethyl, alkoxy of 1–6 carbon atoms, alkylthio of 1–6 carbon atoms, trifluoromethyl, cyano, nitro, carboalkyl of 2–7 carbon atoms, phenoxy, phenyl, thiophenoxy, benzyl, dialkylamino of 2 to 12 carbon atoms. $R_1'$, $R_2'$, $R_3'$, and $R_4'$ are each, independently, hydrogen, halogeno, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, halomethyl, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, trifluoromethyl, cyano, nitro, carboxy, carboalkyl of 2–7 carbon atoms, phenoxy, phenyl, thiophenoxy, benzyl, alkoxyamino of 1–4 carbon atoms, dialkylamino of 2 to 12 carbon atom, N,N-dialkylaminoalkyl of 3–14 carbon atoms, phenylamino, benzylamino, N-alkylcarbamoyl of 1–6 carbon atoms, N,N-dialkylcarbamoyl of 2–12 carbon atoms. Any of the substituents $R_1$, $R_2$, $R_3$, or $R_4'$ that are located on contiguous carbon atoms can together be the divalent radical —O—C($R_8$)$_2$—O—. According to the sequence of reaction outlined in flowsheet A, a quinoline-3-carboxylic acid ester of Formula 2 is hydrolyzed with base to furnish a carboxylic acid of Formula 3. The carboxylic acid group of 3 is converted to an acyl imidazole by heating it with carbonyldiimidazole in an inert solvent such as dimethylformamide (DMF) followed by the addition of ammonia to give the amide 4. Dehydration of the amide functional group with a dehydrating agent such as trifluoroacetic anhydride in pyridine, phosphorous pentoxide in an inert solvent, or the like gives the 3-cyano quinolines, 5, of this invention. In those cases where any of the intermediates have an asymmetric carbon atom, they can be used as the racemate or as the individual R or S entantiomers in which case the compounds of this invention will be in the racemic or R and S optically active forms, respectively. The quinoline-3-carboxylic acid esters of Formula 2, the quinoline-3-carboxylic acids of Formula 3, and the quinoline-3-carboxylic amides of Formula 4 needed to prepare the compounds of this invention are either already known to the art or can be prepared by procedures known in the art as detailed in the following references: Sarges, Reinhard; Gallagher, Andrea; Chambers, Timothy J.; Yeh, Li An, *J. Med. Chem.*, 36, 2828 (1993); Savini, Luisa; Massarelli, Paola; Pellerano, Cesare; Bruni, Giancarlo, *Farmaco*, 48(6), 805 (1993); Ife, Robert J.; Brown, Thomas H.; Keeling, David J.; Leach, Colin, *J. Med. Chem.*, 35, 3413 (1992); Hanifin, J. William; Capuzzi, Rosemary; Cohen, Elliott, *J. Med. Chem.*, 12(5), 1096 (1969); Marecki, Paul E.; Bambury, Ronald E., *J. Pharm. Sci.*, 73(8), 1141 (1984); Pellerano, C.; Savini, L.; Massarelli, P.; Bruni, G.; Fiaschi, A. I., *Farmaco*, 45(3), 269, (1990); Marecki, Paul E.; Bambury, Ronald E., *J. Pharm. Sci.*, 73(8), 114 (1984); patent application WO 8908105; U.S. Pat. No. 4,343,804; U.S. Pat. No. 3,470,186.

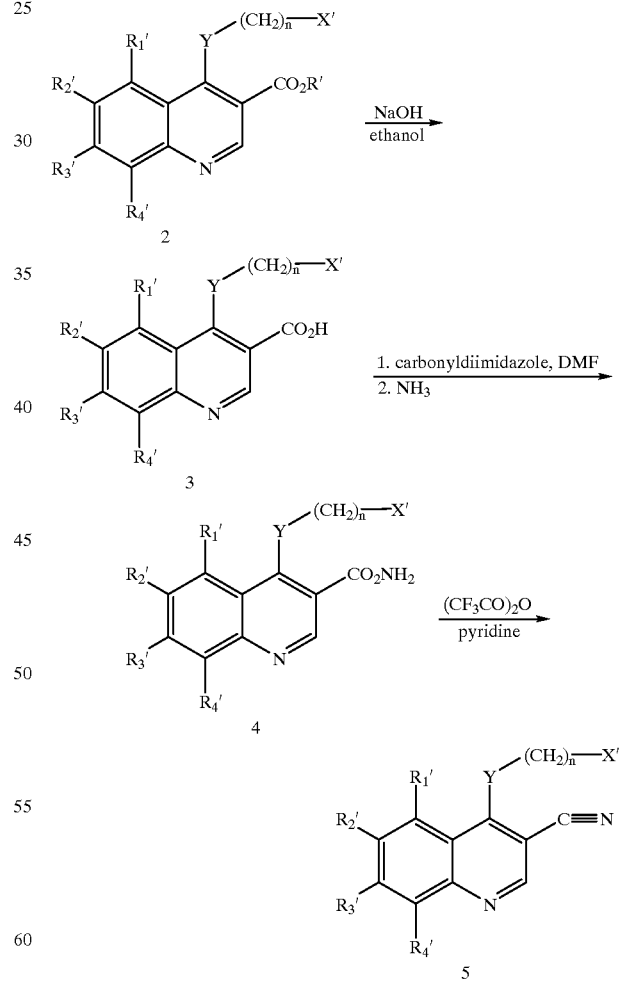

FLOWSHEET A

The preparation of the compounds of this invention encompassed by Formula 10 and Formula 11 are described below in Flowsheet B where Y, p, and n are as described above. X" is selected from the group consisting of cycloalkyl or phenyl optionally substituted with one or more substituents selected from the group consisting of hydrogen, halogeno, alkyl of 1–6 carbon atoms, alkenyl of 2–6 carbon atoms, alkynyl of 2–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino. Each $R_9$ is independently hydrogen, phenyl, or alkyl of 1–6 carbon atoms. The moieties $(R_{10})_k$ represent 1 to 3 substituents on the aromatic ring that can be the same or different and are selected independently from the group hydrogen, halogeno, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, halomethyl, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, trifluoromethyl, cyano, nitro, carboxy, carboalkyl of 2–7 carbon atoms, phenoxy, phenyl, thiophenoxy, benzyl, alkoxyamino of 1–4 carbon atoms, dialkylamino of 2 to 12 carbon atom, N,N-dialkylaminoalkyl of 3–14 carbon atoms, phenylamino, benzylamino, N-alkylcarbamoyl of 1–6 carbon atoms, N,N-dialkylcarbamoyl of 2–12 carbon atoms. $R_{11}$ is a radical and is selected from the group:

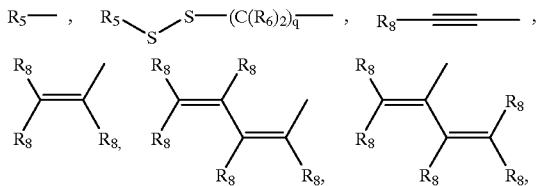

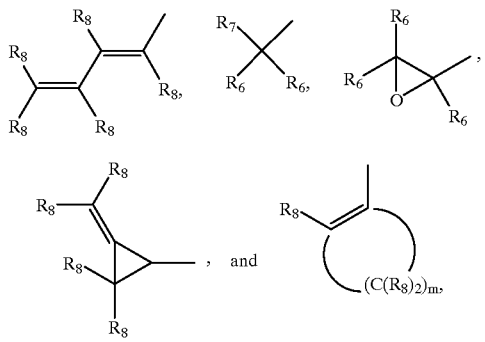

wherein q, $R_5$, $R_6$, $R_7$, and $R_5$ are as defined above. R''' is alkyl from 1 to 6 carbon atoms preferably isobutyl. According to the sequence of reactions outlined in Flowsheet B, acylation of 6 with either an acid chloride of Formula 8 or a mixed anhydride of Formula 9 (which is prepared from the corresponding carboxylic acid) in an inert solvent such as tetrahydrofuran (THF) in the presence of an organic base such as pyridine, triethylamine, or N-methyl morpholine gives the compounds of this invention represented by Formula 11. In those cases where 8 or 9 have an asymmetric carbon atom, they can be used as the racemate or as the individual R or S entantiomers in which case the compounds of this invention will be in the racemic or R and S optically active forms, respectively. Acylation of 6 with a cyclic anhydride of Formula 7 in an inert solvent such as tetrahydrofuran in the presence of a basic catalyst such as pyridine or triethylamine gives the compounds of the invention of Formula 10. The compounds of Formula 6 with p=0 can be prepared from the aromatic nitro substituted compounds by reducing the nitro group with a reducing agent such as iron and ammonium chloride in alcohol, sodium hydrosulfite in an aqueous mixture, or the like.

FLOWSHEET B

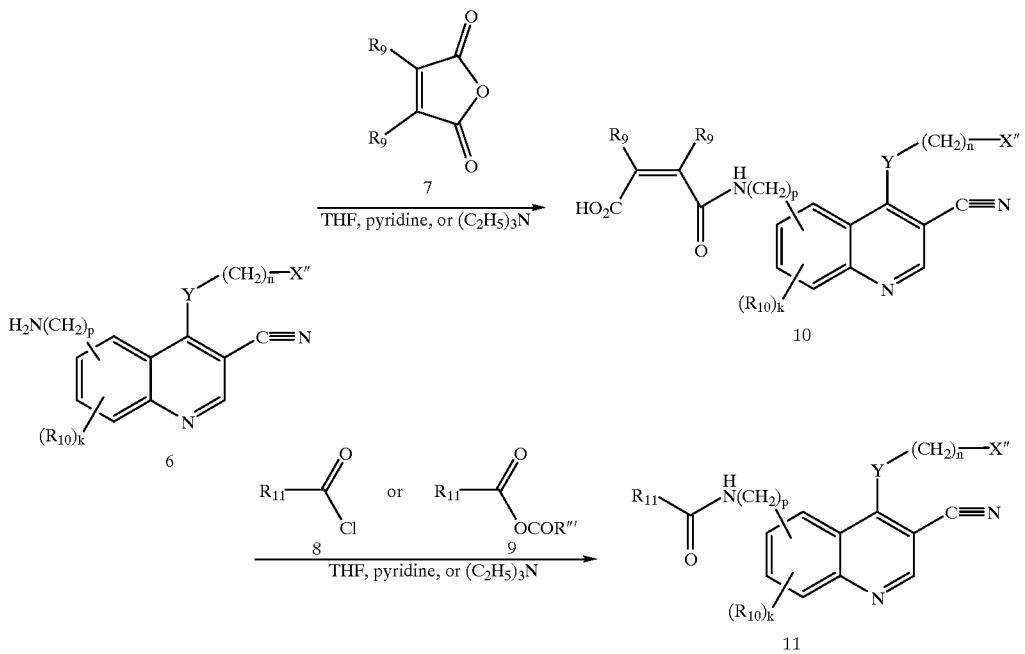

The preparation of the compounds of this invention encompassed by Formula 18 is described below in Flowsheet C where X, Y, n, $R_1'$, $R_2'$, $R_3'$, and $R_4'$ are as described above. The substituted aniline of Formula 12 is heated with or without a solvent with the reagent 13 to give intermediate 14 as a mixture of isomers. Thermolysis of 14 in a high boiling solvent such as diphenyl ether at 200–350° C. gives the 3-cyano quinolones of Formula 15; these intermediates may also exist in the 4-hydroxy quinoline tautomeric form. In those cases where $R_4'$ is a hydrogen atom, the intermediates 15 may be formed as a mixture of two regioisomers. These isomers can be separated by methods well known in the art including, but not limited to, fractional crystallization and chromatographic methods. The separated isomers can then be converted separately to the compounds of the invention. Alternatively, the isomers can be separated at a later stage of the synthesis. Heating compounds 15 with or without solvent with a chlorinating agent such as phosphorous oxychloride or phosphorous pentachloride gives the 4-chloro-3-cyano quinolines of Formula 16. Condensation of 16 with a nucleophilic amine, aniline, mercaptan, thiophenol, phenol, or alcohol reagent of Formula 17 gives the 3-cyano quinolines of this invention of Formula 18; this condensation can be accelerated by heating the reaction mixture or by using basic catalysts such as trialkylamines, sodium hydride in an inert solvent, sodium or potassium alkoxides in an alcohol solvents, and the like. In those cases where the substituents X, $R_1'$, $R_2'$, $R_3'$, and $R_4'$ may contribute an asymmetric carbon atom, the intermediates can be used as the racemate or as the individual R or S entantiomers in which case the compounds of this invention will be in the racemic or R and S optically active forms, respectively. In cases where the substituents X, $R_1'$, $R_2'$, $R_3'$, and $R_4'$ may contribute more than one asymmetric carbon atoms, diasteriomers may be present; these can be separated by methods well known in the art including, but not limited to, fractional crystallization and chromatographic methods.

FLOWSHEET C

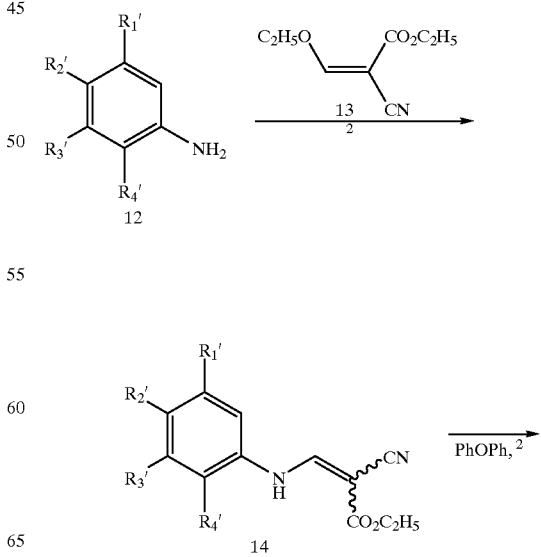

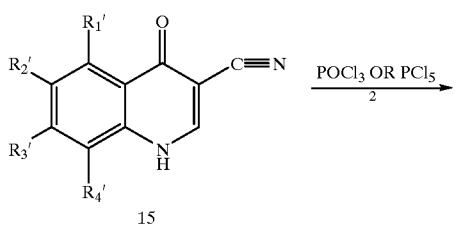

15

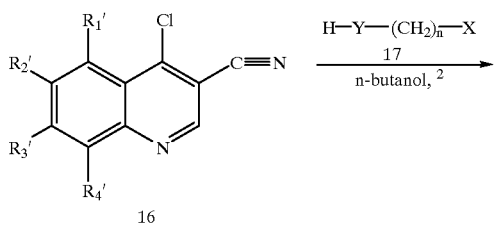

16

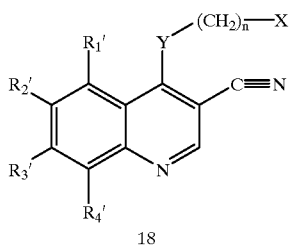

18

The preparation of intermediate 21 (identical to intermediate 15 of Flowsheet C) can also be prepared as describe below in Flowsheet D. Heating the substituted aniline of Formula 19 with dimethylformamide dimethyl acetal with or without a solvent gives intermediates for Formula 20. The reaction of 20 with one to ten equivalents of acetonitrile using a base such as sodium methoxide or the like in an inert solvent gives the 3-cyano quinolones, 21, or the 3-cyano-4-hydroxy quinoline tautomers thereof which can be converted to the compounds of this invention using the procedures outlined above in Flowsheet C.

FLOWSHEET D

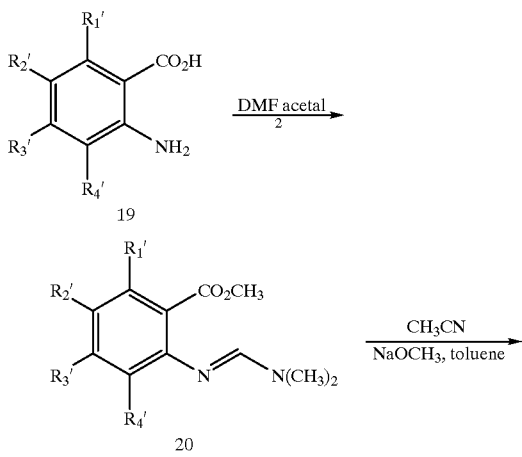

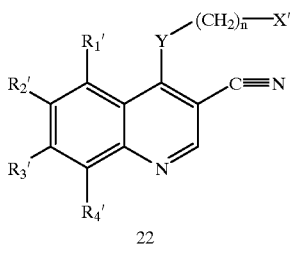

21

Formula 22 is given below wherein $R_1$, $R_2$, $R_3$, $R_4$, n, and X' are as defined above.

Where one or more of $R_1$, $R_2$, $R_3$, or $R_4$ of Formula 22 is a nitro group, it can be converted to the corresponding amino group by reduction using a reducing agent such as iron in acetic acid.

Where one or more of $R_1$, $R_2$, $R_3$, or $R_4$ of Formula 22 is an amino group, it can be converted to the corresponding dialkyamino group of 2 to 12 carbon atoms by alkylation with at least two equivalents of an alkyl halide of 1 to 6 carbon atoms by heating in an inert solvent.

Where one or more of $R_1$, $R_2$, $R_3$, or $R_4$ of Formula 22 is a methoxy group, it can be converted to the corresponding hydroxy group by reaction with a demethylating agent such as boron tribromide in an inert solvent or by heating with pyridinium chloride with or without solvent.

Where one or more of $R_1$, $R_2$, $R_3$, or $R_4$ of Formula 22 is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a basic catalyst such as triethylamine or pyridine. Alternatively, when one or more of $R_1$, $R_2$, $R_3$, or $R_4$ of Formula 22 is an amino group, it can be converted to the corresponding alkenylsulfonamido group by the reaction with a reagent $Cl—C(R'_6)_2—CHR'_6SO_2Cl$, wherein $R'_6$ is hydrogen or alkyl of 1–4 carbon atoms, in an inert solvent using an excess of an organic base such as triethylamine.

Where two of $R_1$, $R_2$, $R_3$, or $R_4$ of Formula 22 is are contiguous methoxy groups, the corresponding compound with contiguous hydroxy groups can be prepared by using a demethylating agent such as boron tribromide in an inert solvent or by heating with pyridinium chloride with or without solvent.

Where two of $R_1$, $R_2$, $R_3$, or $R_4$ of Formula 22 is are contiguous hydroxy groups, they can be converted to the compound where together the two contiguous $R_1$, $R_2$, $R_3$, or $R_4$ groups are the divalent radical $—O—C(R_8)_2—O—$ wherein $R_8$ is defined above by the reaction with a reagent, $J—C(R_8)_2—J$, wherein J is chloro, bromo, or iodo, and each J can be the same or different, using a base such as cesium carbonate or potassium carbonate in an inert solvent and heating as required.

Where one or more of $R_1$, $R_2$, $R_3$, or $R_4$ of Formula 22 is an amino group, it can be converted to the corresponding alkyamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof.

Where one or more of $R_1$, $R_2$, $R_3$, or $R_4$ of Formula 22 is hydroxy, it can be converted to the corresponding alkanoyloxy, group of 1–6 carbon atoms by reaction with an appropriate carboxylic acid chloride, anhydride, or mixed anhydride in a inert solvent using pyridine or a trialkylamine as a catalyst.

Where one or more of $R_1$, $R_2$, $R_3$, or $R_4$ of Formula 22 is hydroxy, it can be converted to the corresponding alkenoyloxy group of 1–6 carbon atoms by reaction with an appropriate carboxylic acid chloride, anhydride, or mixed anhydride in an inert solvent using pyridine or a trialkylamine as a catalyst.

Where one or more of $R_1$, $R_2$, $R_3$, or $R_4$ of Formula 22 is hydroxy, it can be converted to the corresponding alkynoyloxy group of 1–6 carbon atoms by reaction with an appropriate carboxylic acid chloride, anhydride, or mixed anhydride in a inert solvent using pyridine or a trialkylamine as a catalyst.

Where one or more of $R_1$, $R_2$, $R_3$, or $R_4$ of Formula 22 is carboxy or a carboalkoxy group of 2–7 carbon atoms, it can be converted to the corresponding hydroxymethyl group by reduction with an appropriate reducing agent such as borane, lithium borohydride, or lithium aluminum hydride in a inert solvent; the hydroxymethyl group, in turn, can be converted to the corresponding halomethyl group by reaction in an inert solvent with a halogenating reagent such as phosphorous tribromide to give a bromomethyl group, or phosphorous pentachloride to give a chloromethyl group. The hydroxymethyl group can be acylated with an appropriate acid chloride, anhydride, or mixed anhydride in an inert solvent using pyridine or a trialkylamine as a catalyst to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms.

Where one or more of $R_1$, $R_2$, $R_3$, or $R_4$ of Formula 22 is a halomethyl group, it can be converted to an alkoxymethyl group of 2–7 carbon atoms by displacing the halogen atom with a sodium alkoxide in an inert solvent.

Where one or more of $R_1$, $R_2$, $R_3$, or $R_4$ of Formula 22 is a halomethyl group, it can be converted to an aminomethyl group, N-alkylaminomethyl group of 2–7 carbon atoms or N,N-dialkylaminomethyl group of 3–14 carbon atoms by displacing the halogen atom with ammonia, a primary, or secondary amine, respectively, in an inert solvent.

Where one or more of $R_1$, $R_2$, $R_3$, or $R_4$ of Formula 22 is a $H_2N(CH_2)_p$— group, it can be converted to the corresponding groups:

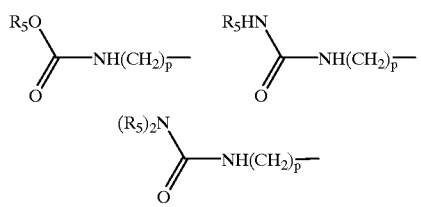

wherein $R_5$ and p are as defined above by reacting with phosgene in an inert solvent such as toluene in the presence of a base such as pyridine to give an isocyanate which, in turn, is treated with an excess of the alcohol $R_5$—OH or amines $R_5$—$NH_2$ or $(R_5)_2NH$, respectively.

Where one or more of $R_1$, $R_2$, $R_3$, or $R_4$ of Formula 22 is a HO—$(CH_2)_p$— group, it can be converted to the corresponding groups:

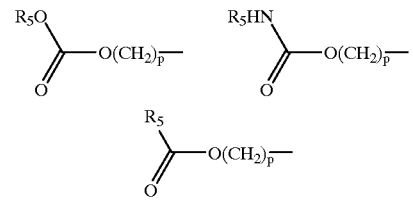

wherein $R_5$ and p are as defined above by the reaction, in an inert solvent using a basic catalyst such a pyridine, with an appropriate alkyl or phenyl chloroformate, $R_5$—OCOCl, alkyl or phenyl substituted isocyanate, $R_5$—N=C=O, or alkyl or phenyl substituted carboxylic acid chloride, $R_5$—COCl, respectively.

Where one or more of $R_1$, $R_2$, $R_3$, or $R_4$ of Formula 22 is a HO—$(CH_2)_p$— group, it can be converted to the corresponding group:

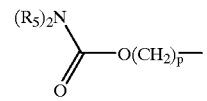

wherein $R_5$ and p are as defined above by the reaction, in an inert solvent using a basic catalyst such a pyridine, with a reagent $(R_5)_2NCOCl$.

The ability of the compounds of this invention to treat or inhibit colonic polyps was demonstrated in an in vivo standard pharmacological test procedure as described below. The compound of Example 399 was evaluated in this procedure, which emulates familial adenomatous polyps (FAP) in humans, as a representative compound of this invention. The min mouse used in this test procedure, currently the best available model for FAP, is a strain that has lost both copies of the APC gene. These animals develop multiple intestinal polyps (adenomas). The polyps that develop in min mice express EGFR and have activated COX-2. NSAID's such as sulindac and etodoloc can reduce (but not eradicate) intestinal polyp formulation in these animals indicating that COX-2 and the ultimate production of PG's is likely responsible for these effects. The following briefly describes the procedure used and the results obtained in this standard pharmacological test procedure.

The compound of Example 399 was blended with a standard murine chow and animals were given ad libitum access to the food for 60 days. Based on estimated food consumption, the compound of Example 399 was added at concentration commensurate with animals ingesting either 5 mg/kg/day or 150 mg/kg/day. At day 61, 10–15 animals in each treatment group+10–15 control (chow alone) animals corresponding to each treatment group were sacrificed and assessed for polyp number. The following table summarizes the results.

| Treatment Group | Mean # Polyps ± S.D. | P-Value vs Control |
|---|---|---|
| Group I | | |
| Control | 32.6 ± 19.1 | |
| 5 mg/kg/day Example 399 | 15.6 ± 6.0 | p < 0.01 |
| Group II | | |
| Control | 19.5 ± 14.1 | |
| 150 mg/kg/day Example 399 | 2.6 ± 1.6 | p < 0.001 |

These data demonstrate that the compounds of this invention effectively inhibit polyp formation in animals having mutations in their APC genes. Based on the results obtained in this standard pharmacological test procedure, the compounds of this invention are useful in treating or inhibiting the formation of colonic polyps.

The ability of an EGFR kinase inhibitor to treat or inhibit colonic polyps was demonstrated in an in vivo standard pharmacological test procedure as described below, using (4-dimethylamino-but-2-enoic acid [4-(3-chloro-4-fluoro-phenylamino)-3-cyano-7-ethoxy-quinolin-6-yl]-amide as a representative EGFR kinase inhibitor. The preparation and activity of (4-dimethylamino-but-2-enoic acid [4-(3-chloro-4-fluoro-phenylamino)- 3-cyano-7-ethoxy-quinolin-6-yl]-amide as an EGFR kinase inhibitor are described in U.S. Pat. No. 6,002,008. This potent EGFR Kinase inhibitor, (4-dimethylamino-but-2-enoic acid [4-(3-chloro-4-fluoro-phenylamino)-3-cyano-7-ethoxy-quinolin-6-yl]-amide, has proven to be effective in significantly reducing polyp numbers in mice.

The procedure described below emulates familial adenomatous polyps (FAP) in humans using the Min mouse (C57BL/6J-Min/+), which is a strain of mice that has a mutation in the APC (*Adenomatous Polyposis Coli*) Gene. These animals develop multiple intestinal polyps (adenomas) when raised on a high fat diet that ultimately lead to death by 120 days of age due to anemia and or intestinal blockage. The polyps that develop in Min mice express EGFR and have activated COX-2. The following briefly describes the procedure used and the results obtained in this standard pharmacological test procedure.

Test animals were divided into two treatment groups: Group I, control and Group II, (4-dimethylamino-but-2-enoic acid [4-(3-chloro-4-fluoro-phenylamino)-3-cyano-7-ethoxy-quinolin-6-yl]-amide. The test compound administered to Group II was blended with AIN-93G murine chow (Bioserve, Frenchtown, N.J.) and animals were given ad libitum access to the food, in quantities corresponding to the approximate daily dose of 20 mg/kg (4-dimethylamino-but-2-enoic acid [4-(3-chloro-4-fluoro-phenylamino)-3-cyano-7-ethoxy-quinolin-6-yl]-amide. The animals were treated for 60 days. The food was weighed once per week to determine consumption, and the animals also weighed weekly. On day 61, the animals were euthanized with $CO_2$ inhalation, and the entire intestinal tract from stomach to anus was removed. The intestinal tract was injected with Bouins fixative, and allowed to fix for several days. The intestinal tracts were then opened and the number of polyps counted. Statistical analysis was performed using the Student's t-Test; a p-value of $\leq 0.05$ is considered statistically significant.

The following table summarizes the results that were obtained.

| Treatment Group | Number of Polyps | P value |
|---|---|---|
| Group I | 19.5 ± 14.1 | |
| Group II | 2.6 ± 1.6 | <0.001 |

The results obtained in this standard pharmacological test procedure showed that treatment with (4-dimethylamino-but-2-enoic acid [4-(3-chloro-4-fluoro-phenylamino)-3-cyano-7-ethoxy-quinolin-6-yl]-amide alone reduced polyp numbers 87 percent when compared to the AIN-93G control diet alone.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, and antiestrogens such as tamoxifen.

The preparation of representative examples of the compounds of this invention is described below.

EXAMPLE 1

1,4-Dihydro-7-methoxy-4-oxo-3-quinolinecarbonitrile

A mixture of 30.2 g (245.2 mmol) of 3-methoxy aniline and 41.5 g (245.2 mmol) of ethyl(ethoxymethylene) cyanoacetate was heated in the absence of solvent to 140° C. for 30 minutes. To the resulting oil was added 1200 ml of Dowtherm. The solution was refluxed with stirring under nitrogen for 22 hours. The mixture was cooled to room temperature and solid was collected and washed with hexanes. The solid was recrystallized from acetic acid to give 17 g of 1,4-dihydro-7-methoxy-4-oxo-3-quinolinecarbonitrile: mass spectrum (electrospray, m/e): M+H 200.9.

EXAMPLE 2

4-Chloro-7-methoxy-3-quinolinecarbonitrile

A mixture of 4.0 g (20 mmol) of 1,4-dihydro-7-methoxy-4-oxo-3-quinolinecarbonitrile and 8.3 g (40 mmol) of phosphorous pentachloride was heated at 165° C. for 3 hours. The mixture was diluted with hexanes and the solid was collected. The solid was mixed with brine and dilute sodium hydroxide solution and extracted several times with a mixture of tetrahydrofuran and ethyl acetate. The solution was dried over magnesium sulfate and filtered through a pad of silica gel giving 3.7 g of 4-chloro-7-methoxy-3-quinolinecarbonitrile as a white solid: mass spectrum (electrospray, m/e): M+H 218.9.

EXAMPLE 3

4-[(3-Bromophenyl)amino]-7-methoxy-3-quinolinecarbonitrile

A solution of 2.97 g (13.6 mmol) of 4-chloro-7-methoxy-3-quinolinecarbonitrile and 4.67 g (27.2 mmol) of 3-bromo aniline in 76 ml of methoxyethanol was refluxed under nitrogen for 5 hours. The solution was cooled and diluted with ether. Solid was collected and washed with ether. The solid was stirred with a hot mixture of ethyl acetate and sodium bicarbonate solution. The organic layer was separated and dried over magnesium sulfate. Solvent was removed and the residue was recrystallized from a chloroform-ethyl acetate mixture giving 1.6 g of 4-[(3-bromophenyl)amino]-7-methoxy-3-quinolinecarbonitrile as a white solid: mass spectrum (electrospray, m/e): M+H 354.1, 356.1.

EXAMPLE 4

1,4-Dihydro-7-methoxy-6-nitro-4-oxo-3-quinolinecarbonitrile

To a suspension of 10 g (49.6 mmol) of 1,4-dihydro-7-methoxy-4-oxo-3-quinolinecarbonitrile in 160 ml of trifluoroacetic anhydride was added 6 g (74.9 mmol) of ammonium nitrate over a period of 3 hours. The mixture was stirred an additional two hours. Excess anhydride was removed at reduced pressure at 45° C. The residue was stirred with 500 ml of water. The solid was collected and washed with water. The solid was dissolved in 1000 ml of boiling acetic acid and the solution was treated with decolorizing charcoal. The mixture was filtered and concentrated to a volume of 300 ml. Cooling gave a solid which was collected giving 5.4 g of 1,4-dihydro-7-methoxy-6-nitro-4-oxo-3-quinolinecarbonitrile as a brown solid: mass spectrum (electrospray, m/e): M+H 246.

EXAMPLE 5

4-Chloro-7-methoxy-6-nitro-3-quinolinecarbonitrile

A mixture of 5.3 g (21.6 mmol) of 1,4-dihydro-7-methoxy-6-nitro-4-oxo-3-quinolinecarbonitrile and 9 g (43.2 mmol) of phosphorous pentachloride was heated at 165° C. for 2 hours. The mixture was diluted with hexanes and the solid was collected. The solid was dissolved in 700 ml ethyl acetate and washed with cold dilute sodium hydroxide solution. The solution was dried over magnesium sulfate and filtered through a pad of silica gel giving 5.2 g of 4-chloro-7-methoxy-6-nitro-3-quinolinecarbonitrile as a tan solid.

EXAMPLE 6

4-[(3-Bromophenyl)amino]-7-methoxy-6-nitro-3-quinolinecarbonitrile

A solution of 5.2 g (19.7 mmol) of 4-chloro-7-methoxy-6-nitro-3-quinolinecarbonitrile and 3.7 g (21.7 mmol) of 3-bromo aniline in 130 ml of methoxyethanol was refluxed under nitrogen for 4 hours. The reaction mixture was poured into dilute sodium bicarbonate solution. Solid was collected and washed with water and dried in air. The solid was chromatographed on silica gel eluting with chloroform-ethyl acetate 9:1. Solvent was removed from product fractions giving 1.2 g of 4-[(3-bromophenyl)amino]-7-methoxy-6-nitro-3-quinolinecarbonitrile as a yellow solid: mass spectrum (electrospray, m/e): M+H 399.0, 402.0.

EXAMPLE 7

6-Amino-4-[(3-bromophenyl)amino]-7-methoxy-3-quinolinecarbonitrile

A mixture of 2.05 g (5.1 mmol) of 4-[(3-bromophenyl)amino]-7-methoxy-6-nitro-3-quinolinecarbonitrile, 1.37 g (25.7 mmol) of ammonium chloride, and 0.86 g (15.4 mmol) of powdered iron was stirred at reflux in 26 ml water and 26 ml methanol for 2 hours. The mixture was diluted with ethyl acetate and the hot mixture was filtered. The organic layer was separated from the filtrate and dried over magnesium sulfate. The solvent was removed and the residue was chromatographed on silica gel eluting with mixtures of chloroform and ethyl acetate. Product fractions were combined to give 1.3 g of 6-amino-4-[(3-bromophenyl)amino]-7-methoxy -3-quinolinecarbonitrile as a yellow solid: mass spectrum (electrospray, m/e): M+H 369.1, 371.1.

EXAMPLE 8

N-[4-[(3-Bromophenyl)amino]-3-cyano-7-methoxy-6-quinolinyl]-2-butynamide

To a solution of 1.44 g (17.14 mmol) of 2-butynoic acid and 2.26 g (16.5 mmol) of isobutyl chloroformate in 30 ml of tetrahydrofuran at 0° C., with stirring, was added 3.1 g (3.4 mmol) of N-methyl morpholine. This solution of the mixed anhydride was added to a stirred solution of 1.13 g (3.06 mmol) of 6-amino-4-[(3-bromophenyl)amino]-7-methoxy-3-quinolinecarbonitrile in 30 ml tetrahydrofuran in three portions over a 24 hour period. The solvent was removed. The residue was stirred with dilute sodium bicarbonate solution. Solid was collected and washed with water and ether. This was recrystallized from 1-butanol. The resulting solid was taken up in hot tetrahydrofuran and filtered through silica gel. The filtrate was concentrated and diluted with hexanes to give 0.71 g of N-[4-[(3-bromophenyl)amino]-3-cyano-7-methoxy-6-quinolinyl]-2-butynamide as a yellow powder: mass spectrum (electrospray, m/e): M+H 437.1,438.1.

EXAMPLE 9

N-[4-[(3-Bromophenyl)amino]-3-cyano-7-methoxy-6-quinolinyl]-2-propenamide

To a solution of 1.5 g (4.06 mmol) of 6-Amino-4-[(3-bromophenyl)amino]-7-methoxy-3-quinolinecarbonitrile and 0.45 ml of N-methylmorpholine in 30 ml of tetrahydrofuran was added at 0° C., under nitrogen, with stirring, 0.42 g (4.7 mmol) of acryloyl chloride of a 15 minute period. After 1 hour at 0° C., the solution was diluted with 200 ml ethyl acetate. The mixture was washed with saturated sodium bicarbonate solution and then dried over magnesium sulfate. The solvent was removed. The residue was chromatographed on silica gel eluted with chloroform-ethyl acetate mixtures to give 0.5 g of the title compound as a light yellow solid powder: mass spectrum (electrospray, m/e): M+H 423.1,425.1

EXAMPLE 10

2-Cyano-3-(4-nitrophenylamino)acrylic Acid Ethyl Ester

4-Nitroaniline (60.0 g, 0.435 mol) and ethyl (ethoxymethylene) cyanoacetate (73.5 g, 0.435 mol) were mixed mechanically in a flask. The mixture was heated at 100° C. for 0.5 h after it had melted and resolidified. A 114 g portion of the crude product was recrystallized from dimethylformamide to give 44.2 g of yellow crystals; mp 227–228.5° C.

EXAMPLE 11

1,4-Dihydroquinoline-6-Nitro-4-oxo-3-carbonitrile

A slurry of 25.0 g (95.8 mmol) of 2-cyano-3-(4-nitrophenylamino)acrylic acid ethyl ester in 1.0 L of Dowtherm A was heated at 260° C. under $N_2$ for 12.5 h. The cooled reaction was poured into 1.5 L of hexane. The product was collected, washed with hexane and hot ethanol and dried in vacuo. There was obtained 18.7 g of brown solid. An analytical sample was obtained by recrystallization from dimethylformamide/ethanol: mass spectrum (electrospray, m/e): M+H 216.

EXAMPLE 12

4-Chloro-6-nitro-3-quinolinecarbonitrile

A mixture of 31.3 g (0.147 mol) of 6-nitro-4-oxo-1,4-dihydro-3-quinolinecarbonitrile and 160 mL of phosphorous oxychloride was refluxed for 5.5 h. The phosphorous oxychloride was removed in vacuo and the residue was poured over ice and neutralized with sodium bicarbonate. The product was collected, washed with water and dried in vacuo (500° C.). There was obtained 33.5 g of tan solid; solid: mass spectrum (electrospray, m/e): M+H 234.

EXAMPLE 13

4-[(3-Bromophenyl)amino]-6-nitro-3-quinolinecarbonitrile

A mixture of 17.0 g (73.1 mmol) of 4-chloro-6-nitro-3-quinolinecarbonitrile and 15.1 g (87.7 mmol) of 3-bromoaniline in 425 mL of ethanol was refluxed for 5 h. Saturated sodium bicarbonate was added and then all volatile material was removed in vacuo. The residue was slurried with hexane and the product was collected and washed with hexane. The crude product was washed with water and dried in vacuo (60° C.). There was obtained 22.5 g of yellow solid. An analytical sample was obtained by recrystallization from ethyl acetate; mp 258–259° C.

EXAMPLE 14

6-Amino-4-[(3-bromophenyl)amino]-3-quinolinecarbonitrile

A mixture of 4.00 g (10.8 mmol) of 4-[(3-bromophenyl)amino]-6-nitro-3-quinolinecarbonitrile and 12.2 g (54.2 mmol) of $SnCl_2$ dihydrate in 160 mL of ethanol was refluxed under $N_2$ for 1.3 h. After cooling to 250° C., ice water and sodium bicarbonate were added and the mixture was stirred for 2 h. Extraction with chloroform, treatment with Darco, drying (magnesium sulfate) and solvent removal gave 3.9 g of brown crystals: mass spectrum (electrospray, m/e): M+H 339.

EXAMPLE 15

N-[4-[(3-Bromophenyl)amino]-3-cyano-6-quinolinyl]-2-butynamide

Isobutyl chloroformate (0.788 g, 5.75 mmol) and N-methylmorpholine (0.581 g, 5.75 mmol) were added to an ice cold solution of 0.485 g (5.75 mmol) of 2-butynoic acid in 20 mL of tetrahydrofuran under $N_2$. After stirring for 10 min, a solution of 1.50 g (4.42 mmol) of 6-amino-4-[(3-bromophenyl)amino]-3-quinolinecarbonitrile in 10 mL of tetrahydrofuran was added and the mixture was stirred overnight at 25° C. A second equivalent of preformed mixed anhydride was then added. After 6 h, the reaction was poured into saturated sodium bicarbonate and brine. The product was collected and washed with hot ethyl acetate and ethanol and dried in vacuo to give 0.638 g of yellow solid; mp 283–285° C. (dec).

EXAMPLE 16

N-[4-[(3-Bromolphenol)amino]-3-cyano-6-quinolinyl]acetamide

Triethylamine (0.359 g, 3.55 mmol) and acetyl chloride (0.277 mg, 3.55 mmol) were added to an ice cold solution of 1.00 g (2.96 mmol) of 6-amino-4-[(3-bromophenyl)amino]-3-quinolinecarbonitrile in 8 mL of methylene chloride and 6 mL of tetrahydrofuran under $N_2$. After stirring overnight at 25° C., volatile material was removed, and the residue was slurried with water and collected. Recrystallization from ethanol gave 0.543 g of brown solid; mp 258–261° C. (dec).

EXAMPLE 17

N-[4-[(3-Bromophenyl)amino]-3-cyano-6-quinolinyl]butanamide

Triethylamine (0.359 g, 3.55 mmol) and butyryl chloride (0.380 g, 3.55 mmol) were added to an ice cold solution of 1.00 g (2.96 mmol) of 6-amino-4-[(3-bromophenyl)amino]-3-quinolinecarbonitrile in 12 mL of tetrahydrofuran under $N_2$. After stirring overnight at 25° C., volatile material was removed, and the residue was slurried with water and collected. The residue was washed with boiling methanol and dried in vacuo to give 0.773 g of brown powder; mp 276–277 ° C. (dec).

EXAMPLE 18

N-[4-[(3-Bromophenyl)amino]-3-cyano-6-quinolinyl]-2-propenamide

Triethylamine (0.359 g, 3.55 mmol) and acryloyl chloride (0.321 g, 3.55 mmol) were added to an ice cold solution of 1.00 g (2.96 mmol) of 6-amino-4-[(3-bromophenyl)amino]-3-quinolinecarbonitrile in 12 mL of tetrahydrofuran under $N_2$. After stirring overnight at 250° C., volatile material was removed and the residue was slurried with water and collected. Recrystallization from ethanol gave 0.580 g of brown solid: mass spectrum (electrospray, m/e): M+H 393, 395.

EXAMPLE 19

N-[4-[(3-Bromophenyl)amino]-3-cyano-6-quinolinyl]-2-chloroacetamide

Triethylamine (0.359 g, 3.55 mmol) and chloroacetyl chloride (0.402 g, 3.55 mmol) were added to an ice cold solution of 1.00 g (2.96 mmol) of 6-amino-4-[(3-bromophenyl)amino]-3-quinolinecarbonitrile in 12 mL of tetrahydrofuran under $N_2$. After stirring overnight at 25° C., volatile material was removed and the residue was slurried in water and collected. Recrystallization from methanol gave 0.540 g of tan solid: mass spectrum (electrospray, m/e): M+H 415,417.

EXAMPLE 20

4-[(3,4-Dibromophenyl)amino]-6-nitro-3-quinolinecarbonitrile

A mixture of 6.20 g (26.6 mmol)of 4-chloro-6-nitro-3-quinolinecarbonitrile and 8.00 g (31.9 mmol) of 3,4-dibromoaniline in 160 mL of ethanol was refluxed under $N_2$ for 5 h. Saturated sodium bicarbonate was added and volatile material was removed. The residue was slurried with hexane, collected, washed with hexane and water and dried. The insoluble material was repeatedly extracted with boiling ethyl acetate and the solution was then filtered through silica gel. The solvent was removed to give 3.80 g of green solid: mass spectrum (electrospray, m/e): M+H 449.

EXAMPLE 21

6-Amino-4-[(3,4-dibromophenyl)amino]-3-quinolinecarbonitrile

A mixture of 4.90 g (10.9 mmol) of 4-[(3,4-dibromophenyl)amino]-6-nitro-3-quinolinecarbonitrile and 12.4 g (54.7 mmol) of $SnCl_2$ dihydrate in 200 mL of ethanol was refluxed under $N_2$ for 1.5 h. After cooling to 25° C., the reaction was diluted with ice water, neutralized with sodium bicarbonate and stirred for 2 h. This solution was then extracted with chloroform, treated with Darco, dried (magnesium sulfate) and evaporated. After drying in vacuo (40° C.), there was obtained 1.25 g of brown solid: mass spectrum (electrospray, m/e): M+H 417, 419, 421.

EXAMPLE 22

N-[4-[(3,4-dibromophenyl)amino]-3-cyano-6-quinolinyl]-2-butynamide

Isobutyl chloroformate (0.984 g, 7.18 mmol) and N-methylmorpholine (0.725 g, 7.18 mmol) were added to an ice cold solution of 0.604 g (7.18 mmol) of 2-butynoic acid in 25 mL of tetrahydrofuran. After 10min, a solution of 1.20 g (2.87 mmol) of 6-amino-4-[(3,4-dibromophenyl)amino]-3-quinolinecarbonitrile in 12 mL of tetrahydrofuran was added dropwise. After stirring overnight at 25° C., volatile material was removed and the residue was slurried in water and filtered. The crude product was washed with boiling EtOAC and ethanol and dried in vacuo(50° C.) to give 0.651 g of brown solid: mass spectrum (electrospray, m/e): M+H 485.

EXAMPLE 23

6-Nitro-4-[(3-trifluoromethylphenyl)amino]-3-quinolinecarbonitrile

A mixture of 10.6 g (45.7 mmol) of 4-chloro-6-nitro-3-quinolinecarbonitrile and 8.82 g (54.8 mmol) of 3-(trifluoromethyl)aniline in 270 mL of ethanol was refluxed under $N_2$ for 5 h. The reaction was diluted with ethanol, neutralized with satd sodium bicarbonate and evaporated. The residue was slurried with hexane, collected, washed with hexane and water and dried in vacuo (60° C.) to give 10.9 g of yellow solid. A 2.00 g sample was recrystallized from ethanol to give 1.20 g of bright yellow solid; mp 260–261° C.

EXAMPLE 24

6-Amino-4-[(3-trifluoromethylphenyl)amino]-3-quinolinecarbonitrile

A slurry of 6.00 g (16.8 mmol) of 6-nitro-4-[(3-trifluoromethylphenyl)amino]-3-quinolinecarbonitrile and 18.9 g (83.3 mmol) of $SnCl_2$ dihydrate in 240 mL of ethanol was refluxed under $N_2$ for 1 h. After cooling to 25° C., the reaction was diluted with ice water, neutralized with sodium bicarbonate and stirred for 2 h. The product was extracted with chloroform, treated with Darco, dried (magnesium sulfate) and evaporated. The residue was filtered through silica gel (10% methanol in chloroform), evaporated and dried in vacuo (40° C.) to give 4.87 g of brown solid: mass spectrum (electrospray, m/e): M+H 329.

EXAMPLE 25

N-[4-[(3-Trifluoromethylphenyl)amino]-3-cyano-6-quinolinyl]-2-butynamide

Isobutyl chloroformate (1.56 g, 11.4 mmol) and N-methylmorpholine (1.15 g, 11.4 mmol) were added to an ice cold solution of 0.961 g (11.4 mmol) of 2-butynoic acid in 40 mL of tetrahydrofuran under $N_2$. After stirring for 10 min, a solution of 1.50 g (4.57 mmol) of 6-amino-4-[(3-trifluoromethylphenyl)amino]-3-quinolinecarbonitrile in 12 mL of tetrahydrofuran was added dropwise. After stirring at 25° C. overnight, volatile material was removed and the residue was slurried in water and filtered. The crude product was washed 3 times with small portions of hot ethyl acetate and then dried in vacuo (45° C.) to give 0.831 g of yellow solid: mass spectrum (electrospray, m/e): M+H 395.

EXAMPLE 26

3-Carbethoxy-4-hydroxy-6,7-dimethoxyquinoline

A mixture of 30.6 g of 4-aminoveratrole and 43.2 g of diethyl ethoxymethylenemalonate was heated at 100 for 2 h and at 165° C. for 0.75 h. The intermediate thus obtained was dissolved in 600 ml of diphenyl ether, and the resulting solution was heated at reflux temperature for 2 h, cooled, and diluted with hexane. The resulting solid was filtered, washed with hexane followed by ether, and dried to provide the title compound as a brown solid, mp 275–285° C.

EXAMPLE 27

3-Carbethoxy-4-chloro-6,7-dimethoxylquinoline

A mixture of 28.8 g of 3-carbethoxy-4-hydroxy-6,7-dimethoxyquinoline and 16.6 ml of phosphorous oxychloride was stirred at 110° C. for 30 min, cooled to 0° C., and treated with a mixture of ice and ammonium hydroxide. The resulting grey solid was filtered, washed with water and ether, and dried, mp 147–150° C.

EXAMPLE 28

4-[(3-Bromophenyl)amino]-6,7-dimethoxy-3-quinolinecarboxylic Acid, Ethyl Ester

A mixture of 14.8 g of 3-carbethoxy-4-chloro-6,7-dimethoxylquinoline, 9.46 g of 3-bromoaniline, 4.05 ml of pyridine, and 150 ml of ethanol was refluxed for 30 min, evaporated to remove ethanol, and partitioned with dichloromethane-aq sodium bicarbonate. The organic layer was washed with water, dried, and concentrated. The residue was recrystallized from ethanol to give a white solid, mp 155–158° C.

EXAMPLE 29

4-[(3-Bromophenyl)amino]-6,7-dimethoxy-3-quinolinecarboxylic Acid

A mixture of 13 g of 4-[(3-bromophenyl)amino]-3-quinolinecarboxylic acid, ethyl ester, 15 ml of 10 N sodium hydroxide, and 300 ml of ethanol was refluxed for 2 h. After evaporation of most ethanol, the residue was diluted with water and acidified with sodium dihydrogen phosphate to pH 7. The resulting white solid was filtered, washed with water, and dried, mp 282–285° C.

EXAMPLE 30

4-[(3-Bromophenyl)amino]-6,7-dimethoxy-3-quinolinecarboxamide

A mixture of 4.03 g of 4-[(3-bromophenyl)amino]-6,7-dimethoxy-3-quinolinecarboxylic acid, 3.24 g of carbonyldiimiazole, and 100 ml of dimethylformamide was heated at 55 for 30 m, cooled to 0° C., and saturated with ammonia gas. After warming to 25 the resulting solution was stirred for 45 m, heated at 50, and evaporated to remove dimethylformamide. The residue was stirred with water, and the resulting solid was filtered, washed with water, and dried. Recrystallization from acetone gave a grey solid, mp 239–242° C.

EXAMPLE 31

4-[(3-Bromophenyl)amino]-6,7-dimethoxy-3-quinolinecarbonitrile

To a stirred mixture of 3.02 g of 4-[(3-bromophenyl)amino]-6,7-dimethoxy-3-quinolinecarboxamide, 2.43 ml of pyridine, and 22.5 ml of dichloromethane at 0° C. was added 3.18 ml of trifluoroacetic anhydride during 3 min. The reaction mixture was warmed to 25° C., stirred for 60 min, and concentrated. The residue was dissolved in 38 ml of methanol. The resulting solution was treated with 15 ml of 5 N NaOH at 25° C. After 5 m the solution was acidified with carbon dioxide and evaporated free of methanol. The residue was partitioned with dichloromethane-water. The organic layer was washed with water, dried, and evaporated to give a white solid. Recrystallization from ethyl acetate-hexane gave mp 224–228° C.

EXAMPLE 32

Ethyl 2-cyano-3-(3,4-dimethoxyphenylamino) acrylate

A mixture of 7.66 g of 4-aminoveratrole, 8.49 g of ethyl ethoxymethylenecyanoacetate, and 20 ml of toluene was heated at 100° C. for 90 min. The toluene was evaporated to give a solid, mp 150–155° C.

EXAMPLE 33

1,4-Dihydro-6,7-dimethoxy-4-oxo-3-quinolinecarbonitrile

A mixture of 40 g of ethyl 2-cyano-3-(3,4-dimethoxyphenylamino)acrylate and 1.2 L of Dowtherm® A was refluxed for 10 h, cooled, and diluted with hexane. The resulting solid was filtered, washed with hexane followed by dichloromethane, and dried; mp 330–350° C. (dec).

EXAMPLE 34

4-Chloro-6,7-dimethoxy-3-quinolinecarbonitrile

A stirred mixture of 20 g of 1,4-dihydro-6,7-dimethoxy-4-oxo-3-quinolinecarbonitrile and 87 ml of phosphorous oxychloride was refluxed for 2 h, cooled, and evaporated free of volatile matter. The residue was stirred at 0° C. with dichloromethane-water as solid sodium carbonate was added until the aqueous layer was pH 8. The organic layer was separated, washed with water, dried and concentrated. Recrystallization from dichloromethane gave a solid, mp 220–223° C.

EXAMPLE 35

4-[(3-Fluorophenyl)amino]-6,7-dimethoxy-3-quinolinecarbonitrile

A mixture of 1.00 g of 4-chloro-6,7-dimethoxy-3-quinolinecarbonitrile, 0.89 g of 3-fluoroaniline, 0.32 ml of pyridine, and 12 ml of ethoxyethanol was stirred at reflux temperature for 4 h. The mixture was cooled and partitioned with dichloromethane and aqueous sodium bicarbonate. The organic layer was washed with water, dried and evaporated. The residue was recrystallized from ethyl acetate to give a solid, mp 226–230° C.

EXAMPLE 36

Methyl 2-(dimethylaminomethyleneamino)benzoate

To a stirred solution of 7.56 g of methyl anthranilate in 50 ml of dimethylformamide at 0° C. was added 5.6 ml of phosphorous oxychloride during 15 m. The mixture was heated at 55 for 45 m, cooled to 0, and diluted with dichloromethane. The mixture was basified at 0° C. by slow addition of cold 1N NaOH to pH 9. The dichloromethane layer was separated, washed with water, dried and concentrated to an oil.

EXAMPLE 37

1,4-Dihydro-4-oxo-3-quinolinecarbonitrile

A stirred mixture of 1.03 g of methyl 2-(dimethylaminomethyleneamino)benzoate, 0.54 g of sodium methoxide, 1.04 ml of acetonitrile, and 10 ml of toluene was refluxed for 18 h. The mixture was cooled, treated with water, and brought to pH 3 by addition of dilute HCl. The resulting solid was extracted with ethyl acetate. The extract was washed with water, dried and evaporated. The residue was recrystallized from ethanol to give a solid, mp 290–300° C.

EXAMPLE 38

4-(Cyclohexyamino)-6,7-dimethoxy-3-quinolinecarbonitrile

A solution of 1.24 g (5 mmole) of 4-chloro-6,7-dimethoxy-3-quinolinecarbonitrile, 1.14 ml (0.99 g; 10 mmole) of cyclohexylamine, and 0.4 ml (0.39 g) of pyridine in 10 ml of methyl celluosolve was refluxed in an oil bath at 148° C. for 3 hours. The reaction was poured into 25 ml of saturated aqueous sodium bicarbonate, and the resulting solid was filtered. This solid was dissolved in methylene chloride, and the solution was passed through Magnesol. Hexanes were added to the filtrate, and this solution was evaporated on a hot plate until crystals formed. Cooling gave 1.54 g of 4-(cyclohexyamino)-6,7-dimethoxy-3-quinolinecarbonitrile melting at 193–195° C.: mass spectrum (electrospray, m/e): M+H 312.1.

EXAMPLE 39

4-[(3-Bromophenyl)amino]-6,7-dihydroxy-3-quinolinecarbonitrile 5.11 g of of 4-[(3-bromophenyl)amino]-6,7-dimethoxy-3-quinolinecarbonitrile and 30.74 g of pyridine hydrochloride were intimately mixed and then heated under nitrogen at 207° C. for an hour. On cooling the reaction was treated with about 100 ml of water and the solid was filtered. This solid was digested with methyl cellusolve and washed with ether to give 3.00 g of 4-[(3-bromophenyl)amino]-6,7-dihydroxy-3-quinolinecarbonitrile: mass spectrum (electrospray, m/e): M+H 356, 358.

EXAMPLE 40

8-[(3-Bromophenyl)amino]-[1,3]-dioxolo[4,5-g]quinoline-7-carbonitrile

A mixture of 2.17 g (6.09 mmole) of 4-[(3-bromophenyl)amino]-6,7-dihydroxy-3-quinolinecarbonitrile, 0.59ml (1.18 g; 9.14 mmole) of bromochloromethane and 2.98 g (9.14 mmole) of cesium carbonate in 20 ml of N,N-dimethylformamide was heated and stirred for 2 hours in an oil bath at 111° C. The reaction was poured into 75 ml of water and extracted with four 50 ml portions of methylene chloride. The combined methylene chloride extracts were washed with several portions of water. This solution was taken to an oil in vacuo and this was dissolved in ethyl acetate. This solution was washed repeatedly with water, then with brine. The solution was dried over anhydrous magnesium sulfate, and taken to a solid in vacuo to give 0.95 g of 8-[(3-bromophenyl)amino]-[1,3]-dioxolo[4,5-g]quinoline-7-carbonitrile, m.p. 201–205° C.: mass spectrum (electrospray, m/e): M+H 368.1, 370.1.

EXAMPLE 41

4-[(3-Chlorophenyl)amino]-6,7-dimethoxy-3-quinolinecarbonitrile

A mixture of 0.5 g of 4-chloro-6,7-dimethoxy-3-quinolinecarbonitrile, 0.51 g of 3-chloroaniline, 0.16 ml of pyridine, and 6 ml of ethoxyethanol was stirred under nitrogen, at reflux temperature for 6 h. The mixture was cooled and partitioned with dichloromethane and aqueous sodium bicarbonate. The organic layer was washed with water, dried and evaporated. The residue was recrystallized from ethyl acetate-hexanes to give 0.37 g of 4-[(3-chlorophenyl)amino]-6,7-dimethoxy-3-quinolinecarbonitrile as a solid, mp 214–217° C.

EXAMPLE 42

4-[(3-Trifluoromethylphenyl)amino]-6,7-dimethoxy-3-quinolinecarbonitrile

A mixture of 1.24 g of 4-chloro-6,7-dimethoxy-3-quinolinecarbonitrile, 1.61 g of 3-trifluoromethylaniline, 0.4 ml of pyridine, and 15 ml of ethoxyethanol was stirred, under nitrogen, at reflux temperature for 5 h. The mixture was cooled and partitioned with dichloromethane and aqueous sodium bicarbonate. The organic layer was washed with water, dried and evaporated. The residue was recrystallized from ethyl acetate-hexanes to give 1.34 g of 4-[(3-trifluoromethylphenyl)amino]-6,7-dimethoxy-3-quinolinecarbonitrile as a solid, mp 190–193° C.

EXAMPLE 43

4-[(3,4-Dimethoxyphenyl)amino]-6,7-dimethoxy-3-quinolinecarbonitrile

A mixture of 1.0 g of 4-chloro-6,7-dimethoxy-3-quinolinecarbonitrile, 1.22 g of 3,4-dimethoxyaniline, 0.32 ml of pyridine, and 12 ml of ethoxyethanol was stirred, under nitrogen, at reflux temperature for 5 h. The mixture was cooled and partitioned with dichloromethane and aqueous sodium bicarbonate. The organic layer was washed with water, dried and evaporated. The residue was recrystallized from ethyl acetate to give 0.96 g of 4-[(3,4-dimethoxyphenyl)amino]-6,7-dimethoxy-3-quinolinecarbonitrile as a solid, mp 230–240° C.

EXAMPLE 44

4-[(Methylphenyl)amino]-6,7-dimethoxy-3-quinolinecarbonitrile

A mixture of 0.86 g of 4-chloro-6,7-dimethoxy-3-quinolinecarbonitrile, 0.86 g of N-methylaniline, 0.32 ml of pyridine, and 12 ml of ethoxyethanol was stirred, under nitrogen, at reflux temperature for 24 h. The mixture was cooled and partitioned with dichloromethane and aqueous sodium bicarbonate. The organic layer was washed with water, dried and evaporated. The residue was recrystallized from ethyl acetate-hexanes to give 0.54 g of 4-[(methylphenyl)amino]-6,7-dimethoxy-3-quinolinecarbonitrile as a solid, mp 137–141° C.

EXAMPLE 45

4-[(3-Cyanophenyl)amino]-6,7-dimethoxy-3-quinolinecarbonitrile

A mixture of 0.5 g of 4-chloro-6,7-dimethoxy-3-quinolinecarbonitrile, 0.47 g of 3-aminobenzonitrile, 0.16 ml of pyridine, and 12 ml of ethoxyethanol was stirred, under nitrogen, at reflux temperature for 22 h. The mixture was cooled and partitioned with dichloromethane and aqueous sodium bicarbonate. The organic layer was washed with water, dried and evaporated. The residue was recrystallized from ethyl acetate-hexanes to give 0.59 g of 4-[(3-cyanophenyl)amino]-6,7-dimethoxy-3-quinolinecarbonitrile as a solid, mp 285–288° C.

EXAMPLE 46

4-[(4-Fluorophenyl)amino]-6,7-dimethoxy-3-quinolinecarbonitrile

A mixture of 0.5 g of 4-chloro-6,7-dimethoxy-3-quinolinecarbonitrile, 0.44 g of 4-fluoroaniline, 0.16 ml of pyridine, and 6 ml of ethoxyethanol was stirred, under nitrogen, at reflux temperature for 4 h. The mixture was cooled and partitioned with dichloromethane and aqueous sodium bicarbonate. The organic layer was washed with water, dried and evaporated. The residue was recrystallized from ethyl acetate to give 0.59 g of 4-[(4-fluorophenyl)amino]-6,7-dimethoxy-3-quinolinecarbonitrile as a solid, mp 282–285° C.

EXAMPLE 47

4-[(3-Bromophenyl)amino]-6,7-diethoxy-3-quinolinecarbonitrile

A mixture of 0.36 g of 4-[(3-bromophenyl)amino]-6,7-dihydroxy-3-quinolinecarbonitrile, 0.32 ml of ethyl iodide and 0.55 g of potassium carbonate in 4 ml of dimethylsulfoxide was stirred for 3 hours in an oil bath with heating. Most of the solvent was removed at reduced pressure. The mixture was mixed with ethyl acetate and water. The organic layer was washed with water and dried over magnesium sulfate. Solvent was removed to give 0.23 g of 4-[(3-bromophenyl)amino]-6,7-diethoxy-3-quinolinecarbonitrile which after recrystallization from ethyl acetate gave mp=173–175° C.

EXAMPLE 48

4-[(3-(hydroxymethyl)phenyl)amino]-6,7-dimethoxy-3-quinolinecarbonitrile

A mixture of 1.0 g of 4-chloro-6,7-dimethoxy-3-quinolinecarbonitrile, 0.98 g of 3-aminobenzyl alcohol, 0.32 ml of pyridine, and 12 ml of ethoxyethanol was stirred, under nitrogen, at reflux temperature for 3 h. The mixture was cooled and partitioned with dichloromethane and aqueous sodium bicarbonate. The organic layer was washed with water, dried and evaporated. The residue was washed with hot methanol to give 1.16 g of 4-[(3-(hydroxymethyl)phenyl)amino]-6,7-dimethoxy-3-quinolinecarbonitrile as a solid, mp 250–255° C.

EXAMPLE 49

4-(3-Bromophenoxy)-6,7-dimethoxy-3-quinolinecarbonitrile

A mixture of 0.16 g of 88% KOH and 1.73 g of 3-bromophenol at 50° C. was treated with 0.50 g of 4-chloro-6,7-dimethoxy-3-quinolinecarbonitrile. The resulting mixture was heated to 170° C. during 30 min, cooled, and treated at 0° C. with 40 ml of 0.1N NaOH. The solid which resulted was filtered, washed with water, and dissolved in methylene chloride. The solution was washed with 0.5 N NaOH and water, dried, and concentrated. The resulting solid was recrystallized from methylene chloride-hexane to give 4-(3-bromophenoxy)-6,7-dimethoxy-3-quinolinecarbonitrile as a white solid, mp 187–190° C.

EXAMPLE 50

4-[(4-Bromophenyl)sulfanyl]-6,7-dimethoxy-3-quinolinecarbonitrile

To 1.89 g of 4-bromothiophenol at 25 under argon was added 0.16 g of 88% KOH. The resulting mixture was heated at 85° C. for 15 minutes, treated with 0.50 g of 4-chloro-6,7-dimethoxy-3-quinolinecarbonitrile, and heated at 140° C. for 1 hour and 160° C. for 15 minutes. The mixture was cooled and stirred at 0° C. with 40 ml of 0.1 N NaOH. The resulting solid was filtered, washed with water, and dissolved in methylene chloride. The solution was washed with 0.2 N NaOH and water, dried, and concentrated. The residue which resulted was recrystallized from ethyl acetate to give 4-[(3-bromophenyl)sulfanyl]-6,7-dimethoxy-3-quinolinecarbonitrile as a an off-white solid, mp 173–175° C.

EXAMPLE 51

N-[4-[(3-Bromophenyl)amino]-3-cyano-6-quinolinyl]-3(E)-chloro-2-propenamide and

EXAMPLE 52

N-[4-[(3-Bromophenyl)amino]-3-cyano-6-quinolinyl]-3(Z)-chloro-2-propenamide

A mixture of 3 g (28.2 mmol) of cis-3-chloro acrylic acid and 3.3 ml (37.5 mmol) of oxalyl chloride in 30 ml of methylene chloride containing one drop of dimethylformamide was stirred for 2.5 hours. The solvent was removed to give the acid chloride as a mixture of cis and trans isomers.

To a solution of 0.5 g (1.5 mmol) of 6-amino-4-[(3-bromophenyl)amino]-3-quinolinecarbonitrile and 0.24 g (1;8 mmol) of N,N-diisopropylethylamine in 5 ml tetrahydrofuran was added at 0° C., under nitrogen, with stirring, 0.21 g (1.7 mmol) of 3-chloro acryloyl chloride isomer mixture over a 4 minute period. After 40 min at 0° C., the solution was diluted with ether. The solid was collected and dissolved in a mixture of tetrahydrofuran and ethyl acetate. The mixture was washed with brine and then dried over magnesium sulfate. The solvent was removed. The residue was chromatographed on silica gel eluted with chloroform-ethyl acetate. Two products were obtained. The less polar product is N-[4-[(3-bromophenyl)amino]-3-cyano-6-quinolinyl]-3(E)-chloro-2-propenamide: mass spectrum (electrospray, m/e): M+H 424.9, 427.0. The more polar product is N-[4-[(3-bromophenyl)amino]-3-cyano-6-quinolinyl]-3(Z)-chloro-2-propenamide: mass spectrum (electrospray, m/e): M+H 425.0, 427.0.

EXAMPLE 53

N-[4-[(3-Bromophenyl)amino]-3-cyano-6-quinolinyl]-2-methyl-2-propenamide

To a solution of 0.5 g (1.48 mmol) of 6-amino-4-[(3-bromophenyl)amino]-3-quinolinecarbonitrile and 0.194 g (1.92 mmol) of triethylamine in 6 ml tetrahydrofuran was added at 0° C., under nitrogen, with stirring, 0.21 g (1.92 mmol) of 2-methyl acryloyl chloride over a 10 minute period. The solution was stirred at room temperature overnight. The mixture was poured into water. The solid was collected and air dried. The solid was washed with boiling ethyl acetate and air dried giving 0.32 g of N-[4-[(3-bromophenyl)amino]-3-cyano-6-quinolinyl]-2-methyl-2-propenamide: mass spectrum (electrospray, m/e): M+H 407, 409.

EXAMPLE 54

N-[4-[(3,4-Dibromophenyl)amino]-3-cyano-6-quinolinyl]-2-propenamide

To a solution of 0.75 g (1.79 mmol) of 6-amino-4-[(3,4-dibromophenyl)amino]-3-quinolinecarbonitrile and 0.22 g (2.15 mmol) of triethylamine in 10 mL of tetrahydrofuran was added dropwise 0.195 g (2.15 mmol) of acryloyl chloride. After stirring overnight at 25° C., volatile material was removed and the residue was slurried in water and solid was collected. The crude product was washed with boiling ethyl acetate dried in vacuo (50° C.) to give 0.609 g of brown solid: high resolution mass spectrum (m/e): 470.9457.

EXAMPLE 55

N-[4-[(5-bromo-3-pyridinyl)amino]-6,7-dimethoxy-3-quinolinecarbonitrile

A mixture of 249 mg (1 mmole) of 3-cyano-4-chloro-6,7-dimethoxy quinoline, 346 mg (2 mmoles) of 3-amino-5-bromo pyridine and 20 mg (about 0.1 mmole) of p-toluenesulfonic acid monohydrate in 5 ml of 2-methoxy ethanol was stirred and refluxed in an oil bath at 153° C. for 7 hours. On cooling overnight to room temperature, the solid was filtered and washed with ethanol, then with ether to give 287 mg (74.5%) of N-[4-[(5-bromo-3-pyridinyl)amino]-6,7-dimethoxy-3-quinolinecarbonitrile, which melted at 272–275° C. mass spectrum (electrospray, m/e) M+H= 384.9, 386.8.

EXAMPLE 56

4-[(3-Bromophenyl)amino]-6,7-bis(methoxymethoxy)-3-quinolinecarbonitrile

A mixture of 0.36 g of 4-[(3-bromophenyl)amino]-6,7-dihydroxy-3-quinolinecarbonitrile, 0.30 ml of 2-chloromethyl methyl ether and 0.55 g of potassium carbonate in 4 ml of dimethylformamide was stirred for 6 hours at 0° C. Most of the solvent was removed at reduced pressure. The mixture was mixed with ethyl acetate and water and the pH was adjusted to 8 with dilute hydrochloric acid. The organic layer was washed with water and dried over magnesium sulfate. Solvent was removed to give 4-[(3-bromophenyl)amino]-6,7-bis(methoxymethoxy)-3-quinolinecarbonitrile which was purified by column chromatography on silica gel.:mass spectrum (electrospray, m/e): M+H 356, 358.

EXAMPLE 57

N-[4-[(3-Bromophenyl)amino]-3-cyano-6-quinolinyl]-4-hydroxy-2-butynamide

Isobutyl chloroformate (0.214 g, 1.57 mmol) and N-methylmorpholine (0.190 g, 1.88 mmol) were added to an ice cold solution of 0.336 g (1.57 mmol) of 4-(tert-butyl-dimethyl-silanyloxy)-2-butynoic acid in 15 mL of tetrahydrofuran under $N_2$. After stirring for 30 min, it was transferred to an additional funnel plugged with a glass wool and added dropwise to a solution of 0.4 g (1.18 mmol) of 6-amino-4-[(3-bromophenyl)amino]-3-quinolinecarbonitrile in 3 mL of tetrahydrofuran and 1.5 ml of pyridine. The mixture was stirred at 25° C. for 1 h. The reaction solution was poured into ethyl acetate and washed with saturated sodium bicarbonate and brine. The product was collected and purified by flash column chromatography (60% ethyl acetate in hexane) to give 0.220 g of N-[4-[(3-Bromophenyl)amino]-3-cyano-6-quinolinyl]-4-(tert-butyl-dimethyl-silanyloxy)-2-butynamide as a yellow solid (35%); ESMS m/z 535.1 (M+H+); mp ° C. (dec). N-[4-[(3-Bromophenyl)amino]-3-cyano-6-quinolinyl]-4-(tert-butyl-dimethylsilanyloxy)-2-butynamide (0.120 g, 0.224 mmol) was dissolved in a 25 ml solution (acetic acid:tetrahydrofuran:water=3:1:1) and stirred overnight at 25° C. The reaction was poured into ethyl acetate and washed with saturated sodium bicarbonate and brine. The product was collected, washed with ethyl acetate, and dried in vacuo to give 0.085 g of yellow solid (90%); ESMS m/z 421.2 (M+H$^+$); mp 253–254° C. (dec).

EXAMPLE 58

N-[4-[(3-Bromophenyl)amino]-3-cyano-6-quinolinyl]-4-morpholino-2-butynamide

Isobutyl chloroformate (0.161 g, 1.18 mmol) and N-methylmorpholine (0.150 g, 1.48 mmol) were added to an ice cold solution of 0.250 g (1.48 mmol) of 4-morpholino-2-butynoic acid in 10 mL of tetrahydrofuran under $N_2$. After stirring for 30 min, a solution of 0.250 g (0.74 mmol) of 6-amino-4-[(3-bromophenyl)amino]-3-quinolinecarbonitrile in 8 mL of pyridine was added and the mixture was stirred at 0° C. for 2 h. The reaction was quenched with ice water and then poured into saturated sodium bicarbonate and brine. The product was collected, washed with ethyl acetate, and dried in vacuo to give 0.096 g (27%) of yellow solid; ESMS m/z 490.1 (M+H$^+$); mp 112–115° C.

EXAMPLE 59

N-[4-[(3-Bromophenyl)amino]-3-cyano-6-quinolinyl]-4-dimethylamino-2-butynamide Isobutyl chloroformate (0.260 g, 1.91 mmol) and N-methylmorpholine (0.594 g, 5.88 mmol) were added to an ice cold solution of 0.370 g (2.94 mmol) of 4-dimethylamino-2-butynoic acid in 50 mL of tetrahydrofuran under $N_2$. After stirring for 30 min, a solution of 0.500 g (01.47 mmol) of 6-amino-4-[(3-bromophenyl)amino]-3-quinolinecarbonitrile in 10 mL of pyridine was added and the mixture was stirred at 0° C. for 2 h. The reaction was quenched with ice water, and then poured into saturated sodium bicarbonate and brine. The product was collected, washed with ethyl acetate, and dried in vacuo to give 0.144 g (21%) of yellow solid; ESMS m/z 448.0 (M+H$^+$); mp 114–118° C.

EXAMPLE 60

N-[4-[(3-Bromophenyl)amino]-3-cyano-6-quinolinyl]-4-methoxy-2-butynamide

Isobutyl chloroformate (0.410 g, 3.0 mmol) and N-methylmorpholine (0.910 g, 9.0 mmol) were added to an ice cold solution of 0.680 g (6.0 mmol) of 4-methoxy-2-butynoic acid in 20 mL of tetrahydrofuran under $N_2$. After stirring for 30 min, a solution of 0.500 g (01.47 mmol) of 6-amino-4-[(3-bromophenyl)amino]-3-quinolinecarbonitrile in 10 mL of pyridine was added and the mixture was stirred at 0° C. for 2 h. The reaction was quenched with ice water, and then poured into saturated sodium bicarbonate and brine. The product was collected, washed with ethyl acetate, and dried in vacuo to give 0.200 g (35%) of yellow solid; ESMS m/z 435.1 (M+H$^+$); mp 198–202° C. (dec).

EXAMPLE 61

4-(3-Bromophenylmethylamino)-6,7-diethoxy-3-quinolinecarbonitrile

A stirred mixture of 4-chloro-6,7-diethoxy-3-quinolinecarbonitrile (0.69 g, 2.5 mmol), 3-bromobenzylamine (0.78 g, 3.5 mmol), diisopropylethyl amine (1.05 ml, 6.0 mmol), and 7.5 ml of ethoxyethanol was refluxed for 4 h, cooled, and stirred with a mixture of hexane and water containing 0.4 g of potassium carbonate for 3 h. The resulting solid was filtered, washed with water, and dried. Recrystallization from acetone-hexane gave 0.73 g of off-white solid, mp 156–159° C.

EXAMPLE 62

4-(3-Phenylmethylamino)-6,7-diethoxy-3-quinolinecarbonitrile

In the manner of Example 61 reaction of 4-chloro-6,7-diethoxy-3-quinolinecarbonitrile with benzylamine gave the title compound as an off-white solid, mp 150–153° C.

EXAMPLE 63

4-(3,4-Dimethoxyphenylmethylamino)-6,7-diethoxy-3-quinolinecarbonitrile

In the manner of Example 61 reaction of 4-chloro-6,7-diethoxy-3-quinolinecarbonitrile with 3,4-dimethoxybenzylamine gave the title compound as a tan solid, mp 200–204° C.

EXAMPLE 64

4-(3,4-Dichlorophenylmethylamino)-6,7-diethoxy-3-quinolinecarbonitrile

In the manner of Example 61 reaction of 4-chloro-6,7-diethoxy-3-quinolinecarbonitrile with 3,4-dichlorobenzylamine gave the title compound as a tan solid, mp 163–165° C.

EXAMPLE 65

4-Methoxy-but-2-enoic Acid [4-(3-bromo-phenylamino)-3-cyano-quinolin-6-yl]-amide To a solution of 1.0 g (2.95 mmol) of of 6-amino-4-[(3-bromophenyl)amino]-3-quinolinecarbonitrile and 0.57 g (4.42 mmol) of diisopropylethyl amine at 0° C. with stirring was added 0.43 g (3.24 mmol) of 4-methoxycrotonyl chloride. After 1.5 hr at 0° C., the mixture was poured into a saturated solution of sodium bicarbonate and then extracted with ethyl acetate. The organic solution was dried over magnesium sulfate and the solvent was removed. The residue was recrystallized from 1-butanol giving 1.3 g of 4-Methoxy-but-2-enoic acid [4-(3-bromo-phenylamino)-3-cyano-quinolin-6-yl]-amide as a yellow solid: mass spectrum (electrospray, m/e,): M+H 436.4, 438.9.

EXAMPLE 66

4-(3-Chloro-propoxy)-5-methoxy-benzoic Acid Methyl Ester

A mixture of 102.4 g (411.7 mmol) of 3-chloropropyl p-toluene sulfonate, 75 g (411.7 mmol) of 4-hydroxy-5-methoxy-benzoic acid methyl ester, 75.7 g (547.5 mmol) of potassium carbonate, and 1.66 g (4.1 mmol) of methyl-tricapryl ammonium chloride in 900 ml of acetone was stirred rapidly at reflux for 18 hr. The mixture was filtered and the solvent was removed giving 106 g of the tile compound after recrystallization from a chloroform-hexane mixture.

EXAMPLE 67

4-(2-Chloro-ethoxy)-5-methoxy-benzoic Acid Methyl Ester

By using an identical method as above 77 g of 4-hydroxy-5-methoxy-benzoic acid methyl ester, 99.2 g of 2-chloroethyl p-toluene sulfonate, 77.7 g of potassium carbonate, and 1.7 g (4.1 mmol) of methyl-tricapryl ammonium chloride was converted to 91.6 g of the title compound: mass spectrum (electrospray, m/e,): M+H 245.0

EXAMPLE 68

4-(3-Chloro-propoxy)-5-methoxy-2-nitro-benzoic Acid Methyl Ester

To a solution of 100 g (386.5 mmol) 4-(3-chloro-propoxy)-5-methoxy-benzoic acid methyl ester in 300 ml acetic acid was added dropwise 100 ml of 70% nitric acid. The mixture was heated to 50° C. for 1 hr and then poured into ice water. The mixture was extracted with chloroform. The organic solution was washed with dilute sodium hydroxide and then dried over magnesium sulfate. The solvent was removed. Ether was added an the mixture was stirred until solid was deposited. The solid was collected by filtration giving 98 g of 4-(3-Chloro-propoxy)-5-methoxy- 2-nitro-benzoic acid methyl ester as white crystals: mass spectrum (electrospray, m/e,): M+H 303.8; 2M+NH$_4$623.9.

EXAMPLE 69

4-(2-Chloro-ethoxy)-5-methoxy-2-nitro-benzoic Acid Methyl Ester

By using an identical method as above 85 g of 4-(2-Chloro-ethoxy)-5-methoxybenzoic acid methyl ester was nitrated to give 72 g of the title compound: mass spectrum (electrospray, m/e,): 2M+NH$_4$ 595.89

EXAMPLE 70

2-Amino-4-(3-chloro-propoxy)-5-methoxy-benzoic Acid Methyl Ester

A mixture of 91 g (299.6 mmol) of 4-(3-chloro-propoxy)-5-methoxy-2-nitro-benzoic acid methyl ester and 55.2 g (988.8 mmol) of iron was mechanically stirred at reflux in a mixture containing 60.1 g ammonium chloride, 500 ml water, and 1300 ml methanol for 5.5 hr. The mixture was concentrated and mixed with ethyl acetate. The organic solution was washed with water and saturated sodium bicarbonate. The solution was dried over magnesium sulfate and filtered through a short column of silica gel. The solvent was removed and the residue mixed with 300 ml of ether-hexane 2:1. After standing 73.9 g of the title compound was obtained as a pink solid: mass spectrum (electrospray, m/e): 2M−HCl+H 511.0; M+H 273.8

EXAMPLE 71

2-Amino-4-(2-chloro-ethoxy)-5-methoxy-benzoic Acid Methyl Ester

A mixture of 68.2 g (235.4 mmol) of 4-(2-chloro-ethoxy)-5-methoxy-2-nitro-benzoic acid methyl ester and 52.6 g (941.8 mmol) of iron was mechanically stirred at reflux in a mixture containing 62.9 g ammonium chloride, 393 ml water, and 1021 ml methanol for 15 hr. The mixture was concentrated and mixed with ethyl acetate. The organic solution was washed with water and saturated sodium bicarbonate. The solution was dried over magnesium sulfate and filtered through a short column of silica gel. The solution was concentrated to 200 ml and diluted with 250 of hot hexane. After standing 47.7 g of the title compound was obtained as a solid: mass spectrum (electrospray, m/e) M+H 259.8.

EXAMPLE 72

7-(2-Chloro-ethoxy)-4-hydroxy-6-methoxy-quinoline-3-carbonitrile

A mixture of 25 g (96.3 mmol) of 2-amino-4-(2-chloro-ethoxy)-5-methoxy-benzoic acid methyl ester and 17.2 g (144.4 mmol) of dimethyformamide dimethyacetal was heated to reflux for 1.5 hr. Excess reagents were removed at reduced pressure leaving 30.3 g of a residue which was dissolved in 350 ml of tetrahydrofuran.

In a separate flask, to a stirred solution of 80.9 ml of 2.5M n-butyl lithium in hexane in 300 ml of tetrahydrofuran at −78° C. was added dropwise 8.3 g (202.1 mmol) of acetonitrile over 40 min. After 30 min, the above solution of amidine was added dropwise over 45 min at −78° C. After 1 hr, 27.5 ml of acetic acid was added and the mixture was allow to warm to room temperature. The solvent was removed and water was added. Solid was collected by filtration and washed with water and ether. After drying in vacumn, 18.5 g of the title compound was obtained as a tan powder: mass spectrum (electrospray, m/e) M+H 278.8.

EXAMPLE 73

7-(3-Chloro-propoxy)-4-hydroxy-6-methoxy-quinoline-3-carbonitrile

By using the above method, starting with 6.01 g of the corresponding amidine, 1.58 g of acetonitrile, and 15.35 ml of n-butyl lithium solution, 3.7 g of the title compound was obtained as a tan powder: mass spectrum (electrospray, m/e) M+H 292.8; 2M+H 584.2

EXAMPLE 74

7-(3-Chloro-propoxy)-4-chloro-6-methoxy-quinoline-3-carbonitrile

A mixture of 3.5 g (12 mmol) of 7-(3-chloro-propoxy)-4-hydroxy-6-methoxy-quinoline-3-carbonitrile and 28 ml of phosphorous oxychloride was refluxed for 1.5 hr. Excess reagent was removed at reduced pressure. The residue was mixed with ice cold dilute sodium hydroxide and ethyl acetate. The mixture was extracted with a combination of ethyl acetate and tetrahydrofuran. The combined extracts were washed with a saturated solution of sodium bicarbonate, dried over magnesium sulfate, and filter through a short column of silica gel. Solvents were removed giving 3.2 g of the title compound as a pink solid that is used with additional purification.

EXAMPLE 75

7-(3-Chloro-ethoxy)-4-chloro-6-methoxy-quinoline-3-carbonitrile

A solution of 8 g (28.7 mmol) of 7-(3-chloro-ethoxy)-4-hydroxy-6-methoxy-quinoline-3-carbonitrile and 18.2 g (143.5 mmol) of oxalyl chloride in 80 ml of methylene chloride containing 0.26 g of dimethylformamide was stirred at reflux for 2.5 hr. The solvent was removed. The residue was mixed with cold dilute sodium hydroxide and extracted several time with ethyl acetate and tetrahydrofuran. The combined extracts were dried over magnesium sulfate and the solution was passed through a short silica gel column. The solvents were removed giving 6.0 g of the title compound as an off-white solid that is used without additional purification.

EXAMPLE 76

4-(4-Chloro-2-fluoro-phenylamino)-7-(3-chloro-propoxy)-6-methoxy-quinoline-3-carbonitrile A mixture of 3.1 g (9.96 mmol) of 7-(3-Chloro-propoxy)-4-chloro-6-methoxy-quinoline-3-carbonitrile, 1.6 g (10.96 mmol) of 4-chloro-2-fluoro-aniline, and 1.2 g (10 mmol) of pyridine hydrochloride in 31 ml of 2-ethoxyethanol was stirred at reflux for 1.5 hr. The mixture was poured into saturated sodium bicarbonate solution and extracted with ethyl acetate. The organic solution was dried and solvent was removed. The residue was purified on a silica gel column eluting with chloroform-ether mixtures to give 2.88 g of the title compound as an off-white solid powder: mass spectrum (electrospray, m/e) M+H 419.7.

EXAMPLE 77

7-(2-Chloro-ethoxy)-4-(3-hydroxy-4-methyl-phenylamino)-6-methoxy-quinoline-3-carbonitrile By using the above method, starting with 3 g of 7-(2-chloro-ethoxy)-4-chloro-6-methoxy-quinoline-3- carbonitrile, 1.37 g of 3-hydroxy-4-methyl-aniline, and 1.2 g of pyridine hydrochloride in 31 ml of 2-ethoxyethanol, 2.6 g of the title compound was obtained as a crystalline solid: mass spectrum (electrospray, m/e) M+H 383.9.

EXAMPLE 78

4-(4-Chloro-2-fluoro-5-hydroxy-phenylamino)-7-(3-chloro-propoxy)-6-methoxy-quinoline-3-carbonitrile By using the above method, starting with 3 g of 7-(3-chloro-propxy)-4-chloro-6-methoxy-quinoline-3-carbonitrile, 2.35 g of the methyl carbonate of 4-chloro-2-fluoro-5-hydroxy-aniline, and 1.1 g of pyridine hydrochloride in 30 ml of 2-ethoxyethanol, 1.7 g of the title compound was obtained as a crystalline solid: mass spectrum (electrospray, m/e) M+H 435.8, 437.8.

EXAMPLE 79

4-(4-Chloro-2-fluoro-5-hydroxy-phenylamino)-7-(2-chloro-ethoxy)-6-methoxy-quinoline-3-carbonitrile By using the above method, starting with 3 g of 7-(2-chloro-ethoxy)-4-chloro-6-methoxy-quinoline-3-carbonitrile, 2.46 g of the methyl carbonate of 4-chloro-2-fluoro-5-hydroxy-aniline, and 1.18 g of pyridine hydrochloride in 31 ml of 2-ethoxyethanol, 2.2 g of the title compound was obtained as a tan solid: mass spectrum (electrospray, m/e) M+H 421.9.

EXAMPLE 80

4-(4-Chloro-2-fluoro-phenylamino)-7-(3-dimethylaminopropoxy)-6-methoxy-quinoline-3-carbonitrile A mixture of 1 g (2.38 mmol) of 4-(4-Chloro-2-fluoro-phenylamino)-7-(3-chloro-propoxy)-6-methoxy-quinoline-3-carbonitrile and 0.07 g of sodium iodide in 17.85 ml of 2M dimethylamine in tetrahydrofuran was placed in a sealed tube and heated to 125° C. for 3.5 hr. The solvent was removed and the residue was mixed with warm ethyl acetate and saturated sodium bicarbonate solution. The organic layer was separated and dried over magnesium sulfate. Solvent was removed and ether was added. One standing, the crystals were deposited giving 0.93 g of the title compound as a white solid: mass spectrum (electrospray, m/e) M+H 428.9.

EXAMPLE 81

4-(4-Chloro-2-fluoro-phenylamino)-6-methoxy-7-(3-morpholin-4-yl-propoxy)-quinoline-3-carbonitrile A mixture of 1 g (2.38 mmol) of 4-(4-Chloro-2-fluoro-phenylamino)-7-(3-chloro-propoxy)-6-methoxy-quinoline-3-carbonitrile, 3.1 g (35.7 mmol) of morpholine, and 0.07 g of sodium iodide in 20 ml ethylene glycol dimethyl ether refluxed for 7 hr. The solvent was removed and the residue was mixed with warm ethyl acetate and saturated sodium bicarbonate solution. The organic layer was separated and dried over magnesium sulfate. Solvent was removed and ether-hexane was added. One standing, the crystals were deposited giving 1.1 g of the title compound as a off-white solid: mass spectrum (electrospray, m/e) M+H 470.9.

EXAMPLE 82

7-(2-Dimethylamino-ethoxy)-4-(3-hydroxy-4-methyl-phenylamino)-6-methoxy-quinoline-3-carbonitrile A mixture of 1 g (2.38 mmol) of 7-(2-chloro-ethoxy)-4-(3-hydroxy-4-methyl-phenylamino)-6-methoxy-quinoline-3-carbonitrile and 0.078 g of sodium iodide in 19.5 ml of 2M dimethylamine in tetrahydrofuran was placed in a sealed tube and heated to 125° C. for 14 hr. The solvent was removed and the residue was mixed with warm ethyl acetate and saturated sodium bicarbonate solution. The organic layer was separated and dried over magnesium sulfate. Solvent was removed and the residue was chromatographed on silica gel eluting with ethyl acetate-methanol-triethylamine 70:30:2.5 giving 0.89 g of the title compound as a light yellow solid: mass spectrum (electrospray, m/e) M+H 393.0; (M+2H)$^{+2}$ 196.9.

EXAMPLE 83

4-(3-Hydroxy-4-methyl-phenylamino)-6-methoxy-7-(2-morpholin-4-yl-ethoxy)-quinoline-3-carbonitrile A mixture of 1 g (2.38 mmol) of 7-(2-chloro-ethoxy)-4-(3-hydroxy-4-methyl-phenylamino)-6-methoxy-quinoline-3-carbonitrile, 3.4 g (39 mmol) of morpholine, and 0.08 g of sodium iodide in 22 ml ethylene glycol dimethyl ether refluxed for 34 hr. The solvent was removed and the residue was mixed with warm ethyl acetate and saturated sodium bicarbonate solution. The organic layer was separated and dried over magnesium sulfate. Solvent was removed and the residue was chromatographed on silica gel eluting with ethyl acetate-methanol-triethylamine 70:30:2.5 giving 1.05 of the title compound as a light orange solid: mass spectrum (electrospray, m/e) M+H 435.0; (M+2H)$^{+2}$ 218.0.

EXAMPLE 84

4-(4-Chloro-2-fluoro-5-hydroxy-phenylamino)-7-(3-dimethylamino-propoxy)-6-methoxy-quinoline-3-carbonitrile A mixture of 0.8 g (1.83 mmol) of 4-(4-chloro-2-fluoro-5-hydroxy-phenylamino)-7-(3-chloro-propoxy)-6-methoxy-quinoline-3-carbonitrile and 0.055 g of sodium iodide in 15.6 ml of 2M dimethylamine in tetrahydrofuran was placed in a sealed tube and heated to 125° C. for 2.5 hr. The solvent was removed and the residue was mixed with warm ethyl acetate and saturated sodium bicarbonate solution. The organic layer was separated and dried over magnesium sulfate. Solvent was removed and the residue was treated with with ethyl acetate-ether depositing a solid and giving 0.51 g of the title compound as a off-white solid: mass spectrum (electrospray, m/e) M+H 445.0; (M+2H)$^{+2}$ 243.4.

EXAMPLE 85

4-(4-Chloro-2-fluoro-5-hydroxy-phenylamino)-6-methoxy-7-(3-morpholin-4-yl-propoxy)-quinoline-3-carbonitrile A mixture of 0.8 g (1.83 mmol) of 4-(4-chloro-2-fluoro-5-hydroxy-phenylamino)-7-(3-chloro-propoxy)-6-methoxy-quinoline-3-carbonitrile, 2.4 g (27.5 mmol) of morpholine, and 0.11 g of sodium iodide in 15 ml ethylene glycol dimethyl ether refluxed for 7 hr. The solvent was removed and the residue was mixed with warm ethyl acetate and saturated sodium bicarbonate solution. The organic layer was separated and dried over magnesium sulfate. Solvent was removed and the residue was recrystallized from ethyl acetate-carbon tetrachloride giving 0.63 of the title compound as a light tan solid: mass spectrum (electrospray, m/e) M+H 487.0; (M+2H)$^{+2}$ 243.9.

EXAMPLE 86

4-(4-Chloro-2-fluoro-5-hydroxy-phenylamino)-7-(2-dimethylamino-ethoxy)-6-methoxy-quinoline-3-carbonitrile A mixture of 0.8 g (1.83 mmol) of 4-(4-chloro-2-fluoro-5-hydroxy-phenylamino)-7-(2-chloro-ethoxy)-6-methoxyquinoline-3-carbonitrile and 0.11 g of sodium iodide in 16.1 ml of 2M dimethylamine in tetrahydrofuran was placed in a sealed tube and heated to 135° C. for 14 hr. The solvent was removed and the residue was mixed with warm ethyl acetate and saturated sodium bicarbonate solution. The organic layer was separated and dried over magnesium sulfate. Solvent was removed and the residue was chromatographed on silica gel eluting with ethyl acetate-methanol-triethylamine 60:40:3 giving 0.41 g of the title compound as a tan solid: mass spectrum (electrospray, m/e) M+H 430.9; $(M+2H)^{+2}$ 216.0.

EXAMPLE 87

4-(4-Chloro-2-fluoro-5-hydroxy-phenylamino)-6-methoxy-7-(2-morpholin-4-yl-ethoxy)-quinoline-3-carbonitrile A mixture of 0.8 g (1.83 mmol) of 4-(4-chloro-2-fluoro-5-hydroxy-phenylamino)-7-(2-chloro-ethoxy)-6-methoxy-quinoline-3-carbonitrile, 2.4 g (27.5 mmol) of morpholine, and 0.11 g of sodium iodide in 15 ml ethylene glycol dimethyl ether heated in a sealed tube at 135° C. for 12 hr. The solvent was removed and the residue was mixed with warm ethyl acetate and saturated sodium bicarbonate solution. The organic layer was separated and dried over magnesium sulfate. Solvent was removed and the residue was chromatographed on silica gel eluting with ethyl acetate-methanol-triethylamine 70:30:1 giving 0.43 g of the title compound as a tan solid: mass spectrum (electrospray, m/e) M+H 470.0; $(M+2H)^{+2}$ 237.0.

EXAMPLE 88

N-[3-Cyano-4-(3-fluorophenylamino)quinolin-6-yl]acrylamide

A solution of 1.00 g (3.60 mmol) of 6-amino-4-(3-fluorophenylamino)quinoline-3-carbonitrile in 12 mL of THF under $N_2$ was chilled in ice. Triethylamine (0.436 g, 4.32 mmol) was added followed by 0.393 g (4.32 mmol) of acryloyl chloride and the reaction was stirred at 25° C. overnight. The solvent was removed and the residue was slurried with water and filtered. The crude product was washed with water, dried, washed with hot ethyl acetate and dried in vacuo (50° C.). This yielded 0.862 g of N-[3-cyano-4-(3-fluorophenylamino)quinolin-6-yl]acrylamide as a brown solid: mass spectrum (electrospray, m/e): M+H 333.1.

EXAMPLE 89

6,7-Dimethoxy-4-(3-nitrophenylamino)quinoline-3-carbonitrile

A solution of 0.500 g (2.00 mmol) of 4-chloro-6,7-dimethoxy-3-quinolinecarbonitrile and 0.332 g (2.41 mmol) of 3-nitroaniline in 6 mL of methyl cellosolve was refluxed under $N_2$ for 8 hr. Methanol was added, followed by satd $NaHCO_3$ (pH 8) and volatile material was removed. The residue was slurried with water, collected by filtration and dried. Recrystallization from ethanol gave 0.480 g of 6,7-dimethoxy-4-(3-nitrophenylamino)quinoline-3-carbonitrile as yellow crystals: mass spectrum (electrospray, m/e): M+H 351.0.

EXAMPLE 90

4-(3-Bromophenylamino)-6-ethoxy-7-methoxyquinoline-3-carbonitrile

A mixture of 1.00 g (3.82 mmol) of 4-chloro-6-ethoxy-7-methoxyquinoline-3-carbonitrile and 0.788 g (4.58 mmol) of 3-bromoaniline in 20 mL of ethanol was refluxed under $N_2$ for 7 h. Saturated $NaHCO_3$ was added, volatile material was removed and the residue was azeotroped with ethanol. The crude product was slurried with hexane, filtered, washed with water and dried. Recrystallization from ethanol gave 1.31 g of 4-(3-bromophenylamino)-6-ethoxy-7-methoxyquinoline-3-carbonitrile as tan crystals: mass spectrum (electrospray, m/e): M+H 397.9, 399.8.

EXAMPLE 91

4-Chloro-6-ethoxy-7-methoxyquinoline-3-carbonitrile

A mixture of 7.95 g (32.6 mmol) of 6-ethoxy-7-methoxy-4-oxo-1,4-dihydroquinoline-3-carbonitrile and 50 mL of phosphorous oxychloride was refluxed for 3 h 40 min. The phosphorous oxychloride was removed in vacuo and the residue was slurried with ice water. Solid $NaHCO_3$ was added (pH8) and the product was collected by filtration, washed well with water and dried in vacuo (40° C.). The yield was 7.75 g of 4-chloro-6-ethoxy-7-methoxyquinoline-3-carbonitrile as a tan solid: mass spectrum (electrospray, m/e): M+H 262.8, 264.8.

EXAMPLE 92

6-Ethoxy-7-methoxy-4-oxo-1,4-dihydroquinoline-3-carbonitrile

A solution of 10.2 g (45.3 mmol) of methyl 2-amino-5-ethoxy-4-methoxy benzoate and 10.8 g (90.7 mmol) of dimethylformamide dimethyl acetal in 50 mL of dimethylformamide was refluxed for 3 h. Volatile material was removed and the residue was azeotroped with toluene and dried in vacuo to give the formamidine as a purple syrup. n-Butyllithium (100 mmol) in hexane was diluted with 60 mL of tetrahydrofuran at −78° C. A solution of 4.18 g (102 mmol) of acetonitrile in 80 mL of tetrahydrofuran was added over 15 min and the solution was stirred for 20 min. The crude formamidine was dissolved in 80 mL of tetrahydrofuran and added dropwise to the cold solution over 0.5 h. After stirring for 2 h, the reaction was quenched at −78° C. with 13 mL of acetic acid. It was allowed to warm to room temperature and volatile material was removed in vacuo. The residue was slurried with water and the crude product was collected by filtration washed with water and dried. This material was then washed with chloroform and dried to give 7.95 g of 6-ethoxy-7-methoxy-4-oxo-1,4-dihydroquinoline-3-carbonitrile as yellow crystals: mass spectrum (electrospray, m/e): M−H 243.2.

EXAMPLE 93

Methyl 2-Amino-5-ethoxy-4-methoxybenzoate

A mixture of 17.0 g (66.7 mmol) of methyl 5-ethoxy-4-methoxy-2-nitrobenzoate, 13.1 g (233 mmol) of powdered iron and 17.7 g (334 mmol) of ammonium chloride in 95 mL of water and 245 mL of methanol was refluxed for 4.5 h. An additional 13.1 g of iron was added followed by refluxing for 2.5 h. Then an additional 13.1 g of iron and 17.7 g of ammonium chloride was added and refluxing was continued for 12 h. The reaction was filtered through Celite and methanol was removed from the filtrate. The filtrate was extracted with chloroform and the extracts were treated with Darco, evaporated and dried in vacuo (50° C.).The yield was 11.0 g of methyl 2-amino-5-ethoxy-4-methoxybenzoate as tan crystals: mass spectrum (electrospray, m/e): M+H 225.9.

EXAMPLE 94

Methyl 5-Ethoxy-4-methoxy-2-nitrobenzoate

A mixture of 15.0 g (74.1 mmol) of methyl 3-ethoxy-4-methoxybenzoate in 45 mL of acetic acid was treated with 15 mL of conc nitric acid dropwise over 12 min. The reaction was kept at 55° C. for 45 min, cooled to 25° C. and poured into ice water. The product was extracted into methylene chloride and the extracts were washed with water and dil sodium hydroxide, dried and evaporated. The yield was 17.8 g of methyl 5-ethoxy-4-methoxy-2-nitrobenzoate as yellow crystals: mass spectrum (electrospray, m/e): M+H 256.0.

EXAMPLE 95

Methyl 3-Ethoxy-4-methoxybenzoate

A mixture of 24.3 g (134 mmol) of methyl 3-hydroxy-4-methoxybenzoate, 36.8 g (267 mmol) of anhyd potassium carbonate and 31.4 g (201 mmol) of ethyl iodide in 500 mL of dimethylformamide was stirred at 100° C. for 5.5 h. An additional amount of ethyl iodide (31.4 g) and potassium carbonate (18.4 g) was added and heating was continued for 2 h more. The reaction was filtered and volatile material was removed from the filtrate in vacuo. The residue was slurried with water and filtered to collect the product which was washed with water and dried. Recrystallization from heptane gave 15.6 g of methyl 3-ethoxy-4-methoxybenzoate as white crystals: mass spectrum (electrospray, m/e): M+H 210.9.

EXAMPLE 96

Methyl 3-Hydroxy-4-methoxybenzoate

A solution of 30.8 g (183 mmol) of 3-hydroxy-4-methoxybenzoic acid and 6 mL of conc sulfuric acid in 600 mL of methanol was refluxed overnight. Most of the solvent was removed and the remaining solution was poured into 600 mL of water containing 25 g of sodium bicarbonate. The product was extracted into ether, treated with Darco, dried and evaporated. The yield was 31.8 g of methyl 3-hydroxy-4-methoxybenzoate as pale yellow crystals.

EXAMPLE 97

6-Ethoxy-4-(3-hydroxy-4-methylphenylamino)-7-methoxyquinoline-3-carbonitrile A mixture of 1.00 g (3.82 mmol) of 4-chloro-6-ethoxy-7-methoxyquinoline-3-carbonitrile and 0.563 g (4.58 mmol) of 3-hydroxy-4-methylaniline in 20 mL of ethanol was refluxed under $N_2$ for 8 h. Saturated $NaHCO_3$ was added, volatile material was removed and the residue was azeotroped with ethanol. The crude product was slurried with hexane, filtered, washed with water and cold ethanol and dried. Recrystallization from ethanol gave 0.632 g of 6-ethoxy-4-(3-hydroxy-4-methylphenylamino)-7-methoxyquinoline-3-carbonitrile as light yellow crystals: mass spectrum (electrospray, m/e): M+H 349.9.

EXAMPLE 98

4-Bromo-but-2-enoic acid [4-(3-bromo-phenylamino)-3-cyano-quinolin-6-yl]-amide A solution of 1.65 grams (0.01 mole) of 4-bromo crotonic acid (Giza Braun, J. Am. Chem. Soc. 52, 3167 1930) in 15 ml of dichloromethane was treated with 1.74 ml (0.02 moles) of oxalyl chloride and 1 drop of N,N-dimethylformamide. After an hour the solvents were removed on the rotary evaporator. The residual oil was taken up in 25 ml of tetrahydrofuran, and 3.39 grams of 6-Amino-4-(3-bromo-phenylamino)-quinoline-3-carbonitrile in 25 ml of tetrahydrofuran was added dropwise. This was followed by the dropwise addition of 1.92 ml (0.011 moles) of diisopropylethylamine. After the addition of 25 ml of water and 50 ml of ethyl acetate, the layers were separated. The organic layer was dried over anhydrous sodium sulfate, and taken to a solid in vacuo. This solid was digested for an hour with refluxing ethyl acetate then filtered from the ethyl acetate while still hot. Thus was obtained 3.31 grams (68%) of 4-bromo-but-2-enoic acid[4-(3-bromo-phenylamino)-3-cyano-quinolin-6-yl]-amide.

EXAMPLE 99

4-Dimethylamino-but-2-enoic Acid [4-(3-bromo-phenylamino)-3-cyano-quinolin-6-yl]-amide Fifteen milliliters of a 2 molar solution of dimethylamine in tetrahydrofuran was cooled in an ice bath and a solution of 729 mg (1.5 mmoles) of 4-bromo-but-2-enoic acid[4-(3-bromo-phenylamino)-3-cyano-quinolin-6-yl]-amide in 5 ml of N,N-dimethylformamide was added dropwise. Stirring and cooling were continued for 2 hours. Then 25 ml of water and 15 ml of ethyl acetate were added. The layers were separated and the organic layer was extracted with an addition 25 ml of water. The combined aqueous layers were extracted with 2–25 ml portions of 1:1 tetrahydrofuran-ethyl acetate. The combined organic layers were absorbed onto silica gel and chromatographed on silica gel. The column was eluted with a gradient of 1:19 to 1:4 methanol-methylene chloride. Obtained was 381 mg (56%) of 4-Dimethylamino-but-2-enoic acid [4-(3-bromo-phenylamino)-3-cyano-quinolin-6-yl]-amide which melted at 209–211 deg.: mass spectrum (electrospray, m/e): M+H 225.5, 226.2.

EXAMPLE 100

4-Diethylamino-but-2-enoic Acid[4-(3-bromo-phenylamino)-3-cyano-quinolin-6-yl]-amide A solution of 3.15 ml (30 mmoles) of diethylamine in 15 ml of tetrahydrofuran was cooled in an ice bath and a solution of 729 mg (1.5 mmoles) of 4-bromo-but-2-enoic acid[4-(3-bromo-phenylamino)-3-cyano-quinolin-6-yl]-amide in 5 ml of N,N-dimethylformamide was added dropwise. Stirring and cooling were continued for 2 hours. Then 25 ml of water and 15 ml of ethyl acetate were added. The layers were separated and aqueous layer was extracted with 2–15 ml portions of 1:1 tetrahydrofuran-ethyl acetate. The combined organic layers were absorbed onto silica gel and chromatographed on silica gel. The column was eluted with a gradient of 1:19 to 1:4 methanol-methylene chloride to give 367 mg (51%) of 4-Diethylamino-but-2-enoic acid[4-(3-bromo-phenylamino)-3-cyano-quinolin-6-yl]-amide. The compound melted at 141–145 deg: mass spectrum (electrospray, m/e): M+H 478.0, 480.0.

EXAMPLE 101

4-Methylamino-but-2-enoic Acid[4-(3-bromo-phenylamino)-3-cyano-quinolin-6-yl]-amide Fifteen milliliters of a 2 molar solution of methylamine in tetrahydrofuran was cooled in an ice bath and a solution of 729 mg (1.5 mmoles) of 4-bromo-but-2-enoic acid[4-(3-bromo-phenylamino)-3-cyano-quinolin-6-yl]-amide in 5 ml of N,N-dimethylformamide was added dropwise. Stirring and cooling were continued for 2 hours. Then 25 ml of water and 15 ml of ethyl acetate were added. The layers were separated aqueous layer was extracted with 2–15 ml portions of 1:1 tetrahydrofuran-ethyl acetate. The combined organic layers were absorbed onto silica gel and chromatographed on silica gel The column was eluted with a gradient of 1:19 to 1:1 methanol-methylene chloride. Obtained was 210 mg (32%) of 4-Methylamino-but-2-enoic acid[4-(3-bromo-phenylamino)-3-cyano-quinolin-6-yl]-amide which slowly went to a tar in the range of 194–202 deg.: mass spectrum (electrospray, m/e): M+H 437.9; M+2H 219.5.

EXAMPLE 102

2-Cyano-3-(2-methyl-4-nitrophenyl)acrylic Acid Ethyl Ester

A mixture of 2-methyl-4-nitroaniline (38.0 g, 250 mmol), ethyl (ethoxymethylene)cyanoacetate (50.8 g, 300 mmol), and 200 ml of toluene was refluxed for 24 h, cooled, diluted with 1:1 ether-hexane, and filtered. The resulting white solid was washed with hexane-ether and dried to give 63.9 g, mp 180–210° C.

EXAMPLE 103

1,4-Dihydroquinoline-8-methyl-6-nitro-3-carbonitrile

A stirred mixture of 64 g (230 mmol) of 2-cyano-3-(2-methyl-4-nitrophenyl)acrylic acid ethyl ester and 1.5 L of Dowtherm A was heated at 260° C. for 12 h, cooled, diluted with hexane, and filtered. The grey solid thus obtained was washed with hexane and dried to give 51.5 g, mp 295–305° C.

EXAMPLE 104

4-Chloro-8-methyl-6-nitro-3-quinolinecarbonitrile

A stirred mixture of 1,4-dihydroquinoline-8-methyl-6-nitro-3-carbonitrile (47 g, 200 mmol) and 200 ml of phosphorous oxychloride was refluxed for 4 h. The phosphorous oxychloride was removed in vacuo, and the residue was stirred with methylene chloride at 0° C. and treated with a slurry of ice and sodium carbonate. The organic layer was separated and washed with water. The solution was dried and concentrated to a volume of 700 ml. The product was precipitated by the addition of hexane and cooling to 0° C. The white solid was filtered off and dried to give 41.6 g, mp 210–212° C.

EXAMPLE 105

4-[(3-Bromophenyl)amino]-8-methyl-6-nitro-3-quinolinecarbonitrile

A stirred mixture of 4-chloro-8-methyl-6-nitro-3-quinolinecarbonitrile (14.8 g, 60 mmol), 3-bromoaniline (12.4 g, 72 mmol), pyridine hydrochloride (6.93 g, 60 mmol), and 180 ml of ethoxyethanol was refluxed for 1.5 h, cooled, poured into a stirred mixture of water and an amount of sodium carbonate to give a pH of 8–9. The resulting yellow solid was filtered, washed with water, dried, digested in boiling ether, filtered, and dried to give 22.6 g, mp 263–267° C.

EXAMPLE 106

4-[(3-Bromohenyl)-N-acetylamino]-8-methyl-6-nitro-3-quinolinecarbonitrile

A stirred mixture of 4-[(3-bromophenyl)amino]-8-methyl-6-nitro-3-quinolinecarbonitrile (15.3 g, 40 mmol), 0.37 g (3 mmol) of dimethylaminopyridine, 40 ml of acetic anhydride, and 80 ml of pyridine was refluxed for 3 h and concentrated at 50° C. under vacuum. The residue was stirred with methylene chloride and 0.1 N HCl. After filtration through Celite, the organic layer was washed with water, dried and concentrated. The residue was subjected to chromatography on silica gel with 1% acetic acid in methylene chloride to give 11.2 g of an amber glass, NMR (CDCl$_3$) $\delta$ 2.29 (N-acetyl group).

EXAMPLE 107

8-Bromomethyl-4-[(3-bromophenyl)-N-acetylamino]-6-nitro-3-quinolinecarbonitrile

A stirred mixture of 4-[(3-bromophenyl)-N-acetylamino]-8-methyl-6-nitro-3-quinolinecarbonitrile (10.6 g, 25 mmol), N-bromosuccinimide (6.68 g, 37.5 mmol), 0.30 g of dibenzoyl peroxide, and 200 ml of carbon tetrachloride was refluxed for 2 h, treated with an additional 0.30 g of dibenzoyl peroxide, and refluxed an additional 2.5 h, cooled, diluted with methylene chloride, and stirred with aqueous sodium bisulfite. The organic layer was separated and washed successively with water, sodium bicarbonate solution, and water. The solution was dried and evaporated to give 15 g of a white foam, NMR (CDCl$_3$) $\delta$ 5.19 (dd, C$\underline{H}_2$Br).

EXAMPLE 108

4-[(3-Bromophenyl)amino-8-dimethylaminomethyl-6-nitro-3-quinolinecarbonitrile

To a stirred solution of dimethylamine in THF (2.0 M; 115 ml; 230 mmol) at 0° C. was added a solution of 8-bromomethyl 4-[(3-bromophenyl)-N-acetylamino]-6-nitro-3-quinolinecarbonitrile (11.6 g, 23 mmol) in 115 ml of THF during 15 m. After warming to 25° C. the mixture was stirred for 2 h. The THF was evaporated off, and the residue was refluxed in 230 ml of methanol with 12.7 g (92 mmol) of potassium carbonate for 1 h. The mixture was cooled, saturated with CO$_2$, and concentrated. The residue was partitioned with methylene chloride and water. The organic layer was washed with water, dried, and concentrated. The residue was subjected to chromatography on silica gel with methylene chloride-ethyl acetate-methanol-triethylamine to give 6.0 g yellow solid, mp 223–226° C.

EXAMPLE 109

6-Amino-4-[(3-bromophenyl)amino]-8-dimethylaminomethyl-3-quinolinecarbonitrile

A stirred mixture of 4-[(3-bromophenyl)amino]-8-dimethylaminomethyl-6-nitro-3-quinolinecarbonitrile (5.98 g, 14.1 mmol), iron powder (2.76 g, 49 mg-atoms), acetic acid (5.67 ml, 99 mmol), and 70 ml of methanol was refluxed for 2 h and then evaporated to remove methanol. The residue was stirred with water for 10 m, and the orange solid was filtered off and washed with 2% acetic acid. The total filtrate was basified to $_{pH}$ 10 with 5 N sodium hydroxide. The resulting precipitate was extracted with methylene chloride. The extract was washed with water, dried, and concentrated. The residue was subjected to chromatography on silica gel with ethyl acetate-methanol-triethylamine to give 3.34 g of amber solid; mass spectrum (electrospray, m/e) M+H 396.2, 398.1.

EXAMPLE 110

N-{4-[(3-Bromophenyl)amino]-3-cyano-8-dimethylaminomethyl-6-quinolinyl}-2-butynamide To a stirred mixture of 2-butynoic acid (0.42 g, 5.0 mmol) and N-methylmorpholine (0.66 ml, 6.0 mmol) in 4.0 ml of THF at 0° C. was added i-butyl chloroformate (0.52 ml, 4.0 mmol) during 10 m. After 10 m a solution of 6-amino-4-[(3-bromophenyl)amino]-8-dimethylaminomethyl-3-quinolinecarbonitrile (0.79 g, 2.0 mmol) in 4.0 ml of THF was added during 60 s. The mixture was warmed to 25° C., stirred for 2 h, and diluted with water. The $_{pH}$ was adjusted to 9–10 with potassium carbonate, and the resulting solid was filtered off, washed with water, stirred with methylene chloride, and filtered. The latter filtrate was concentrated to give a solid which was subjected to chromatography on silica gel with methylene chloride-ethyl acetate-methanol-triethylamine to give an amber solid; mass spectrum (electrospray, m/e) M+H 462, 464.

EXAMPLE 111

N-{4-[(3-Bromophenyl)amino]-3-cyano-8-dimethylaminomethyl-6-quinolinyl}-2-propenamide To a stirred solution of 6-amino-4-[(3-bromophenyl)amino]-8-dimethylaminomethyl-3-quinolinecarbonitrile (0.20 g, 0.50 mmol) and N,N-diisopropylethylamine (0.13 ml, 0.75 mmol) in 3.4 ml of THF at 0° C. was added acryloyl chloride (0.045 ml, 0.55 mmol) during 5 m. After stirring for 3 h at 0° C. the mixture was diluted with sodium bicarbonate solution. The resulting solid was filtered off, washed with water, dried, and subjected to chromatography on silica gel with methylene chloride-ethyl acetate-methanol-triethylamine to give a yellow solid; mass spectrum (electrospray, m/e) M+H 449.9, 452.0.

EXAMPLE 112

N-{4-[(3-Bromophenyl)amino]-3-cyano-8-dimethylaminomethyl-6-quinolinyl}acetamide To a stirred mixture of 6-amino-4-[(3-bromophenyl)amino]-8-dimethylaminomethyl-3-quinolinecarbonitrile (0.20 g, 0.50 mmol) and 1.5 ml of acetic acid at 25° C. was added 0.14 ml (1.5 mmol) of acetic anhydride. After 60 m volatile matter was evaporated off under vacuum. The residue was stirred with sodium bicarbonate solution. The resulting solid was filtered off, washed with water, dried, and recrystallized from isopropanol-hexane to give a light yellow solid, mp 162–167° C.

EXAMPLE 113

N'-[2-Carbethoxy-4,5-bis(2-methoxyethoxy)phenyl]-N,N-dimethylformamidine

To a stirred solution of 15.7 g (50 mmol) of ethyl 2-amino-4,5-bis(2-methoxyethoxy)benzoate (Pfizer patent WO 96130347) in 50 ml of DMF at 0° C. was added phosphorous oxychloride (5.6 ml, 60 mmol) during 15 m. The resulting solution was heated at 55° C. for 45 m, cooled, diluted with methylene chloride, and treated at 0° C. with 200 ml of N/1 sodium hydroxide during 2 m. The organic layer was separated and washed at 0° C. with water. The solution was dried and evaporated with added toluene present to give 18.4 g of amber oil; NMR (CDCl$_3$) δ 3.02 (s, Me$_2$N).

EXAMPLE 114

1,4-Dihydroquinoline-5,6-bis(2-methoxyethoxy)-3-carbonitrile

To a stirred solution of n-butyllithium (44 ml of 2.5 M in hexane; 110 mmol) in 65 ml of THF at −78° C. was added a solution of acetonitrile (5.85 ml, 112 mmol) in 110 ml of THF during 10 m. After stirring at −78° C. for 15 m, the mixture was treated with a solution of N'-[2-carbethoxy-4,5-bis(2-methoxyethoxy)phenyl]-N,N-dimethylformamidine in 75 ml of THF during 20 m. After 30 m at −78° C. the stirred mixture was treated with acetic acid (14.3 ml, 250 mmol). The mixture was warmed to 25° C. and stirred for 2 h. The mixture was evaporated to dryness, and diluted with water. The resulting white solid was filtered, washed with water, and dried to give 10.7 g; mass spectrum (electrospray, m/e) M+H 319.2.

EXAMPLE 115

4-Chloro-5,6-bis(2-methoxyethoxy)-3-quinolinecarbonitrile

A stirred mixture of 1,4-dihydroquinoline-5,6-bis(2-methoxyethoxy)-3-carbonitrile 9.68 g, 30.4 mmol) and 30 ml of phosphorous oxychloride was refluxed for 1.5 h. The resulting solution was concentrated under vacuum, and the residue was stirred with methylene chloride at 0° C. as ice-water and sodium carbonate were added until pH of mixture was 8–9. The organic layer was separated, washed with water, dried and concentrated to give a tan solid; mass spectrum (electrospray, m/e) M+H 337.1, 339.1.

EXAMPLE 116

4-[(3-Ethynylphenyl)amino]-5,6-bis(2-methoxyethoxy)-3-quinolinecarbonitrile

A stirred mixture of 4-Chloro-5,6-bis(2-methoxyethoxy)-3-quinolinecarbonitrile (2.52 g, 7.5 mmol), pyridine hydrochloride (0.87 g, 9.0 mmol), 3-ethynylaniline (1.06 g, 9.0 mmol), and ethoxyethanol (22 ml) was refluxed for 1.5 h, cooled, diluted with water containing potassium carbonate to give pH~9, and extracted with ethyl acetate. The extract was washed well with water, dried, and concentrated. The resulting solid was recrystallized from ethyl acetate to give an off-white solid, mp 150–153°.

EXAMPLE 117

4-[3-Dimethylaminophenyl)amino]-5,6-bis(2-methoxyethoxy)-3-quinolinecarbonitrile A stirred mixture of 4-Chloro-5,6-bis(2-methoxyethoxy)-3-quinolinecarbonitrile (0.67 g, 2.0 mmol), pyridine (0.39 ml, 4.8 mmol), 3-dimethylaminoaniline dihydrochloride (0.50 g, 2.4 mmol), and ethoxyethanol (6.0 ml) was refluxed for 2 h, cooled, and partitioned with ethyl acetate and water containing potassium carbonate to give ph~9–10. The organic layer was washed with water, dried and concentrated. The residue was chromatographed on silica gel with methylene chloride-ethyl acetate-methanol to give an amber glass; mass spectrum (electrospray, m/e) M+H 437.0.

EXAMPLE 118

4-[(3-Acetylphenyl)amino]-5,6-bis(2-methoxyethoxy)-3-quinolinecarbonitrile

In the manner of Example 116, 4-Chloro-5,6-bis(2-methoxyethoxy)-3-quinolinecarbonitrile was reacted with 3-aminoacetophenone to give the title compound; recrystallized from ethanol to give off-white solid, mp 250–253 (dec).

EXAMPLE 119

Methyl 4-Methoxy-3-(3-morpholin-4-yl-propoxy)) benzoate

A stirred mixture of methyl isovanillate (22.6 g, 124 mmol), N-(3-chloropropyl)-morpholine (25.4 g, 155 mmol), potassium carbonate (18.8 g, 136 mmol), tetrabutylammonium iodide (0.92 g, 2.5 mmol), and 248 ml of 2-butanone was refluxed for 20 h. The 2-butanone was evaporated off, and the residue was stirred with water at 0° C. The resulting white solid was filtered off, washed successively with water and hexane, and dried; mp 90–94° C.

EXAMPLE 120

Methyl 4-methoxy-5-(3-morpholin-4-yl-propoxy))-2-nitrobenzoate

To a stirred solution of methyl 4-methoxy-3-(3-morpholin-4-yl-propoxy))benzoate (30.9 g, 100 mmol) in 100 ml of acetic acid at 25° C. was added 50 ml of 70% nitric acid during 30 m. The solution was heated to 45° C. at which point the reaction started and was self-sustaining at that temperature. After a total of 1.5 h at 45–50° C. the mixture was cooled to 0° C., treated with ice-water and 240 g (1.75 mol) of potassium carbonate, and extracted with ethyl acetate. The extract was washed with water, dried, and concentrated to give a yellow solid, mp 78–82° C.

EXAMPLE 121

Methyl 2-Amino-4-methoxy-5-(3-morpholin-4-yl-propoxy))benzoate

A solution of methyl 4-methoxy-3-(3-morpholin-4-yl-propoxy))-2-nitrobenzoate (32.5 g, 91.7 mmol) in 110 ml of methanol and 220 ml of ethyl acetate was hydrogenated at 55 psi in the presence of 2.0 g of 10% Pd on carbon catalyst at 25° C. After 4 h the mixture was filtered, and the filtrate was evaporated to dryness. The residue was recrystallized from acetone-hexane to give a tan solid, mp 78–82° C.

EXAMPLE 122

Ethyl 2-(Dimethylaminomethyleneamino)-4-methoxy-5-(3-morpholin-4-yl-propoxy))benzoate A mixture of methyl 2-amino-4-methoxy-5-(3-morpholin-4-yl-propoxy))benzoate (6.49 g, 20 mmol) and dimethylformamide dimethyl acetal (4.25 ml, 30 mmol) was heated at 100° C. for 1.5 h. All volatile materials were evaporated off directly at 70° C. to give a syrup; mass spectrum (electrospray, m/e) M+H 380.5.

EXAMPLE 123

1,4-Dihydroquinoline-7-methoxy-6-(3-morpholin-4-yl-propoxy))-4-oxo-3-carbonitrile To a stirred solution of n-butyllithium (17.6 ml of 2.5 M in hexane; 44 mmol) in 26 ml of THF at −78° C. was added a solution of acetonitrile (1.85 ml, 45 mmol) in 44 ml of THF during 10 m. After stirring at −78° C. for 15 m, the mixture was treated with a solution of ethyl 2-(dimethylaminomethyleneamino)-4-methoxy-5-(3-morpholin-4-yl-propoxy))benzoate (7.6 g, 20 mmol) in 30 ml of THF during 20 m. After 90 m at −78° C. the mixture was treated with carbon dioxide while warming slowly to 25° C. and then evaporated to dryness. The residue was partitioned with n-butanol (200 ml) and half-saturated NaCl solution (40 ml). The organic layer was separated, washed with saturated NaCl solution, and evaporated to dryness. The resulting solid was triturated successively with boiling acetone and methanol, filtered, and dried to give a tan solid, mp 255–260° C.

EXAMPLE 124

4-Chloro-7-methoxy-6-(3-morpholin-4-yl-propoxy))-3-quinolinecarbonitrile

A stirred mixture of 1,4-Dihydroquinoline-7-methoxy-6-(3-morpholin-4-yl-propoxy))-4-oxo-3-carbonitrile (4.75 g, 13.8 mmol), 0.10 ml of DMF, and 55 ml of thionyl chloride was refluxed for 3 h. Volatile matter was removed by evaporation at 30° C., and the residue was stirred at 0° C. with a mixture of methylene chloride and water containing potassium carbonate to give pH 9–10. The organic layer was separated, washed with water, dried and concentrated to give a brown solid; mass spectrum (electrospray, m/e) M+H 362.4, 364.4.

EXAMPLE 125

4-[(3-Chloro-4-fluorophenyl)amino]-7-methoxy-6-(3-morpholin-4-yl-propoxy))-3-quinolinecarbonitrile A stirred mixture of 4-chloro-7-methoxy-6-(3-morpholin-4-yl-propoxy))-3-quinolinecarbonitrile (1.8 g, 5.0 mmol), 3-chloro-4-fluoroaniline (0.87 g, 6.0 mmol), pyridine hydrochloride (1.15 g, 10 mmol), and 15 ml of ethoxyethanol was refluxed for 2 h, cooled, and stirred with hexane and water containing potassium carbonate to give pH 10. The resulting brown solid was filtered off, washed with water and hexane, and dried. Recrystallization from ethanol gave an off-white solid, mp 240–244° C.

EXAMPLE 126

4-[(3-Bromophenyl)amino]-7-methoxy-6-(3-morpholin-4-yl-propoxy))-3-quinolinecarbonitrile In the manner of Example 125, 4-chloro-7-methoxy-6-(3-morpholin-4-yl-propoxy))-3-quinolinecarbonitrile was reacted with 3-bromoaniline to give the title compound; recrystallized from methanol to give an off-white solid, mp 208–212° C.

EXAMPLE 127

4-[(4-Chloro-2-fluorophenol)amino]-7-methoxy-6-(3-morpholin-4-yl-proloxy))-3-quinolinecarbonitrile In the manner of Example 125, 4-chloro-7-methoxy-6-(3-morpholin-4-yl-propoxy))-3-quinolinecarbonitrile was reacted with 4-chloro-2-fluoroaniline to give the title compound; recrystallized from methanol to give an off-white solid, mp 207–212° C.

EXAMPLE 128

4-[(3-Hydroxy-4-methylphenyl)amino]-7-methoxy-6-(3-morpholin-4-yl-propoxy))-3-quinolinecarbonitrile In the manner of Example 125, 4-chloro-7-methoxy-6-(3-morpholin-4-yl-propoxy))-3-quinolinecarbonitrile was reacted with 3-hydroxy-4-methylaniline to give the title compound; recrystallized from ethyl acetate to give an amber solid, mp 222–227° C. (dec).

EXAMPLE 129

N-{3-Cyano-4-[(3-iodophenyl)amino]-6-quinolinyl}-2-propenamide

Dissolved 500 mg (1.29 mmol) 6-amino-4-[(3-iodophenyl)amino]-3-quinolinecarbonitrile in 1.0 ml of DMF and added 6 ml THF. Chilled to 0° C. under $N_2$ and added 200 µl (1.43 mmol) triethyl amine and 120 µl (1.44 mmol) acryloyl chloride. Removed ice bath at 15 minutes. At 1.5 hours stripped solvent. Slurried residue with water and dilute sodium bicarbonate. Collected, washed with

EXAMPLE 130

6-Amino-4-[(3-iodophenyl)amino]-3-quinolinecarbonitrile

A mixture of 6.70 g (16.1 mmol) 4-[(3-iodophenyl)amino]-6-nitro-3-quinolinecarbonitrile, 300 ml ethanol, and 18.2 g (80.5 mmol) $SnCl_2$ dihydrate was heated to reflux under $N_2$. Removed heat at 2 hours, added ice water. Added sodium bicarbonate until pH was basic, forming a thick yellow mixture. Stirred for 2.5 hours. Extracted with chloroform, stirred organic portion with Darco and filtered through magnesium sulfate. Stripped solvent and dried in vacuo, giving 3.48 g of yellow-brown solid: mass spectrum (electrospray m/e): M+H=387.0.

EXAMPLE 131

4-[(3-Iodophenyl)amino]-6-nitro-3-quinolinecarbonitrile

A mixture of 3.10 ml (25.7 mmol) 3-iodoaniline, 200 ml ethanol, and 5.00 g (21.4 mmol) 4-chloro-6-nitro-3-quinolinecarbonitrile was heated to reflux under $N_2$ for 3.5 hours. Cooled and made basic with a saturated sodium bicarbonate. Stripped solvents and azeotroped with ethanol. Slurried residue with hexane and collected. Air dried, washed solids with water, and dried in vacuo. Dissolved solids in 400 ml ethyl acetate, stirred with Darco, filtered and removed solvent. Dried solids in vacuo to give 7.38 g of yellow solid: mass spectrum (electrospray m/e): M+H=417.0.

EXAMPLE 132

N-{3-Cyano-4-[(3-methylphenyl)amino]-6-quinolinyl}-2-butynamide

Dissolved 597 mg (7.10 mmol) 2-butynoic acid in 25 ml THF under $N_2$ and chilled to 0° C. Added 950 µl (7.30 mmol) isobutyl chloroformate and 780 µl (7.10 mmol) N-methylmorpholine and stirred for 10 minutes. Added dropwise a solution of 778 mg (2.84 mmol 6-amino-4-[(3-methylphenyl)amino]-3-quinolinecarbonitrile, stirred for 15 minutes at 0° C. and then at 25° C. overnight. Stripped solvent and slurried residue with water, drying the gummy solid in vacuo briefly. Boiled solid in ethyl acetate and collected. Recrystallized from DMF, using ethanol to crash out the product, and dried in vacuo, giving 401 mg of yellow-brown solid: mass spectrum (electrospray m/e): M+H=341.2.

EXAMPLE 133

6-Amino-4-[(3-methylphenyl)amino]-3-quinolinecarbonitrile

Added 253 mg 10% palladium on carbon to a round bottom flask under $N_2$ and covered catalyst with 140 ml ethanol. To this added 2.49 g (8.18 mmol) 6-nitro-4-[(3-methylphenyl)amino]-3-quinolinecarbonitrile and 640 µl (20.4 mmol) anhydrous hydrazine. The mixture was heated to reflux for 2 hours 15 minutes and filtered hot through celite. Stripped solvent and dried in vacuo, giving 2.455 g of yellow solid: mass spectrum (electrospray m/e): M+H=275.2.

EXAMPLE 134

6-Nitro-4-[(3-methylphenyl)amino]-3-quinolinecarbonitrile

A mixture of 5.00 g (21.5 mmol) 4-chloro-6-nitro-3-quinolinecarbonitrile, 200 ml ethanol, and 2.75 ml (25.7 mmol) 3-toluidine was heated to reflux for 4.5 hours. Cooled and added a saturated sodium bicarbonate until pH was basic. Stripped solvents and azeotroped with ethanol. Slurried with hexane, collected, and air dried. Washed with water and dried in vacuo. Boiled in ethyl acetate, stirred with Darco and filtered. Stripped solvent and dried in vacuo to give 4.82 g of yellow-orange solid: mass spectrum (electrospray m/e): M+H=305.2.

EXAMPLE 135

N-{4-[(3-Chlorophenyl)amino]-3-cyano-6-quinolinyl}-2-propenamide

Dissolved 430 mg (1.46 mmol) 6-amino-4-[(3-chlorophenyl)amino]-3-quinolinecarbonitrile in 4 ml DMF, added 10 ml THF and chilled to 0° C. under $N_2$. Added 224 µl (1.60 mmol) triethylamine and 133 µl (1.60 mmol) acryloyl chloride. Removed ice bath at 15 minutes, reaction complete at this time, but stirred overnight at 25° C. Stripped solvent, added a dilute sodium bicarbonate to the residue and collected solids. Washed with water and dried in vacuo. Boiled in ethyl acetate, collected solids and dried in vacuo, giving 200 mg of orange solid: mass spectrum (electrospray m/e): M+H=349.0, 351.0.

EXAMPLE 136

6-Amino-4-[(3-chlorophenyl)amino]-3-quinolinecarbonitrile

A mixture of 6.30 g (19.4 mmol) 4-[(3-chlorophenyl)amino]-6-nitro-3-quinolinecarbonitrile, 300 ml ethanol, and 21.9 g (97 mmol) $SnCl_2$ dihydrate were heated to reflux under $N_2$. Removed heat at 2.5 hours, added ice water and made basic with sodium bicarbonate. Stirred for 2 hours and extracted with chloroform. Dried organic layer with sodium sulfate, filtered, stripped solvent and dried residue in vacuo, giving 5.74 g of yellow-brown solid: mass spectrum (electrospray m/e): M+H=295.1, 297.1.

EXAMPLE 137

4-[(3-Chlorophenyl)amino]-6-nitro-3-quinolinecarbonitrile

A mixture of 10.0 g (42.9 mmol)) 4-chloro-6-nitro-3-quinolinecarbonitrile, 260 ml ethanol, and 5.40 ml 3-chloroaniline was heated to reflux under $N_2$. Removed heat at 4 hours, cooled to 25° C. and added saturated sodium bicarbonate until the pH was basic. Stripped solvents and azeotroped with ethanol. Slurried residue with hexane, collected solid, and air dried. Washed solids with water and dried in vacuo. Dissolved in boiling ethyl acetate, stirred with Darco, and filtered. Stripped solvent and dried residue in vacuo, giving 6.5 g of yellow solid: mass spectrum (electrospray m/e): M+H=325.0, 327.0.

EXAMPLE 138

N-{3-Cyano-4-[(3-methoxyphenyl)amino]-6-quinolinyl}-2-propenamide

Dissolved 500 mg (1.72 mmol) 6-amino-4-[(3-methoxyphenyl)amino]-3-quinolinecarbonitrile in 2 ml hot

--- water, air dried. Boiled solids in ethyl acetate. Filtered off solids, removed solvent of the filtrate, and dried in vacuo, giving 391 mg of orange-brown solid: mass spectrum (electrospray m/e): M+H=441.1.

DMF, added 6 ml THF, and chilled to 0° C. Added 264 µl (1.90 mmol) triethylamine and 158 µl (1.90 mmol) acryloyl chloride. Removed ice bath at 15 minutes. Stripped solvent at 2 hours. Washed residue with dilute sodium bicarbonate, collected solids, washed with water, and air dried. Boiled solids in ethyl acetate, collected and dried in vacuo, giving 288 mg of yellow-orange solid: mass spectrum (electrospray m/e): M+H=345.2.

EXAMPLE 139

N-{3-Cyano-4-[(3-methoxyphenyl)amino]-6-quinolinyl}-2-butynamide

Dissolved 362 mg (4.31 mmol) acid in 20 ml THF under $N_2$ and chilled to 0° C. Added 560 µl (4.30 mmol) isobutyl chloroformate and 475 µl (4.31 mmol) N-methylmorpholine and stirred for 10 minutes. Dissolved 500 mg (1.72 mmol) 6-amino-4-[(3-methoxyphenyl)amino]-3-quinolinecarbonitrile in 2 ml hot DMF and added 10 ml THF. Added this to the mixed anhydride dropwise, stirred for 15 minutes at 0° C. and at 25° C. overnight. Stripped solvent, slurried residue with water, collected solids, and air dried. Recrystallized from ethyl acetate and dried in vacuo, giving 270 mg of yellow solid: mass spectrum (electrospray m/e): M+H=357.1.

EXAMPLE 140

N-{3-Cyano-4-[(3-methoxyphenyl)amino]-6-quinolinyl}-4-piperidino-2-butynamide

Partially dissolved 1.21 (7.22 mmol) 4-piperidino-2-butynoic acid in 100 ml THF and chilled to 0° C. under $N_2$. Added 955 µl (8.67 mmol) N-methylmorpholine and 750 µl (5.78 mmol) isobutyl chloroformate. Stirred for 40 minutes and added a solution of 840 mg (2.89 mmol) 6-amino-4-[(3-methoxyphenyl)amino]-3-quinolinecarbonitrile dissolved in 10 ml hot pyridine. At 2 hours, poured into ice water and made basic with saturated sodium bicarbonate. Extracted with ethyl acetate, dried with sodium sulfate, and stripped down to a small volume, which was loaded onto a column of silica gel. Eluted with 10% methanol/ethyl acetate, stripped solvent of desired fractions, and dried in vacuo, giving 970 mg of green solid: mass spectrum (electrospray m/e): M+H=440.1.

EXAMPLE 141

6-Amino-4-[(3-methoxyphenyl)amino]-3-quinolinecarbonitrile 325 mg of 10% palladium on carbon was added to a round bottom flask under $N_2$ and covered with 165 ml ethanol. Added 3.29 g (10.3 mmol) 4-[(3-methoxyphenyl)amino]-6-nitro-3-quinolinecarbonitrile and 800 µl anhydrous hydrazine and heated mixture to reflux. At 1.5 hours, filtered hot through celite, stripped solvent and dried in vacuo, giving 2.876 g of yellow solid: mass spectrum (electrospray m/e): M+H=291.2.

EXAMPLE 142

4-[(3-Methoxyphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.0 ml (26.0 mmol) m-anisidine was heated to reflux under $N_2$. Removed heat at 4.5 hours and made basic with saturated sodium bicarbonate. Stripped solvents and azeotroped with ethanol. Slurried with hexane and collected crystals. Washed with water, dried in vacuo. Dissolved 5.94 g of crude product in 320 ml boiling ethyl acetate, stirred with Darco, filtered, stripped solvent, and dried in vacuo, giving about 5 g of yellow-orange solid: mass spectrum (electrospray m/e): M+H=291.1.

EXAMPLE 143

N-{4-[(3-Chloro-4-fluoro-phenyl)amino]-3-cyano-6-quinolinyl}-2-butynamide

Dissolved 336 mg (4.00 mmol) 2-butynoic acid in 20 ml of THF and chilled to 0° C. under $N_2$. Added 520 µl (4.00 mmol) isobutyl chloroformate and 440 µl (4.00 mmol) N-methylmorpholine and stirred for 10 minutes. Added a solution of 500 mg (1.60 mmol) 6-amino-4-[(3-chloro-4-fluorophenyl)amino]-3-quinolinecarbonitrile, stirred for 15 minutes at 0° C. and then at 25° C. overnight. Stripped solvent, washed with water, collected and dried in vacuo. Recrystallized from ethyl acetate, giving 148 mg of a yellow solid: mass spectrum (electrospray m/e): M+H=379.1, 381.1.

EXAMPLE 144

N-{4-[(3-Chloro-4-fluorophenyl)amino]-3-cyano-6-quinolinyl}-2-propenamide

Dissolved 1.00 g (3.20 mmol) 6-amino-4-[(3-chloro-4-fluorophenyl)amino]-3-quinolinecarbonitrile in 2 ml hot DMF, added 12 ml THF and chilled to 0° C. under $N_2$. Added 490 µl (3.52 mmol) triethyl amine and 295 µl (3.52 mmol) acryloyl chloride. Removed ice bath at 15 minutes, and at 1.5 hours stripped solvent. Slurried residue with a dilute sodium bicarbonate, collected solids, and washed with water. Recrystallized from ethyl acetate, giving 215 mg of yellow solid: mass spectrum (electrospray m/e): M+H= 367.1, 369.1.

EXAMPLE 145

N-{4-[(3-Chloro-4-fluorophenyl)amino]-3-cyano-6-quinolinyl}-4-dimethylamino-2-butenamide Dissolved 1.50 g (4.80 mmol) 6-amino-4-[(3-chloro-4-fluorophenyl)amino]-3-quinolinecarbonitrile in 50 ml THF, added 836 µl (4.80 mmol) N,N-diisopropylethylamine, and chilled to 0° C. under $N_2$. Added 500 µl (4.80 mmol) 4-bromo-but-2-enoyl chloride and after 1 hour dropwise added the mixture to 10 ml of a 2M solution (19 mmol) of dimethylamine in THF cooled to −78° C. At 2 hours, added 5 ml (9.5 mmol) more of dimethyl amine solution and warmed to 25° C. After 1 hour, poured onto a cold solution of sodium bicarbonate. Extracted with ethyl acetate, dried organics with brine and sodium sulfate, reduced to small volume and loaded onto a column of silica gel. Eluted with 70% methanol/ethyl acetate, stripped solvent of desired fractions and dried in vacuo, giving 427 mg of yellow solid: mass spectrum (electrospray m/e): M+H=424.0, 426.0.

EXAMPLE 146

N-{4-[(3-Chloro-4-fluorophenyl)amino]-3-cyano-6-quinolinyl}-4-diethylamino-2-butenamide Added 500 µl (4.80 mmol) 4-bromo-but-2-enoyl chloride to a solution of 1.50 g (4.80 mmol)) 6-amino-4-[(3-chloro-4-fluorophenyl)amino]-3-quinolinecarbonitrile and 836 µl (4.80 mmol) N,N-diisopropylethylamine in 50 ml THF at 0° C. under $N_2$. At 1 hour added the mixture dropwise to 1.26 ml (24 mmol) diethylamine in 11 ml THF chilled to −78° C. Removed dry ice bath after complete addition, and at 2 hours, 45 minutes poured onto a mixture of ice and saturated sodium bicarbonate. Extracted with ethyl acetate, dried organic layer with brine and sodium sulfate, and stripped solvent. Loaded compound onto a column of silica gel, eluted with 35% methanol/ethyl acetate, stripped solvent from desired fractions, and dried in vacuo, giving 292 mg of yellow-orange solid: mass spectrum (electrospray m/e): M+H=452.4, 454.4.

EXAMPLE 147

N-{4-[(3-Chloro-4-fluorophenyl)amino]-3-cyano-6-quinolinyl}-4-morpholino-2-butenamide Added 500 μl (4.80 mmol) 4-bromo-but-2-enoyl chloride to a solution of 1.50 g (4.80 mmol) 6-amino-4-[(3-chloro-4-fluorophenyl)amino]-3-quinolinecarbonitrile and 836 μl (4.80 mmol) N,N-diisopropylethylamine in 50 ml THF at 0° C. under $N_2$. At 1 hour added the mixture dropwise to 2.09 ml (24 mmol) morpholine in 10 ml THF at 0° C. Removed ice bath upon complete addition and at 3 hours, poured reaction onto a mixture of ice and saturated sodium bicarbonate. Extracted with ethyl acetate, dried organic layer with brine and sodium sulfate, and stripped solvent. Loaded compound onto a column of silica gel, eluted with 12% methanol/ethyl acetate, stripped solvent from desired fractions, and dried in vacuo, giving 798 mg of yellow solid: mass spectrum (electrospray m/e): M+H=466.4, 468.4.

EXAMPLE 148

N-{4-[(3-Chloro-4-fluorophenyl)amino]-3-cyano-6-quinolinyl}-2-morpholin-4-ylmethyl-2-propenamide Partially dissolved 1.37 g (8.00 mmol) 2-morpholin-4-ylmethyl-2-propenoic acid in 50 ml THF and chilled to 0° C. under $N_2$. Added 1.06 ml (9.6 mmol) N-methylmorpholine and 833 μl (6.4 mmol) isobutyl chloroformate. Stirred at 0° C. for 1 hour and added a solution of 1.00 g (3.20 mmol) 6-amino-4-[(3-chloro-4-fluorophenyl)amino]-3-quinolinecarbonitrile in 5 ml pyridine. Stirred overnight at 25° C. Poured onto a mixture of ice and saturated sodium bicarbonate, extracted with ethyl acetate, dried organic layer with brine and sodium sulfate, and stripped solvent to a small volume. Loaded onto a column of silica gel, eluted with 1% methanol/ethyl acetate, stripped solvent from desired fractions and dried under vacuum, giving 139 mg of yellow-orange solid: mass spectrum (electrospray m/e): M+H=465.8, 468.0.

EXAMPLE 149

6-Amino-4-[(3-chloro-4-fluorophenyl)amino]-3-quinolinecarbonitrile

A mixture of 5.360 g (15.6 mmol) 4-[(3-chloro-4-fluorophenyl)amino]-6-nitro-3-quinolinecarbonitrile, 250 ml ethanol, and 17.67 g (78.2 mmol) $SnCl_2$ dihydrate was heated to reflux under $N_2$. Removed heat at 1.5 hours and added ice water. Made basic with sodium bicarbonate. Stirred for 2 hours extracted with chloroform. Added brine to the separatory funnel to help separate layers. Stirred organic layer with Darco and dried with sodium sulfate. Filtered, stripped solvent and dried in vacuo, giving 4.460 g of yellow-brown solid: mass spectrum (electrospray m/e): M+H=312.9, 315.0.

EXAMPLE 150

4-[(3-Chloro-4-fluorophenyl)amino]-6-nitro-3-quinolinecarbonitrile

A mixture of 5.00 g (21.5 mmol) 4-chloro-6-nitro-3-quinolinecarbonitrile, 200 ml ethanol, and 3.75 g (25.8 mmol) 3-chloro-4-fluoroaniline was heated to reflux under $N_2$. Removed heat at 3.5 hours and added a solution of saturated sodium bicarbonate until mixture was basic. Stripped solvents and azeotroped with ethanol. Slurried residue with hexane, collected solids, washed with water and dried in vacuo. Dissolved solids in 250 ml boiling ethyl acetate, stirred with Darco, and filtered. Stripped solvent and dried in vacuo, giving 6.036 g of yellow solid: mass spectrum (electrospray m/e): M+H=343.1, 345.1.

EXAMPLE 151

N-{4-[(4-Bromophenyl)amino]-3-cyano-6-quinolinyl}-2-propenamide

Dissolved 500 mg (1.47 mmol) 6-amino-4-[(4-bromophenyl)amino]-3-quinolinecarbonitrile in 1 ml hot DMF, added 6 ml THF and chilled to 0° C. under $N_2$. Added 226 μl (1.62 mmol) triethylamine and 135 μl (1.62 mmol) acryloyl chloride. Removed ice bath at 15 minutes. At 1.5 hours, stripped solvent, slurried residue in dilute sodium bicarbonate, collected solids, and dried in vacuo. Boiled solids in ethyl acetate, collected, and dried in vacuo, giving 194 mg of yellow-orange solid: mass spectrum (electrospray m/e): M+H=393.1, 395.1.

EXAMPLE 152

6-Amino-4-[(4-bromophenyl)amino]-3-quinolinecarbonitrile

A mixture of 3.10 g (8.40 mmol) 4-[(4-bromophenyl)amino]-6-nitro-3-quinolinecarbonitrile, 155 ml ethanol, and 9.47 g (42.0 mmol) $SnCl_2$ dihydrate was heated to reflux under $N_2$. After 4 hours, removed heat and added ice water. Made basic with sodium bicarbonate and stirred for 2 hours. With mixture still basic, extracted with chloroform, stirred organic layer with Darco and dried with sodium sulfate. Filtered, stripped solvent and dried in vacuo, giving 2.265 g of brown-yellow solid: mass spectrum (electrospray m/e): M+H=339.0, 341.0.

EXAMPLE 153

4-[(4-Bromophenyl)amino]-6-nitro-3-quinolinecarbonitrile

A mixture of 5.00 g (21.5 mmol) 4-chloro-6-nitro-3-quinolinecarbonitrile, 200 ml ethanol, and 4.42 g (25.8 mmol) p-bromoaniline was heated to reflux under $N_2$ for 3 hours. Removed heat and added saturated sodium bicarbonate until basic. Stripped solvents and azeotroped with ethanol. Slurried residue with hexane, collected solids, and air dried. Washed with water and dried in vacuo. Boiled in 1.4 liters ethyl acetate, and without completely dissolving all solids, stirred with Darco, and filtered. Stripped solvent and dried in vacuo, giving 3.524 g of yellow solid: mass spectrum (electrospray m/e): M+H=369, 370.9.

EXAMPLE 154

N-{3-Cyano-4-[(3,4-difluorophenyl)amino]-6-quinolinyl}-2-propenamide

Dissolved 1.00 g (3.37 mmol) 6-amino-4-[(3,4-difluorophenyl)amino]-3-quinolinecarbonitrile in 2 ml DMF, added 12 ml THF, and chilled to 0° C. under N$_2$. Added 517 µl (3.71 mmol) triethylamine and 310 µl (3.72 mmol) acryloyl chloride. Removed ice bath a 15 minutes. At 3.5 hours stripped solvent and slurried residue with dilute sodium bicarbonate. Collected solids, washed with water, and air dried. Boiled in ethyl acetate, collected solids and dried in vacuo, giving 332 mg of yellow solid: mass spectrum (electrospray m/e): M+H=351.1.

EXAMPLE 155

6-Amino-4-[(3,4-difluorophenyl)amino]-3-quinolinecarbonitrile

A mixture of 4.53 g (13.9 mmol) 4-[(3,4-difluorophenyl)amino]-6-nitro-3-quinolinecarbonitrile, 200 ml ethanol and 15.72 g (69.4 mmol) SnCl$_2$ dihydrate was heated to reflux under N$_2$. Removed heat at 1.5 hours, added ice water and made basic with sodium bicarbonate. Stirred for 2 hours and extracted with chloroform. Stirred organic layer with Darco, dried with sodium sulfate and filtered. Stripped solvent and dried in vacuo, giving 3.660 g of yellow-green solid: mass spectrum (electrospray m/e): M+H=297.1.

EXAMPLE 156

4-[(3,4-Difluorophenyl)amino]-6-nitro-3-quinolinecarbonitrile

A mixture of 5.00 g (21.5 mmol) 4-chloro-6-nitro-3-quinolinecarbonitrile, 250 ml ethanol and 2.55 ml (25.8 mmol) 3,4-difluoroaniline was heated to reflux under N$_2$. Removed heat at 3.5 hours and made basic with saturated sodium bicarbonate. Stripped solvents and azeotroped with ethanol. Slurried residue with hexane, collected solids and air dried. Washed with water and dried in vacuo. Dissolved in ethyl acetate, stirred with Darco, filtered, stripped solvent and dried in vacuo, giving ethyl acetate, stirred with Darco, filtered, stripped solvent and dried in vacuo, giving 5.02 g of yellow solid: mass spectrum (electrospray m/e): M+H=327.1.

EXAMPLE 157

N-{4-[(3-Chloro-4-thiophenoxyphenyl)amino]-3-cyano-6-quinolinyl}-2-butynamide

Dissolved 314 mg (3.72 mmol) 2-butynoic acid in 40 ml THF under N$_2$. Chilled to 0° and added 409 µl (3.72 mmol) N-methylmorpholine and 485 µl (3.72 mmol) isobutyl chloroformate and stirred for 10 minutes. Added dropwise a solution that was prepared by dissolving 1.00 g (2.48 mmol) 6-amino-4-[(3-chloro-4-thiophenoxyphenyl)amino]-3-quinolinecarbonitrile in 2.0 ml hot DMF and adding 20 ml THF. Stirred mixture for 15 minutes at 0° and 25° C. overnight. To drive reaction to completion, added 1.24 mmol of the mixed anhydride (104 mg acid, 136 µl NMM, and 161 µl isobutyl chloroformate) in 15 ml THF. Stirred overnight. Stripped solvent, dried in vacuo. Recrystallized from ethyl acetate, dried in vacuo, giving 284 mg of yellow-orange solid: mass spectrum (electrospray m/e): M+H=469.2, 471.2.

EXAMPLE 158

6-Amino-4-[(3-chloro-4-thiophenoxyphenyl)amino]-3-quinolinecarbonitrile

A mixture of 6.753 g (15.6 mmol) 4-[(3-chloro-4-thiophenoxyphenyl)amino]-6-nitro-3-quinolinecarbonitrile, 250 ml ethanol, and 17.66 g (78.0 mmol) SnCl$_2$ dihydrate was heated to reflux under N$_2$. Removed heat at 2 hours, added large volume of ice water, and made basic with sodium bicarbonate. Stirred for 2 hours and with mixture still basic, extracted with chloroform. Stirred organic layer with Darco, dried with sodium sulfate, filtered, stripped solvent and dried in vacuo, giving 5.996 g of yellow-brown solid: mass spectrum (electrospray m/e): M+H=403.1, 405.1.

EXAMPLE 159

4-[(3-Chloro-4-thiophenoxyphenyl)amino]-6-nitro-3-quinolinecarbonitrile

A mixture of 5.00 g (21.5 mmol) 4-chloro-6-nitro-3-quinolinecarbonitrile, 250 ml ethanol, and 6.07 g (25.6 mmol) 3-chloro-4-thiophenoxyaniline was heated to reflux under N$_2$. Removed heat at about 8 hours, made basic with saturated sodium bicarbonate, stripped solvents and azeotroped with ethanol. Slurried residue with hexane and collected solids. Washed with water and dried in vacuo. Dissolved nearly completely in 400 ml ethyl acetate, stirred with Darco and filtered. Stripped solvent and boiled in hexane to remove last of the excess aniline. Dried in vacuo, giving 6.90 g of red solid: mass spectrum (electrospray m/e): M+H=433.1, 435.1.

EXAMPLE 160

N-{3-Cyano-4-[(3-cyanophenyl)amino]-6-quinolinyl}-2-propenamide

Dissolved 729 mg (2.56 mmol) 6-amino-4-[(3-cyanophenyl)amino]-3-quinolinecarbonitrile in 2 ml hot DMF, added 12 ml THF and cooled to 0° C. under N$_2$. Added 392 µl (2.81 mmol) triethylamine and 234 µl (2.81 mmol) acryloyl chloride. Removed ice bath after 15 minutes and stripped solvent at 2 hours. Washed residue with water and collected solids. Recrystallized from ethyl acetate and dried in vacuo, giving 318 mg of yellow solid: mass spectrum (electrospray m/e): M+H=340.1.

EXAMPLE 161

N-{3-Cyano-4-[(3-cyanophenyl)amino]-6-quinolinyl}-4-pieridino-2-butynamide

Partially dissolved 1.46 g (8.75 mmol) 4-piperidino-2-butynoic acid in 100 ml THF and chilled to 0° C. under N$_2$. Added 1.16 ml (10.5 mmol) N-methylmorpholine and 911 µl (7.00 mmol) isobutyl chloroformate and stirred for 30 minutes. Added a solution of 1.00 g (3.50 mmol) 6-amino-4-[(3-cyanophenyl)amino]-3-quinolinecarbonitrile in 8 ml pyridine. At 3.5 hours poured onto ice bath and made basic with saturated sodium bicarbonate. Extracted with ethyl acetate, dried organic layers with magnesium sulfate, filtered, and reduced solvent to a small volume. Loaded compound onto a column of silica gel and eluted with 7% methanol/ethyl acetate. Stripped solvent from desired fractions and dried in vacuo, giving 1.008 g of off-white solid: mass spectrum (electrospray m/e): 435.0.

EXAMPLE 162

6-Amino-4-[(3-cyanophenyl)amino]-3-quinolinecarbonitrile

Added 100 mg of 10% palladium on carbon to a round bottom flask under N$_2$ and covered with 50 ml ethanol.

Added 1.00 g (3.17 mmol) 4-[(3-cyanophenyl)amino]-6-nitro-3-quinolinecarbonitrile and 250 μl (7.39 mmol) anhydrous hydrazine and heated to reflux. Removed heat at 2 hours and filtered hot through celite. Stripped solvent and dried in vacuo, giving 887 mg of yellow solid: mass spectrum (electrospray m/e): M+H=286.2.

EXAMPLE 163

4-[(3-Cyanophenyl)amino]-6-nitro-3-quinolinecarbonitrile

A mixture of 5.00 g (21.5 mmol) 4-chloro-6-nitro-3-quinolinecarbonitrile, 200 ml ethanol, and 3.04 g (25.8 mmol) 3-aminobenzonitrile was heated to reflux. Removed heat at 3.5 hours and made basic with saturated sodium bicarbonate. Stripped solvents and air dried. Slurried residue with hexane and collected solids. Washed with water and dried in vacuo. Boiled in large volume ethyl acetate, collected solids and dried in vacuo, giving 5.15 g of yellow-brown solid: mass spectrum (electrospray m/e): 316.0.

EXAMPLE 164

N-{3-Cyano-4-[(3-ethylphenyl)amino]-6-quinolinyl}-2-butynamide

Dissolved 370 mg (4.40 mmol) 2-butynoic acid in 20 ml THF under $N_2$ and chilled to 0° C. Added 484 μl (4.40 mmol) N-methylmorpholine and 572 μl (4.40 mmol) isobutyl chloroformate and stirred for 10 minutes. Added a solution of 500 mg (1.76 mmol) 6-amino-4-[(3-ethynylphenyl)amino]-quinoline-3-carbonitrile in 1 ml DMF and 10 ml THF. Removed ice bath at 15 minutes and stirred overnight at 25° C. Stripped solvent, slurried residue with water, collected solids, and dried in vacuo. Boiled in ethyl acetate, collected solids and dried in vacuo, giving 494 mg of yellow solid: mass spectrum (electrospray m/e): M+H=350.9.

EXAMPLE 165

N-{3-Cyano-4-[(3-ethynylphenyl)amino]-6-quinolinyl}-2-propenamide

Dissolved 1.00 g (3.52 mmol) 6-amino-4-[(3-ethynylphenyl)amino)-3-quinolinecarbonitrile in 2 ml hot DMF, added 12 ml THF and chilled to 0° C. under $N_2$. Added 539 μl (3.87 mmol) triethylamine and 322 μl (3.87 mmol) acryloyl chloride. Removed ice bath at 15 minutes and stripped solvent at 1.5 hours. Slurried residue in water, collected solids and air dried overnight. Recrystallized from ethyl acetate, dried in vacuo, giving 302 mg of orange solid: mass spectrum (electrospray m/e): 339.1.

EXAMPLE 166

N-{3-cyano-4-[(3-ethynylphenyl)amino]-6-quinolinyl}-4-piperidino-2-butynamide Partially dissolved 1.03 g (6.16 mmol) 4-piperidino-2-butynoic acid in 70 ml THF and chilled to 0° under $N_2$. Added 812 μl (7.38 mmol) N-methylmorpholine and 640 μl (4.92 mmol) isobutyl chloroformate. After 0.5 hour stirring, added a solution of 700 mg (2.46 mmol) 6-amino-4-[(3-ethynylphenyl)amino)-3-quinolinecarbonitrile dissolved in 5 ml pyridine. At 1 hours poured onto ice bath and made basic with a saturated solution of sodium bicarbonate. Extracted with ethyl acetate, dried organics with sodium sulfate, reduced to a small volume and loaded onto a column of silica gel. Eluted with 8% methanol in ethyl acetate. Stripped solvent of desired fractions and dried in vacuo, giving 641 mg of yellow-orange solid: mass spectrum (electrospray m/e): M+H=434.2.

EXAMPLE 167

6-Amino-4-[(3-ethynylphenyl)amino)-3-quinolinecarbonitrile

A mixture of 2.00 g (6.36 mmol) 4-[(3-ethynylphenyl)amino]-6-nitro-3-quinoline-carbonitrile, 100 ml ethanol, and 7.19 g (31.8 mmol) $SnCl_2$ dihydrate was heated to reflux under $N_2$. Removed heat at 3.5 hours and added ice water. Made basic with sodium bicarbonate and stirred for 2 hours. Extracted with chloroform, stirred organic layer with Darco, dried with sodium sulfate, filtered, stripped solvent, and dried in vacuo, giving 1.737 g of yellow-brown solid: mass spectrum (electrospray m/e): M+H=285.2.

EXAMPLE 168

4-[(3-Ethynylphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.82 g (32.6 mmol) 3-ethynylaniline was heated to reflux under $N_2$. Removed heat at 3.5 hours and added a solution of saturated sodium bicarbonate until basic. Stripped solvents and azeotroped with ethanol. Slurried residue with hexane and collected solids. Washed with water and dried in vacuo. Dissolved in ethyl acetate, stirred with Darco, filtered, stripped solvent and dried in vacuo, giving 4.544 g of yellow solid: mass spectrum (electrospray m/e): M+H=315.1.

EXAMPLE 169

N-{4-[(3-Bromophenyl)amino]-3-cyano-6-quinolinyl}-4-piperidino-2-butynamide

Partially dissolved 1.23 g (7.37 mmol) 4-piperidino-2-butynoic acid in 40 ml THF and chilled to 0° C. under $N_2$. Added 973 μl (8.4 mmol) N-methylmorpholine and 768 μl (5.9 mmol) isobutyl chloroformate. Stirred 10 minutes and added a solution of 1.00 g (2.95 mmol) 6-amino-4-[(3-bromophenyl)amino]-3-quinolinecarbonitrile in 2 ml DMF and 10 ml THF. Removed ice bath at 15 minutes and at 5 hours added 2.95 mmol more of mixed anhydride (0.493 g acid, 487 μl NMM, and 384 μl isobutyl chloroformate), stirred overnight at 25° C. Stripped solvent, slurried residue with water, and collected solids. Boiled in ethyl acetate and collected. Dissolved in 20% methanol/chloroform and coated 5 g of silica gel. Flash chromatographed with 20% methanol/ethyl acetate, stripped solvent of desired fractions and dried in vacuo, giving 122 mg of brown solid: mass spectrum (electrospray m/e): M+H=488.0, 489.9.

EXAMPLE 170

N-{4-[(3-Bromophenyl)amino]-3-cyano-6-quinolinyl}-4-dipropylamino-2-butynamide Partially dissolved 1.28 g (7.0 mmol) 4-dipropylamino-2-butynoic acid in 100 ml THF and chilled to 0° C. under $N_2$. Added 974 μl (8.85 mmol) N-methylmorpholine 768 μl (5.90 mmol) isobutyl chloroformate and stirred for 30 minutes. Added a solution of 1.00 g (2.95 mmol) ) 6-amino-4-[(3-bromophenyl)amino]-3-quinolinecarbonitrile in 8 ml pyridine. At two hours, quenched with ice water and extracted with ethyl acetate. Dried organic layer with magnesium sulfate, reduced solvent to a small volume and loaded onto a column of silica gel. Eluted with ethyl acetate, stripped solvent from desired fractions and dried in vacuo, giving 764 mg of yellow solid: mass spectrum (electrospray m/e): M+H=504, 506.4.

EXAMPLE 171

N-{4-[(3-Bromophenyl)amino]-3-cyano-6-quinolinyl}-2-morpholin-4-ylmethyl-2-propenamide Partially dissolved 1.26 g (7.37 mmol) 2-morpholin-4-ylmethyl-2-propenoic acid in 40 ml THF and chilled to 0° C. under $N_2$. Added 810 µl (7.37 mmol) N-methylmorpholine and 950 µl (7.37 mmol) isobutyl chloroformate. After stirring 10 minutes, added a solution of 1.00 g (2.95 mmol) 6-amino-4-[(3-bromophenyl)amino]-3-quinolinecarbonitrile in 2.5 ml DMF and 20 ml THF. Stripped solvent at 2 hours, slurried residue with water, collected solids, and dried in vacuo. Recrystallized from ethyl acetate and dried in vacuo, giving 334 mg of yellow-orange solid: mass spectrum (electrospray m/e): M+H=492, 494.3.

EXAMPLE 172

N-{4-[(3-Bromo-4-fluorophenyl)amino]-3-cyano-6-quinolinyl}-4-dimethylamino-2-butenamide Made 2.25 mmol of 5-bromo-but-2-enoyl chloride by mixing 386 µl (2.25 mmol) trimethylsilyl 4-bromo-but-2-enoate, 10 ml methylene chloride, 294 µl (3.38 mmol) oxalyl chloride, and 2 drops of DMF. After bubbling had subsided, removed solvent and dissolved in 10 ml THF. This solution was added to a mixture of 800 mg (2.25 mmol) 6-amino-4-[(3-bromo-4-fluorophenyl)amino]-3-quinolinecarbonitrile, 50 ml THF, and 392 µl (2.25 mmol) N,N-diisopropylethylamine chilled to 0° C. under $N_2$. At 1 hour, added dropwise to a solution of 5.62 ml of 2.0M dimethyl amine in THF (11.2 mmol) at −78° C. Removed dry ice bath after complete addition. After 2 hours, poured into a cold solution of sodium bicarbonate, extracted with ethyl acetate, dried organic layer with sodium sulfate and reduced solvent to a small volume. Loaded onto a column of silica gel and eluted with 50% methanol/ethyl acetate. Stripped solvent of desired fractions and dried in vacuo, giving 386 mg of yellow solid: mass spectrum (electrospray m/e): M+H=467.9, 469.9.

EXAMPLE 173

N-{4-[(3-Bromo-4-fluorophenyl)amino]-3-cyano-6-quinolinyl}-4-diethylamino-2-butenamide Made 2.25 mmol of 5-bromo-but-2-enoyl chloride by mixing 386 µl (2.25 mmol) trimethylsilyl 4-bromo-but-2-enoate, 10 ml methylene chloride, 294 µl (3.38 mmol) oxalyl chloride, and 2 drops of DMF. After bubbling had subsided, removed solvent and dissolved in 10 ml THF. This solution was added to a mixture of 800 mg (2.25 mmol) 6-amino-4-[(3-bromo-4-fluorophenyl)amino]-3-quinolinecarbonitrile, 50 ml THF, 3 ml DMF (failed to dissolve amine) and 392 µl (2.25 mmol) N,N-diisopropylethylamine chilled to 0° C. under $N_2$. Removed ice bath at 20 minutes. At 1 hour added dropwise to a solution of 1.2 ml (11.2 mmol) diethylamine in 4.4 ml THF chilled to −78° C. Removed dry ice bath after complete addition and stirred for 3 hours. Poured into a mixture of ice and saturated sodium bicarbonate, extracted with ethyl acetate, dried organic layer with sodium sulfate and reduced solvent to a small volume. Loaded compound onto a column of silica gel, eluted with 30% methanol/ethyl acetate, stripped solvent from desired fractions and dried in vacuo, giving 321 mg of yellow-brown solid: mass spectrum (electrospray m/e): M+H=496.0, 497.9.

EXAMPLE 174

N-{4-[(3-Bromo-4-fluorophenyl)amino]-3-cyano-6-quinolinyl}-4-morpholino-2-butenamide Made 2.25 mmol of 5-bromo-but-2-enoyl chloride by mixing 386 µl (2.25 mmol) trimethylsilyl 4-bromo-but-2-enoate, 10 ml methylene chloride, 294 µl (3.38 mmol) oxalyl chloride, and 2 drops of DMF. After bubbling had subsided, removed solvent and dissolved in 10 ml THF. This solution was added to a mixture of 800 mg (2.25 mmol) 6-amino-4-[(3-bromo-4-fluorophenyl)amino]-3-quinolinecarbonitrile, 50 ml THF, and 392 t (2.25 mmol) N,N-diisopropylethylamine chilled to 0° C. under $N_2$. At 1 hour, added the mixture dropwise to a solution of 1 ml (11.2 mmol) morpholine in 4.5 ml THF chilled to 0° C. After complete addition, removed the ice bath, and at 2 hours poured onto a mixture of ice and saturated sodium bicarbonate. Extracted with ethyl acetate, dried organic layer with sodium sulfate and reduced solvent to a small volume. Loaded onto a column of silica gel, eluted with 12% methanol/ethyl acetate, stripped solvent from desired fractions and dried in vacuo, giving 369 mg of yellow solid: mass spectrum (electrospray m/e): M+H=509.9, 511.9.

EXAMPLE 175

N-{4-[(3-Bromo-4-fluorophenyl)amino]-3-cyano-7-methoxy-6-quinolinyl}-4-morpholino-2-butenamide Made 2.07 mmol of 5-bromo-but-2-enoyl chloride by mixing 363 µl (2.07 mmol) trimethylsilyl 4-bromo-but-2-enoate, 8 ml methylene chloride, 270 µl (3.10 mmol) oxalyl chloride and 2 drops of DMF. Removed solvent when bubbling subsided and dissolved in 10 ml THF. The acid chloride solution was added to a mixture of 800 mg (2.07 mmol) 6-amino-4-[(3-bromo-4-fluorophenyl)amino]-7-methoxy-3-quinolinecarbonitrile, 50 ml THF, and 721 µl (4.14 mmol) N,N-diisopropylethylamine chilled to 0° C. under $N_2$. At 1.5 hours added this mixture to a solution of 900 µl (10.4 mmol) morpholine in 4.3 ml THF at 0° C. Warmed to 25° C. after complete addition, and at 2 hours added 900 µl more morpholine. At 3 hours, poured onto a mixture of ice and saturated sodium bicarbonate, extracted with ethyl acetate, dried with sodium sulfate, and reduced solvent to a small volume. Loaded compound onto a column of silica gel, eluted with 12% methanol/ethyl acetate, stripped solvent from desired fractions, and dried in vacuo, giving 287 mg of orange-brown solid: mass spectrum (electrospray m/e): M+H=539.9, 541.9.

EXAMPLE 176

4-[(3-Bromophenyl)amino]-7-ethoxy-6-methoxy-3-quinolinecarbonitrile

A mixture of 500 mg (1.90 mmol) 4-chloro-7-ethoxy-6-methoxy-3-quinolinecarbonitrile, 20 ml ethanol, and 250 µl (2.28 mmol) 3-bromoaniline was heated to reflux under $N_2$. At 3 hours, added 103 µl (0.95 mmol) and 10 ml ethanol and refluxed overnight. Removed heat and made basic with saturated sodium bicarbonate. Stripped solvent, slurried residue with hexane, collected solids, and dried. Washed with water and dried in vacuo, giving 554 mg of tan solid: mass spectrum (electrospray m/e): M+H=398, 399.8.

EXAMPLE 177

7-Ethoxy-4-[(3-hydroxy-4-methylphenyl)amino]-6-methoxy-3-quinolinecarbonitrile

A mixture of 500 mg (1.90 mmol) 4-chloro-7-ethoxy-6-methoxy-3-quinolinecarbonitrile, 30 ml ethanol, and 281 mg (2.28 mmol) 3-hydroxy-4-methylaniline was heated to reflux under $N_2$ overnight. Removed heat and made basic with saturated sodium bicarbonate. Stripped solvents and slurried residue in hexane. Collected solids, washed with water, and dried in vacuo, giving 364 mg off-white solid: mass spectrum (electrospray m/e): M+H=349.9.

EXAMPLE 178

4-Chloro-7-ethoxy-6-methoxy-3-quinolinecarbonitrile

Mixed 122 mg (0.50 mmol) 7-ethoxy-1,4-dihydro-6-methoxy-4-oxo-3-quinolinecarbonitrile and 2.0 ml methylene chloride under $N_2$ and kept temperature near 25° C. Added 218 µl (2.5 mmol) oxalyl chloride and 10 µl (0.125 mmol) DMF. Stirred overnight, diluted with chloroform and stirred in saturated sodium bicarbonate until basic. Separated layers and dried organics with magnesium sulfate, stripped solvent and dried in vacuo, giving 117 mg of tan solid: mass spectrum (electrospray m/e): M+H=262.8, 264.8.

EXAMPLE 179

7-Ethoxy-1,4-dihydro-6-methoxy-4-oxo-3-quinolinecarbonitrile

Added 54.0 ml (135 mmol) n-butyl lithium to 150 ml THF and chilled to −78° C. under $N_2$. Added dropwise over 20 minutes 7.05 ml (135 mmol) acetonitrile in 200 ml THF. Stirred 15 minutes and added a solution of 17.99 g (64.2 mmol) methyl 4-ethoxy-5-methoxy-2-(dimethylaminomethyleneamino)benzoate in 150 ml THF dropwise over 20 minutes. Let stir for 0.5 hour at −78° C. Added 11.0 ml (193 mmol) acetic acid and warmed gradually to 25° C. After 2.5 hours, stripped solvent, slurried residue with water, collected solids and dried in vacuo, giving 13.025 g of yellow solid: mass spectrum (electrospray m/e): M+H=245.2.

EXAMPLE 180

Methyl 4-Ethoxy-5-methoxy-2-(dimethylaminomethyleneamino)benzoate

A mixture of 15.056 g (66.9 mmol) methyl 2-amino-4-ethoxy-5-methoxybenzoate and 14.1 ml (100 mmol) N,N-dimethylformamide dimethylacetal was heated to 100° C. under $N_2$. At 4.5 hours added 4.7 ml (33.3 mmol) more DMF/DMA and removed heat at 5 hours. Stripped solvent, azeotroped with toluene, and dried in vacuo, giving 18.211 g of grey-brown solid: mass spectrum (electrospray m/e): M+H=281.3.

EXAMPLE 181

Methyl 2-Amino-4-ethoxy-5-methoxybenzoate

A mixture of 24.110 g (94.5 mmol) methyl 4-ethoxy-5-methoxy-2-nitrobenzoate, 15.81 g (283 mmol) iron powder, 25.28 g (472 mmol) ammonium chloride, 135 ml water, and 350 ml methanol was heated to reflux under $N_2$. At both 3 and 5.5 hours added the same amount of iron and ammonium chloride. Removed heat at 6.5 hours, added ethyl acetate and saturated sodium bicarbonate, filtered through celite and separated layers. Washed organic layer with saturated sodium bicarbonate, dried with magnesium sulfate, stripped solvent, and dried in vacuo, giving 17.594 g of pink solid: : mass spectrum (electrospray m/e): M+H= 226.2.

EXAMPLE 182

Methyl 4-Ethoxy-5-methoxy-2-nitrobenzoate

Dissolved 5.00 g (23.7 mmol) methyl 4-ethoxy-3-methoxybenzoate in 25 ml acetic acid under $N_2$ and added 6.1 ml (95.1 mmol) 69% nitric acid dropwise over 30 minutes. Heated to 50° C. for 1.5 hours and poured onto ice bath. Extracted with chloroform, washed with dilute sodium hydroxide solution and filtered through magnesium sulfate. Stripped solvent and dried in vacuo, giving 5.268 of off-white solid: mass spectrum (electrospray m/e): M+H=255.8.

EXAMPLE 183

Methyl 4-Ethoxy-3-methoxybenzoate

A mixture of 25.0 g (137 mmol) methyl vanillate, 38.87 g (274 mmol) potassium carbonate, 500 ml DMF, and 16.5 ml (206 mmol) ethyl iodide was heated to 100° C. under $N_2$. At 2.5 hours, cooled and removed solids. Stripped solvent, and partitioned between water and methylene chloride. Stripped solvent and dried in vacuo, giving 25.85 g of white solid: mass spectrum (EI m/e): M=210.0.

EXAMPLE 184

N-[4-[(3-Chloro-4-fluorophenyl)amino]-3-cyano-6-quinolinyl]-4-dimethylamino-(Z)-2-butenamide A mixture of 0.05 g (0.118 mmol) N-[4-[(3-chloro-4-fluorophenyl)amino]-3-cyano-6-quinolinyl]-4-dimethylamino-2-butynamide and 6 mg of Lindlar catalyst in 10 mL of methanol was hydrogenated at room temperature overnight. The mixture was filtered through a pad of Celite. After the solvent was removed, the residue was purified by thin-layer chromatography eluted with 30% methanol in ethyl acetate. The product was dried to give 0.018 g (36%) pale yellow solid; HRMS m/z 423.1270 (M.).

EXAMPLE 185

N-{4-[(3-Chloro-4-fluorophenyl)amino]-3-cyano-6-quinolinyl}-4-methoxy-(Z)-2-butenamide A mixture of 0.05 g (0.1 18 mmol) N-{4-[(3-chloro-4-fluorophenyl)amino]-3-cyano-6-quinolinyl}-4-methoxy-2-butynamide and 6 mg of Lindlar catalyst in 15 mL of methanol was hydrogenated at room temperature for 5.5 hrs. The mixture was filtered through a pad of Celite. The solvent was removed to give 0.05 g (99.7%) yellow solid; HRMS m/z 410.0928 (M+.).

EXAMPLE 186

4-[[4-[(3-Bromophenyl)amino]-3-cyano-6-quinolinyl]-amino]-2-methylene-4-oxo-butanoic Acid Itaconic anhydride (0.1 4 g, 1.25 mmol) was added portionwise to a solution of 0.1 g (0.30 mmol) of 6-amino- 4-[(3-bromophenyl)amino]-3-quinolinecarbonitrile in 2 mL of ethyl acetate under N$_2$. After stirring at room temperature overnight, the reaction solution was added into ice water and hexane. The product was collected, washed with water, ether and hexane, and dried in vacuo to give 0.09 g (68%) of yellowish brown solid; ESMS m/z 451.2 (M+H$^+$).

EXAMPLE 187

N-[4-[(3-Bromophenyl)amino]-3-cyano-6-quinolinyl]-4-diethylamino-2-butynamide Isobutyl chloroformate (0.261 g, 1.91 mmol) was dropwise added into an ice cold solution of 4-diethylamino-2-butynoic acid (0.456 g, 2.94 mmol) and N-methylmorpholine (0.294 g, 2.94 mmol) in 50 mL of tetrahydrofuran under N$_2$. After stirring for 30 min, a solution of 0.5 g (1.47 mmol) of 6-amino-4-[(3-bromophenyl)amino]-3-quinolinecarbonitrile in 3 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.2 g (28.5%) of pale greenish yellow solid; ESMS m/z 476.2, 478.2 (M+H$^+$); mp 133–135° C.

EXAMPLE 188

N-[4-[(3-Bromophenyl)amino]-3-cyano-6-quinolinyl]-4-(N-ethylpiperazino)-2-butynamide Isobutyl chloroformate (0.785 g, 5.75 mmol) was dropwise added into an ice cold solution of 4-(N-ethylpiperazino)-2-butynoic acid (1.75 g, 8.85 mmol) and N-methylmorpholine (1.3453 g, 13.3 mmol) in 50 mL of tetrahydrofuran under N$_2$. After stirring for 30 min, a solution of 1.5 g (4.42 mmol) of 6-amino-4-[(3-bromophenyl)amino]-3-quinolinecarbonitrile in 10 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 1.07 g (46%) of light brown solid; ESMS m/z 517.1, 519.1 (M+H$^+$); mp 161° C. (dec).

EXAMPLE 189

N-[4-[(3-Chloro-4-fluorophenyl)amino]-3-cyano-6-quinolinyl]-4-diethylamino-2-butynamide Isobutyl chloroformate (0.061 g, 0.448 mmol) was dropwise added into an ice cold solution of 4-diethylamino-2-butynoic acid (0.104 g, 0.672 mmol) and N-methylmorpholine (0.068 g, 0.672 mmol) in 10 mL of tetrahydrofuran under N$_2$. After stirring for 30 min, a solution of 0.1 g (0.32 mmol) of 6-amino-4-[(3-chloro-4-fluorophenyl)amino]-3-quinolinecarbonitrile in 1.5 mL of pyridine was added dropwise and the mixture was stirred at 0° C. for 1.5 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected and dried in vacuo to give 0.046 g (32%) of light brown solid; ESMS m/z 450.2, (M+H$^+$); mp 117–120° C.

EXAMPLE 190

N-[4-[(3-Bromophenyl)amino]-3-cyano-6-quinolinyl]-4-(N-methylpiperazino)-2-butynamide Isobutyl chloroformate (0.785 g, 5.75 mmol) was dropwise added into an ice cold solution of 4-(N-methylpiperazino)-2-butynoic acid (1.65 g, 8.85 mmol) and N-methylmorpholine (1.3 6 g, 13.3 mmol) in 10 mL of tetrahydrofuran under N$_2$. After stirring for 30min, a solution of 1.5 g (4.42mmol) of 6-amino-4-[(3-bromophenyl)amino]-3-quinolinecarbonitrile in 10 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.37 (16%) of yellow solid; ESMS m/z 503, 505, (M+H$^+$); mp 190° C. (dec).

EXAMPLE 191

N-[4-[(3-Bromophenyl)amino]-3-cyano-6-quinolinyl]-4-(N-isopropyl-N-methylamino)-2-butynamide Isobutyl chloroformate (0.785 g, 5.75 mmol) was dropwise added into an ice cold solution of 4-(N-isopropyl-N-methylamino)-2-butynoic acid (1.4 g, 8.84 mmol) and N-methylmorpholine (0.94 g, 9.3 mmol) in 80 mL of tetrahydrofuran under N$_2$. After stirring for 30 min, a solution of 1.5 g (4.42 mmol) of 6-amino-4-[(3-bromophenyl)amino]-3-quinolinecarbonitrile in 15 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.65 (31%) of reddish brown solid; ESMS m/z 476.0, 478.0 (M+H$^+$); mp 124–126° C.

EXAMPLE 192

N-[4-[(3-Bromophenyl)amino]-3-cyano-6-quinolinyl]-4-diisopropylamino-2-butynamide Isobutyl chloroformate (0.785 g, 5.75 mmol) was dropwise added into an ice cold solution of 4-diisopropylamino)-2-butynoic acid (1.65 g, 8.85 mmol) and N-methylmorpholine (0.94 g, 9.3 mmol) in 100 mL of tetrahydrofuran under N$_2$. After stirring for 30 min, a solution of 1.5 g (4.42 mmol) of 6-amino-4-[(3-bromophenyl)amino]-3-quinolinecarbonitrile in 15 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 1.08 (48%) of light brown solid; ESMS m/z 504.1, 506.1 (M+H$^+$); mp 130° C. (dec).

EXAMPLE 193

N-[4-[(3-Chloro-4-fluorophenyl)amino]-3-cyano-6-quinolinyl]-4-dimethylamino-2-butynamide Isobutyl chloroformate (0.85 g, 6.2 mmol) was dropwise added into an ice cold solution of 4-dimethylamino-2- butynoic acid (1.85 g, 14.4 mmol) and N-methylmorpholine (1.5 g, 14.8 mmol) in 100 mL of tetrahydrofuran under $N_2$. After stirring for 30 min, a solution of 1.5 g (4.79 mmol) of 6-amino-4-[(3-chloro-4-fluorophenyl)amino]-3-quinolinecarbonitrile in 15 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.47 (23%) of reddish brown solid; ESMS m/z 422.0 (M+H$^+$); mp 225° C. (dec).

EXAMPLE 194

N-[4-[-(3-Chloro-4-fluorophenyl)amino]-3-cyano-6-quinolinyl]-4-methoxy-2-butynamide Isobutyl chloroformate (0.85 g, 6.2 mmol) was dropwise added into an ice cold solution of 4-methoxy-2-butynoic acid (1.1 g, 9.6 mmol) and N-methylmorpholine (1.02 g, 10 mmol) in 100 mL of tetrahydrofuran under $N_2$. After stirring for 30 min, a solution of 1.5 g (4.79 mmol) of 6-amino-4-[(3-chloro-4-fluorophenyl)amino]-3-quinolinecarbonitrile in 15 mL of pyridine was added dropwise and the mixture was stirred at 0° C. for 3 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.73 (37%) of light yellowish brown solid; ESMS m/z 409(M+H$^+$); mp 170–171).

EXAMPLE 195

4-[(3-Bromo-4-fluorophenyl)amino]-6-nitro-3-quinolinecarbonitrile

A mixture of 3.8 g (16.33 mmol) of 4-chloro-6-nitro-3-quinolinecarbonitrile and 3.7 g (20 mmol) of 3-bromo-4-fluoroaniline in 200 mL of ethanol was refluxed for 3 hr. After the solvent was removed, the residue as dissolved in ethyl acetate and washed with sodium bicarbonate. The product was collected as a pale yellow solid, 6.5 g (71%); ESMS m/z 387.3, 389.2, mp 269–270° C. (dec).

EXAMPLE 196

6-amino-4-[(3-Bromo-4-fluorophenyl)amino]-3-quinolinecarbonitrile

A mixture of 8 g (20.67 mmol) of 4-[(3-chloro-4-fluorophenyl)amino]-6-nitro-3-quinolinecarbonitrile, 4 g (72.35 mmol) of iron dust and 8.9 g (165.36 mmol) of ammonium chloride in 240 mL of methanol and water (2:1 ratio) was refluxed for 4 hr. The mixture was filtered hot and washed with methanol and water. The product precipitated from the filtrate upon cooling. The solid was collected and dried in vacuo to give 5.8 g (79%) yellowish brown solid; ESMS m/z 356.8, 358.8, mp 210–212° C.

EXAMPLE 197

N-[4-[(3-Bromo-4-fluorophenyl)amino]-3-cyano-6-quinolinyl]-4-dimethylamino-2-butynamide Isobutyl chloroformate (0.373 g, 2.73 mmol) was dropwise added into an ice cold solution of 4-dimethylamino-2-butynoic acid (0.8 g, 6.3mmol) and N-methyl-Imorpholine (0.658 g, 6.5 mmol) in 80 mL of tetrahydrofuran under $N_2$. After stirring for 30 min, a solution of 10.65 g (2.1 mmol) of 6-amino-4-[(3-bromo-4-fluorophenyl)amino]-3-quinolinecarbonitrile in 10 mL of pyridine was added dropwise and the mixture was stirred at 0° C. for 2.5 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.33 (33%) of yellow solid; ESMS m/z 465.9, 467.9(M+H$^+$); mp 228–231° C.

EXAMPLE 198

4-Dimethylamino-but-2-enoic acid [4-(3-bromo-phenylamino)-3-cyano-7-methoxy-quinolin-6-yl]-amide To a mixture of 1.9 g (5.1 mmol) of 4-[(3-bromophenyl)amino]-7-methoxy-6-amino-3-quinolinecarbonitrile and 5.3 ml (31 mmol) of Hunig's base in 110 ml of dry THF at 0° C., with stirring, was added a THF solution containing 5.7 g (31 mmol) of 4-bromo crotonyl chloride dropwise. The mixture was stirred for additional 0.5 hour after addition. 100 ml of saturated sodium chloride solution was added to the reaction mixture, then it was extracted with ethyl acetate. The ethyl acetate solution was dried over sodium sulfate and then was added to 40 ml of dimethyl amine solution (2.0 M in THF) at 0° C. dropwise. The solution was stirred an additional 0.5 hour. The mixture was poured into diluted sodium bicarbonate solution . The organic layer was separated and dried over sodium sulfate. Chromatography gave 1.4 g of beige solid: mass spectrum (electrospray, m/e): M+H 480.0 and 481.9.

EXAMPLE 199

4-Diethylamino-but-2-enoic acid [4-(3-bromo-phenylamino)-3-cyano-7-methoxy-quinolin-6-yl]-amide To a mixture of 0.5 g (1.36 mmol) of 4-[(3-bromophenyl)amino]-7-methoxy-6-amino-3-quinolinecarbonitrile and 0.48 ml (2.7 mmol) of Hunig's base in 50 ml of dry THF at 0° C., with stirring, was added a THF solution containing 0.50 g (2.7 mmol) of 4-bromo crotonyl chloride dropwise. The mixture was stirred for additional 0.5 hour after addition and then was added to a solution of 4.2 ml (40.8 mmol) diethyl amine in 50 ml of THF at 0° C. dropwise. The solution was stirred for an additional 0.5 hour. The mixture was poured into diluted sodium bicarbonate solution . The organic layer was separated and dried over sodium sulfate. Chromatography gave 0.2 g of white solid: mass spectrum (electrospray, m/e): M+H 508.1 and 510.8.

EXAMPLE 200

4-Morpholin-4-yl-but-2-enoic acid [4-(3-bromo-phenylamino)-3-cyano-7-methoxy-quinolin-6-yl]-amide To a mixture of 0.69 g (1.87 mmol) of 4-[(3-bromophenyl)amino]-7-methoxy-6-amino-3-quinolinecarbonitrile and 0.98 ml (5.6 mmol) of Hunig's base in 50 ml of dry THF at 0° C., with stirring, was added a THF solution containing 0.86 g (5 mmol) of 4-bromocrotonyl chloride dropwise. The mixture was stirred for a additional 0.5 hour and then was added to a solution of 4.89 ml (56 mmol) morpholine in 50 ml THF at 0° C. dropwise. The solution was stirred an additional 0.5 hour and then the mixture was poured into diluted sodium bicarbonate solution . The organic layer was separated and dried over sodium sulfate. The residue was chromatographed to give 0.38 g of grey solid: mass spectrum (electrospray, m/e): M+H 521.9 and 523.8.

EXAMPLE 201

4-(3-Chloro-4-fluoro-phenylamino)-7-methoxy-6-nitro-quinoline-3-carbonitrile

A mixture of 4.4 g (16.7 mmol) of 4-chloro-7-methoxy-6-nitro-3-quinolinecarbonitrile and 2.67 g (18.3 mmol) of 3-chloro-4-fluoro aniline in 110 ml of methoxyethanol was refluxed under nitrogen for 4 hours. The reaction mixture was diluted with ethyl acetate and wash with sodium bicarbonate solution and sodium chloride solution. The organic layer was dried over sodium sulfate and then the solvent was removed under vacuum. The residue was chromatographed on silica gel eluting with mixture of ethyl acetate and methanol to give 3 g yellow solid: mass spectrum (electrospray, m/e): 372.9.

EXAMPLE 202

6-Amino-4-(3-chloro-4-fluoro-phenylamino)-7-methoxy-quinoline-3-carbonitrile

A mixture of 4.88 g (13 mmol) of 4-[(3-chloro-4-fluorophenyl)amino]-7-methoxy-6-nitro-quinoline-3-carbonitrile, 5.2 g (97.5 mmol) of ammonium chloride, and 3.3 g (58.5 mmol) iron was stirred at reflux in 60 ml of water and 60 ml of methanol for 4.5 hours. The mixture was diluted with 500 ml of hot ethyl acetate and the hot mixture was filtered. The filtration was washed with saturated sodium chloride solution and then the organic layer was dried over sodium sulfate. The solvent was removed and the residue was chromatographed on silica gel eluting with mixture of ethyl acetate and methanol to give 3.38 g of yellow solid: mass spectrum (electrospray, m/e): M+H 343.4.

EXAMPLE 203

4-Dimethylamino-but-2-enoic acid [4-(3-chloro-4-fluoro-phenylamino)-3-cyano-7-methoxy-quinolin-6-yl]-amide To a mixture of 1.08 g (3.1 mmol) of 4-[(3-chloro-4-fluorophenyl)amino]-7-methoxy-6-amino-quinoline-3-carbonitrile and 1.7 ml (9.7 mmol) of Hunig's base in 30 ml of dry THF at 0° C., with stirring, was added a THF solution containing 1.99 g (9.3 mmol) of 4-bromo crotonyl chloride dropwise. The mixture was stirred for additional 0.5 hour at 0° C. under nitrogen. 50 ml of saturated sodium chloride solution was introduced to the reaction mixture, then it was extracted with ethyl acetate. The ethyl acetate solution was separated and dried over sodium sulfate and then it was added to 31 ml of dimethyl amine solution (2.0 M in THF) at 0° C. dropwise. After addition, the solution was stirred for another hour at room temperature. The mixture was poured into diluted sodium bicarbonate solution . The organic layer was separated and the residue was chromatographed to give 0.86 grams of white solid: mass spectrum (electrospray, m/e).

EXAMPLE 204

4-Diethylamino-but-2-enoic acid [4-(3-chloro-4-fluoro-phenylamino)-3-cyano-7-methoxy-quinolin-6-yl]-amide To a mixture of 1.1 g (3.2 mmol) of 4-[3-chloro-4-fluorophenyl)amino]-7-methoxy-6-amino-3-quinolinecarbonitrile and 2.24 ml (12.8 mmol) of Hunig's base in 40 ml of dry THF at 0° C., with stirring, was added a THF solution containing 2.34 g (12.8 mmol) of 4-bromo crotonyl chloride dropwise. The mixture was stirred for additional 0.5 hour at 0° C. 50 ml of saturated sodium chloride solution was added to the reaction mixture and then it was extracted with ethyl acetate. The ethyl acetate solution was dried over sodium sulfate and added to a solution of 6.6 ml (64 mmol) diethyl amine in 5 ml of THF at 0° C. dropwise. The solution was stirred an additional hour at 0° C. The mixture was poured into diluted sodium bicarbonate solution . The organic layer was separated and dried over sodium sulfate. The residue was chromatographed and followed by recrystallization to give 0.62 grams of white solid: mass spectrum (electrospray, m/e): M+H 482.0.

EXAMPLE 205

4-Morpholin-4-yl-but-2-enoic acid [4-(3-chloro-4-fluoro-phenylamino)-3-cyano-7-methoxy-quinolin-6-yl]-amide To a mixture of 1.2 g (3.5 mmol) of 4-[(3-chloro-4-fluorophenyl)amino]-7-methoxy-6-amino-quinoline-3-carbonitrile and 2.44 ml (14 mmol) of Hunig's base in 50 ml of dry THF at 0° C., with stirring, was added a THF solution containing 2.57 g (14 mmol) of 4-bromo crotonyl chloride dropwise. The mixture was stirred for an additional hour at 0° C. 50 ml of saturated sodium chloride solution was added to the reaction mixture, then it was extracted with ethyl acetate. The ethyl acetate solution was dried over sodium sulfate and then was added to a solution of 4.58 ml (52.5 mmol) morpholine in 5 mL of THF at 0° C. dropwise. The solution was stirred an overnight at 0° C. The mixture was poured into diluted sodium bicarbonate solution . The organic layer dried over sodium sulfate. Chromatography gave 0.83 grams off-white solid: mass spectrum (electrospray, m/e): M+H 496.0.

EXAMPLE 206

4-(3-Bromo-4-fluoro-phenylamino)-7-methoxy-6-nitro-quinoline-3-carbonitrile

A mixture of 3.52 g (9.7 mmol) of 4-chloro-7-methoxy-6-nitro-3-quinolinecarbonitrile and 2.0 g (10.7 mmol) of 3-bromo-4-fluoro aniline in 150 ml of methoxyethanol was refluxed under nitrogen for 5.5 hours. The reaction mixture was diluted with ethyl acetate and wash with sodium bicarbonate solution and sodium chloride solution. The organic layer was dried with sodium sulfate and then solvent was removed under vacuum. The residue was chromatographed on silica gel eluting with mixture of ethyl acetate and methanol to give 3 g of yellow solid: mass spectrum (electrospray, m/e): 416.8 and 418.8.

EXAMPLE 207

6-Amino-4-(3-bromo-4-fluoro-phenylamino)-7-methoxy-quinoline-3-carbonitrile

A mixture of 2.9 g (6.95 mmol) of 4-[(3-bromo-4-fluorophenyl)amino]7-methoxy-6-nitro-quinoline-3-carbonitrile, 6.5 g (121.6 mmol) of ammonium chloride and 4.05 g (73 mmol) of iron in 50 ml of water and 50 ml of methanol for 6 hours. The mixture was diluted with hot ethyl acetate and the hot mixture was filtered. The filtration was washed with saturated sodium chloride solution then the organic layer was dried over sodium sulfate. The solvent was removed and the residue was chromatographed on silica gel eluting with mixture of ethyl acetate and methanol to give 2.11 g of light yellow solid: mass spectrum (electrospray, m/e): M+H 386.7 and 388.8.

EXAMPLE 208

4-Dimethylamino-but-2-enoic acid [4-(3-bromo-4-fluoro-phenylamino)-3-cyano-7-methoxy-quinolin-6-yl]-amide To a mixture of 0.77 g (1.98 mmol) of 4-(3-bromo-4-fluorophenyl)amino]-7-methoxy-6-amino-quinoline-3-carbonitrile and 3.5 ml (20 mmol) of Hunig's base in 35 ml of dry THF at 0° C., with stirring, was added a THF solution containing 2.2 g (12 mmol) of 4-bromo crotonyl chloride dropwise. The mixture was stirred for additional 30 minutes at 0° C. 50 ml of saturated sodium chloride solution was added to the reaction mixture, then it was extracted with ethyl acetate. The ethyl acetate solution was dried over sodium sulfate and then was added to 15 ml of dimethyl amine (2.0 M in THF) at 0° C. dropwise. The solution was stirred an additional hour at room temperature. The mixture was poured into diluted sodium bicarbonate solution . The organic layer was dried over sodium sulfate and the solvent was removed under vacuum. The residue was chromatographed gave 0.55 g beige solid: mass spectrum (electrospray, m/e): M+H 498.0 and 500.0.

EXAMPLE 209

4-Diethylamino-but-2-enoic acid [4-(3-bromo-4-fluoro-phenylamino)-3-cyano-7-methoxy-quinolin-6-yl]-amide To a mixture of 0.77 g (1.98 mmol) of 4-[(3-bromo-4-fluorophenyl)amino]-7-methoxy-6-amino-quinoline-3-carbonitrile and 3.5 ml (20 mmol) of Hunig's base in 35 ml of dry THF at 0° C., with stirring, was added a THF solution containing 2.2 g (12 mmol) of 4-bromo crotonyl chloride dropwise. The mixture was stirred for additional 30 minutes at 0° C. 50 ml of saturated NaCl solution was added to the reaction mixture, then it was extracted with ethyl acetate. The ethyl acetate solution was dried over sodium sulfate and then was added to a solution of 3.1 ml (30 mmol) of diethyl amine in 5 ml of THF at 0° C. dropwise. The solution was stirred an additional hour at 0° C. and 30 minutes at room temperature. The mixture was poured into diluted sodium bicarbonate solution . The organic layer was dried over sodium sulfate and solvent was removed under vacuum. The residue was chromatographed to give 0.4 g off-white solid: mass spectrum (electrospray, m/e): M+H 525.9 and 527.9.

EXAMPLE 210

7-Ethoxy-4-hydroxy-quinoline-3-carbonitrile

A mixture of 10 g (73 mmol) of 3-ethoxy aniline and 12.3 g (73 mmol) of ethyl (ethoxymethylene) cyanoacetate was heated in 90 ml of Dowther at 140° C. for 7 hours. To this mixture was added 250 ml of Dowtherm. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 9.86 g of brown solid: mass spectrum (electrospray, m/e): M+H 214.7.

EXAMPLE 211

7-Ethoxy-4-hydroxy-6-nitro-quinoline-3-carbonitrile

To a suspension of 5 g (23 mmol) of 7-Ethoxy-4-hydroxy-quinoline-3-carbonitrile in 75 ml of trifluroacetic anhydride was added 5.5 g (69 mmol) of ammonium nitrate over a period of 6 hours at room temperature. Excess anhydride was removed at reduced pressure at 45° C. The residue was stirred with 300 ml of water. The solid was collected and treated with boiling ethanol to give 3.68 g of tin solid: mass spectrum (electrospray, m/e) M+H 259.8.

EXAMPLE 212

4-Chloro-7-ethoxy-6-nitro-quinoline-3-carbonitrile

A mixture of 3.45 g (13 mmol) of 7-Ethoxy-4-hydroxy-6-nitro-quinoline-3-carbonitrile, 5.55 g (26 mmol) of phosphorous pentachloride, and 10 ml of phosphorous oxychloride was refluxed for 3 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.1 g of beige solid: mass spectrum (electrospray, m/e) M+H 277.7.

EXAMPLE 213

4-(3-Bromo-phenylamino)-7-ethoxy-6-nitro-quinoline-3-carbonitrile

A mixture of 2.1 g (7.6 mmol) of 4-chloro-7-ethoxy-6-nitro-3-quinolinecarbonitrile and 0.91 ml (8.3 mmol) of 3-bromo aniline in 100 ml ethanol was refluxed under nitrogen for 4.5 hours. The reaction mixture was poured into diluted sodium bicarbonate solution. Ethanol was removed under vacuum. The mixture was diluted with ethyl acetate and the organic layer was separated and dried over sodium sulfate. The solution was concentrated and solid was collected and then washed with hexane. Upon drying, 2.6 g of yellow solid obtained: mass spectrum (electrospray, m/e) M+H 412.8 and 414.9.

EXAMPLE 214

6-Amino-4-(3-bromo-phenylamino)-7-ethoxy-quinoline-3-carbonitrile

A mixture of 2.5 g (6 mmol) of 4-[(3-bromophenyl) amino]-7-ethoxy-6-nitro-quinoline-3-carbonitrile, 2.4 g (45 mmol) of ammonium chloride, and 1.5 g (27 mmol) iron was stirred at reflux in 40 ml of water and 40 ml of methanol for 4 hours. The mixture was diluted with 500 ml of hot ethyl acetate and the hot mixture was filtered. The filtration was washed with saturated sodium chloride solution and then the organic layer was dried over sodium sulfate. The solution was concentrated and 1.5 of beige solid was collected: mass spectrum (electrospray, m/e): M+H 382.8 and 384.8.

EXAMPLE 215

4-Bromo-but-2-enoic acid [4-(3-bromo-phenylamino)-3-cyano-7-ethoxy-quinolin-6-yl]-amide To a mixture of 1.34 g (3.5 mmol) of 4-[3-bromo-phenyl) amino]-7-ethoxy-6-amino-3-quinolinecarbonitrile and 3.66 ml (21 mmol) of Hunig's base in 80 ml of dry THF at 0° C., with stirring, was added a THF solution containing 3.85 g (21 mmol) of 4-bromo crotonyl chloride dropwise. The mixture was stirred for additional 30 minutes at 0° C. 50 ml of saturated sodium chloride solution was added to the reaction mixture, then it was extracted with ethyl acetate. The ethyl acetate solution was dried over sodium sulfate and then the drying agent was filtered off. This solution was used without further characterization.

EXAMPLE 216

4-Dimethylamino-but-2-enoic acid [4-(3-bromo-phenylamino)-3-cyano-7-ethoxy-quinolin-6-yl]-amide A one-third portion of the solution from example 18 was added dropwise to 8.75 ml (17.5 mmol) of dimethyl amine at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.32 g beige solid: mass spectrum (electrospray, m/e) M+H, 494.0 and 496.0.

EXAMPLE 217

4-Diethylamino-but-2-enoic acid [4-(3-bromo-phenylamino)-3-cyano-7-ethoxy-quinolin-6-yl]-amide A one-third portion of the solution from example 18 was added dropwise to a solution of 1.81 ml (17.5 mmol) of diethyl amine in 5 ml of THF at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.22 g beige solid: mass spectrum (electrospray, m/e) M+H, 522.0 and 524.0.

EXAMPLE 218

4-Morpholin-4-yl-but-2-enoic acid [4-(3-bromo-phenylamino)-3-cyano-7-ethoxy-quinolin-6-yl]-amide A one-third portion of the solution from example 18 was added dropwise to a solution of 1.57 ml (18 mmol) of morpholine in 5 ml of THF at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.37 g white solid: mass spectrum (electrospray, m/e) M+H, 535.9 and 538.0.

EXAMPLE 219

8-Methoxy-4-hydroxy-6-nitro-quinoline-3-carbonitrile

A mixture of 12.6 g (75 mmol) of 2-methoxy-4-nitro aniline and 12.7 g (75 mmol) of ethyl (ethoxymethylene) cyanoacetate was heated in 100 ml of Dowther at 120° C. for overnight and 180° C. for 20 hours. To this mixture was added 300 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 12 g of brown solid: mass spectrum (electrospray, m/e): M+H 245.8.

EXAMPLE 220

4-Chloro-8-methoxy-6-nitro-quinoline-3-carbonitrile

A mixture of 4 g (16 mmol) of 8-Methoxy-4-hydroxy-6-nitro-quinoline-3-carbonitrile, 6.66 g (32 mmol) of phosphorous pentachloride, and 15 ml of phosphorous oxychloride was refluxed for 2.5 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.05 g of tan solid: mass spectrum (electrospray, am/e) M+H 263.7.

EXAMPLE 221

6-nitro-4-(3-bromo-phenylamino)-8-methoxy-quinoline-3-carbonitrile

A mixture of 1.9 g (7.6 mmol) of 4-chloro-8-methoxy-6-nitro-quinoline-3-carbonitrile and 0.86 ml (8.3 mmol) of 3-bromo aniline in 95 ml ethanol was refluxed under nitrogen for 5 hours. The reaction mixture was poured into diluted sodium bicarbonate solution. Ethanol was removed under vacuum. The mixture was diluted with ethyl acetate and the organic layer was separated and dried over sodium chloride. The solution was concentrated and solid was collected and then washed with hexane. Upon drying, 2.3 g of yellow solid obtained: mass spectrum (electrospray, m/e) M+H 398.8 and 400.8.

EXAMPLE 222

6-Amino-4-(3-bromo-phenylamino)-8-methoxy-quinoline-3-carbonitrile

A mixture of 2.15 g (5 mmol) of 4-[(3-bromophenyl)amino]-8-methoxy-6-nitro-quinoline-3-carbonitrile, 1.95 g (37.5 mmol) of ammonium chloride, and 1.26 g (22.5 mmol) iron was stirred at reflux in 40 ml of water and 40 ml of methanol for 3 hours. The mixture was diluted with 500 ml of hot ethyl acetate and the hot mixture was filtered. The filtration was washed with saturated sodium chloride solution and then the organic layer was dried over sodium sulfate. The solution was concentrated and 0.43 of dark yellow solid was collected: mass spectrum (electrospray, m/e): M+H 368.9 and 370.9.

EXAMPLE 223

4-Bromo-but-2-enoic acid [4-(3-bromo-phenylamino)-3-cyano-8-methoxy-quinolin-6-yl]-amide To a mixture of 1.05 g (2.8 mmol) of 4-[3-bromo-phenyl)amino]-8-methoxy-6-amino-3-quinolinecarbonitrile and 3.9 ml (22.4 mmol) of Hunig's base in 50 ml of dry THF at 0° C., with stirring, was added a THF solution containing 4.11 g (22.4 mmol) of 4-bromo crotonylchloride dropwise. The mixture was stirred for additional 1 hour at 0° C. 50 mL of saturated sodium chloride solution was added to the reaction mixture, then it was extracted with ethyl acetate. The ethyl acetate solution was dried over sodium sulfate and then the drying agent was filtered off. This solution was used without further characterization.

EXAMPLE 224 amino)-4-Dimethylamino-but-2-enoic acid [4-(3-bromo-phenylamino)-3-cyano-8-methoxy-quinolin-6-yl]-amide A one-third portion of the solution form example 26 was added dropwise to a solution of 7 ml (14 mmol) of dimethyl amine (2.0 M in THF) at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.22 g tin solid: mass spectrum (electrospray, m/e) M+H, 480.0 and 482.0.

EXAMPLE 225

4-Diethylamino-but-2-enoic acid [4-(3-bromo-phenylamino)-3-cyano-8-methoxy-quinolin-6-yl]-amide A one-third portion of the solution from example 26 was added dropwise to a solution of 1.4 ml (14 mmol) of diethyl amine in 5 ml of THF at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 95 mg tin solid: mass spectrum (electrospray, m/e) M+H, 509.9 and 511.0.

EXAMPLE 226

4-Morpholin-4-yl-but-2-enoic acid [4-(3-bromo-phenylamino)-3-cyano-8-methoxy-quinolin-6-yl]-amide A one-third portion of the solution from example 26 was added dropwise to a solution of 1.2 ml (14 mmol) of morpholine in 5 ml of THF at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.21 g yellow solid: mass spectrum (electrospray, m/e) M+H, 522.0 and 524.0.

EXAMPLE 227

4-Dimethylamino-but-2-ynoic acid [4-(3-bromo-phenylamino)-3-cyano-7-methoxy-guinol-6-yl]-amide Isobutyl chloroformate 6.9 ml (5.4 mmol) and N-methylmorpholine 1.19 ml (10.8 mmol) were added to an ice-cold solution of 1.37 g (10.8 mmol) of 4-dimethylamino-2-butynoic acid in 60 ml of THF. After stirring for 10 minutes, a solution of 1 g (2.7 mmol) 4-[(3-bromophenyl)amino]-7-methoxy-6-amino-quinoline-3-carbonitrile in 10 ml of pyridine was introduced. The reaction mixture was stirred overnight at 0° C. The solvent was evaporated and the residue was stirred in diluted sodium bicarbonate. The solution was then extracted with ethyl acetate. The ethyl acetate solution was dried and removed under vacuum. The residue was chromatographed to give 0.18 g of tin solid: mass spectrum (electrospray, m/e) 478.0 and 480.0.

EXAMPLE 228

4-(4-Chloro-2-fluoro-phenylamino)-6,7-dimethoxy-quinoline-3-carbonitrile

A mixture of 2.0 g of 4-chloro-6,7-dimethoxy-3-quinolinecarbonitrile, 1.46 g of 4-chloro-2-fluoroaniline, 0.925 g of pyridine hydrochloride, and 125 ml of ethoxy-ethanol was stirred under nitrogen, at reflux temperature for 1 h. The mixture was cooled and added to 1000 ml of water. To this mixture was added sodium carbonate to pH 9. The product was collected, washed with water, and dried to give 2.61 g of 4-(4-chloro-2-fluoro-phenylamino)-6,7-dimethoxy-quinoline-3-carbonitrile as a solid, mp 139–141° C.; mass spectrum (electrospray, m/e): M+H 357.9.

EXAMPLE 229

4-(3-Hydroxy-4-method-phepylamino)-6,7-dimethoxy-quinoline-3-carbonitrile

A mixture of 2.98 g of 4-chloro-6,7-dimethoxy-3-quinolinecarbonitrile, 1.85 g of 5-amino-o-cresol, 1.39 g of pyridine hydrochloride, and 200 ml of ethoxyethanol was stirred under nitrogen, at reflux temperature for 1 h. The mixture was cooled and added to 1000 ml of water. To this mixture was added sodium carbonate to pH 9. The product was collected, washed with water, and dried to give 3.27 g of 4-(3-hydroxy-4-methyl-phenylamino)-6,7-dimethoxy-quinoline-3-carbonitrile as a solid, mp 222–224° C.; mass spectrum (EI, m/e): M 335.1269.

EXAMPLE 230

4-Hydroxy-6,7,8-trimethoxy-quinoline-3-carbonitrile

A mixture of 4.82 g of methyl 3,4,5-trimethoxyanthranilate in 20 ml of N,N-dimethylformamide dimethyl acetal was refluxed for 18 hours and concentrated in vacuo. The crude amidine product was used in the next step without further purification.

To 25 ml of tetrahydrofuran at −78° C. was added 17.6 ml of 2.5M n-butyllithium in hexanes. Then 2.35 ml of aceto-nitrile in 45 ml of tetrahydrofuran was added dropwise. The mixture was stirred at −78° C. for 15 minutes. Then a solution of the crude amidine in 30 ml of tetrahydrofuran was added dropwise. The mixture was stirred at −78° C. for 30 minutes, then 5.7 ml of acetic acid was added. The mixture was warmed to room temperature, and 100 ml of water was added. The product was collected, washed with water, and dried to give 4.14 g of 4-hydroxy-6,7,8-trimethoxy-quinoline-3-carbonitrile as a solid, mp 280° C. (decomposed); mass spectrum (electrospray, m/e): M+H 261.2.

EXAMPLE 231

4-Chloro-6,7,8-trimethoxy-quinoline-3-carbonitrile

A stirred mixture of 1.30 g of 4-hydroxy-6,7,8-trimethoxy-quinoline-3-carbonitrile, 10 ml of phosphorous oxychloride, and 1 drop of N,N-dimethylformamide was refluxed for 10 minutes and evaporated free of volatile matter. The residue was stirred with 20 ml of 5% methyl alcohol in ethyl acetate. The product was collected and dried to give 1.12 g of 4-chloro-6,7,8-trimethoxy-quinoline-3-carbonitrile as a solid, mp 161–163° C.; mass spectrum (EI, m/e): M 278.0452.

EXAMPLE 232

4-(3-Dimethylamino-phenylamino)-6,7,8-trimethoxy-quinoline-3-carbonitrile

A mixture of 0.279 g of 4-chloro-6,7,8-trimethoxy-quinoline-3-carbonitrile, 0.23 g of N,N-dimethyl-1,3-phenylenediamine dihydrochloride, 0.2 ml of pyridine, and 15 ml of ethoxyethanol was stirred under nitrogen, at reflux temperature for 30 minutes. The mixture was cooled and added to 100 ml of water. To this mixture was added sodium carbonate to pH 9. The product was collected, washed with water, and dried to give 0.251 g of 4-(3-dimethylamino-phenylamino)-6,7,8-trimethoxy-quinoline-3-carbonitrile as a solid, mp 142–144° C.; mass spectrum (EI, m/e): M 378.1685.

EXAMPLE 233

4-(3-Hydroxy-4-methyl-phenylamino)-6,7,8-trimethoxy-quinoline-3-carbonitrile

A mixture of 0.279 g of 4-chloro-6,7,8-trimethoxy-quinoline-3-carbonitrile, 0.148 g of 5-amino-o-cresol, and 10 ml of ethoxyethanol was stirred under nitrogen, at reflux temperature for 30 minutes. The mixture was cooled and added to 100 ml of water. To this mixture was added sodium carbonate to pH 9. The product was collected, washed with water, and dried to give 0.279 g of 4-(3-hydroxy-4-methyl-phenylamino)-6,7,8-trimethoxy-quinoline-3-carbonitrile as a solid, mp 200° C. (decomposed); mass spectrum (EI, m/e): M 365.1356.

EXAMPLE 234

4-(4-Chloro-2-fluoro-phenylamino)-6,7,8-trimethoxy-quinoline-3-carbonitrile

A mixture of 0.279 g of 4-chloro-6,7,8trimethoxy-quinoline-3-carbonitrile, 0.177 g of 4-chloro-2-fluoroaniline, and 10 ml of ethoxyethanol was stirred under nitrogen, at reflux temperature for 30 minutes. The mixture was cooled and added to 100 ml of water. To this mixture was added sodium carbonate to pH 9. The product was extracted with ethyl acetate, washed with water, dried and concentrated in vacuo. The solid thus obtained was chromatographed on silica gel eluting with hexanes-ethyl acetate 9:1 to 2:1. Solvent was removed from product fractions giving 0.261 g of 4-(4-chloro-2-fluoro-phenylamino)-6,7,8-trimethoxy-quinoline-3-carbonitrile as a yellow solid: mp 166–168° C.; mass spectrum (EI, m/e): M 387.0777.

EXAMPLE 235

2-(Dimethylamino-methyleneamino)-3,6-dimethoxy-benzoic Acid Methylester

A mixture of 3.46 g of 2-amino-3,6-dimethoxybenzoic acid (Manouchehr Azadi-Ardakani and Timothy W. Wallace, Tetrahedron, Vol. 44, No. 18, pp. 5939 to 5952, 1988) in 20 ml of N,N-dimethylformaide dimethyl acetal was refluxed for 18 hours and concentrated in vacuo. To the residue was added 180 ml of ethyl acetate. The mixture was filtered, and 200 ml of hexanes was added to the filtrate. The mixture was then concentrated to 100 ml. The product was collected and dried to give 3.25 g of 2-(dimethylamino-methyleneamino)-3,6-dimethoxy-benzoic acid methylester as a solid, mp 81–83° C.; mass spectrum (EI, m/e): M 266.1263.

EXAMPLE 236

4-Hydroxy-5,8-dimethoxy-quinoline-3-carbonitrile

To 12.5 ml of tetrahydrofuran at −78° C. was added 8.8 ml of 2.5M n-butyllithium in hexanes. Then 1.18 ml of acetonitrile in 25 ml of tetrahydrofuran was added dropwise. The mixture was stirred at −78° C. for 15 minutes. Then a solution of 2-(dimethylamino-methyleneamino)-3,6-dimethoxy-benzoic acid methylester in 62 ml of tetrahydrofuran was added dropwise. The mixture was stirred at −78° C. for 10 minutes, then warmed to room temperature in 15 minutes. Acetic acid (3 ml) was added, followed by 200 ml of water. The product was collected, washed with water, and dried to give 1.57 g of 4-hydroxy-5,8-dimethoxy-quinoline-3-carbonitrile as a solid, mp 300–305° C.; mass spectrum (EI, m/e): M 230.0685.

EXAMPLE 237

4-Chloro-5 8-dimethoxy-quinoline-3-carbonitrile

A stirred mixture of 1.30 g of 4-hydroxy-5,8-dimethoxy-quinoline-3-carbonitrile, 10 ml of phosphorous oxychloride, and 2 drops of N,N-dimethylformamide was refluxed for 10 minutes and evaporated free of volatile matter. The residue was stirred with 50 ml of water. The product was collected and dried to give 1.74 g of 4-chloro-5,8-dimethoxy-quinoline-3-carbonitrile as a solid, mp 165–167° C.; mass spectrum (EI, m/e): M 248.0346.

EXAMPLE 238

4-(4-Chloro-2-fluoro-phenylamino)-5,8-dimethoxy-quinoline-3-carbonitrile

A mixture of 0.148 g of 4-chloro-5,8-dimethoxy-3-quinolinecarbonitrile, 0.102 g of 4-chloro-2-fluoroaniline, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.168 g of 4-(4-chloro-2-fluoro-phenylamino)-5,8-dimethoxy-quinoline-3-carbonitrile as a solid, mp 197–199° C.; mass spectrum (EI, m/e): M 329.7609.

EXAMPLE 239

4-(3-Hydroxy-4-methyl-phenylamino)-5,8-dimethoxy-quinoline-3-carbonitrile

A mixture of 0.148 g of 4-chloro-5,8-dimethoxy-3-quinolinecarbonitrile, 0.087 g of 5-amino-o-cresol, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.168 g of 4-(3-hydroxy-4-methyl-phenylamino)-5,8-dimethoxy-quinoline-3-carbonitrile as a solid, mp 240–242° C.; mass spectrum (EI, m/e): M 335.1260.

EXAMPLE 240

4-(3-Bromo-phenylamino)-5,8-dimethoxy-quinoline-3-carbonitrile

A mixture of 0.148 g of 4-chloro-5,8-dimethoxy-3-quinolinecarbonitrile, 0.12 g of m-bromoaniline, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.213 g of 4-(3-bromo-phenylamino)-5,8-dimethoxy-quinoline-3-carbonitrile as a solid, mp 72–74° C.; mass spectrum (EI, m/e): M 383.0265.

EXAMPLE 241

4-(3-Bromo-phenylamino)-6,7,8-trimethoxy-quinoline-3-carbonitrile

A mixture of 0.167 g of 4-chloro-6,7,8-trimethoxy-3-quinolinecarbonitrile, 0.12 g of m-bromoaniline, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.212 g of 4-(3-bromo-phenylamino)-6,7,8-trimethoxy-quinoline-3-carbonitrile as a solid, mp 211–213° C.; mass spectrum (EI, m/e): M 413.0377.

EXAMPLE 242

4-(3-Dimethylamino-phenylamino)-5,8-dimethoxy-quinoline-3-carbonitrile

A mixture of 0.148 g of 4-chloro-5,8-dimethoxy-3-quinolinecarbonitrile, 0.146 g of N,N-dimethyl-1,3-phenylenediamine dihydrochloride, 0.2 ml of pyridine, and 5 ml of ethoxyethanol was stirred under nitrogen, at reflux temperature for 30 minutes. Then the mixture was partitioned between ethyl acetate and saturated sodium chloride solution. The organic layer was dried and concentrated in vacuo. The residue thus obtained was chromatographed on silica gel eluting with ethyl acetate. Solvent was removed from product fractions giving 0.160 g of 4-(3-dimethylamino-phenylamino)-5,8-dimethoxy-quinoline-3-carbonitrile as a solid, mp 103–105° C.; mass spectrum (EI, m/e): M 348.1588.

EXAMPLE 243

4-(4-Chloro-2-fluoro-5-hydroxy-phenylamino)-5,8-dimethoxy-quinoline-3-carbonitrile A mixture of 0.223 g of 4-chloro-5,8-dimethoxy-3-quinolinecarbonitrile, 0.22 g of the methyl carbonate of 4-chloro-2-fluoro-5-hydroxy-aniline, and 15 ml of ethoxyethanol was stirred under nitrogen, at reflux temperature for 30 minutes. The mixture was cooled and added to 100 ml of water. To this mixture was added sodium carbonate to pH 9. The product was collected, washed with water, and dried.

The solids thus obtained were dissolved in a mixture of 30 ml of methyl alcohol and 20 ml of acetone. To this mixture was added 1.5 ml of 28–30% ammonium hydroxide solution. The mixture was heated at 50° C. for 30 minutes and concentrated. The product was collected, washed with ethyl acetate, and dried to give 0.237 g of 4-(4-chloro-2-fluoro-5-hydroxy-phenylamino)-5,8-dimethoxy-quinoline-3-carbonitrile as a solid, mp 240° C. (decomposed); mass spectrum (electrospray, m/e): M+H 373.9.

EXAMPLE 244

4-(4-Chloro-2-fluoro-5-hydroxy-phenylamino)-6,7,8-trimethoxy-quinoline-3-carbonitrile A mixture of 0.279 g of 4-chloro-6,7,8-trimethoxy-3-quinolinecarbonitrile, 0.22 g of the methyl carbonate of 4-chloro-2-fluoro-5-hydroxy-aniline, and 15 ml of ethoxyethanol was stirred under nitrogen, at reflux temperature for 30 minutes. The mixture was cooled and added to 100 ml of water. To this mixture was added sodium carbonate to pH 9. The product was collected, washed with water, and dried. The solids thus obtained were dissolved in a mixture of 30 ml of methyl alcohol and 20 ml of acetone. To this mixture was added 1.5 ml of 28–30% ammonium hydroxide solution. The mixture was heated at 50° C. for 30 minutes and concentrated. The product was collected, washed with ethyl acetate, and dried to give 0.162 g of 4-(4-chloro-2-fluoro-5-hydroxy-phenylamino)-6,7,8-trimethoxy-quinoline-3-carbonitrile as a solid, mp 223–225° C.; mass spectrum (EI, m/e): M 403.0731.

EXAMPLE 245

4-(3-Hydroxy-2-methyl-phenylamino)-6,7-dimethoxy-quinoline-3-carbonitrile

A mixture of 0.249 g of 4-chloro-6,7-dimethoxy-3-quinolinecarbonitrile, 0.123 g of 3-amino-o-cresol, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.174 g of 4-(3-hydroxy-2-methyl-phenylamino)-6,7-dimethoxy-quinoline-3-carbonitrile as a solid, mp 255–257° C.; mass spectrum (electrospray, m/e): M+H 335.9.

EXAMPLE 246

4-(2-Hydroxy-6-methyl-phenylamino)-6,7-dimethoxy-quinoline-3-carbonitrile

A mixture of 0.249 g of 4-chloro-6,7-dimethoxy-3-quinolinecarbonitrile, 0.123 g of 2-amino-m-cresol, 20 mg of pyridine hydrochloride, and 1 0 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.216 g of 4-(2-hydroxy-6-methyl-phenylamino)-6,7-dimethoxy-quinoline-3-carbonitrile as a solid, mp 245–247° C.; mass spectrum (electrospray, m/e): M+H 336.1363.

EXAMPLE 247

3-(3-Cyano-6,7-dimethoxy-quinolin-4-ylamino)-benzamide

A mixture of 0.249 g of 4-chloro-6,7-dimethoxy-3-quinolinecarbonitrile, 0.136 g of 3-aminobenzamide, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.321 g of 3-(3-cyano- 6,7-dimethoxy-quinolin-4-ylamino)-benzamide as a solid, mp 253–255° C.; mass spectrum (electrospray, m/e): M 349.1301.

EXAMPLE 248

4-(3-Bromo-4-methyl-phenylamino)-6,7-dimethoxy-quinoline-3-carbonitrile

A mixture of 0.249 g of 4-chloro-6,7-dimethoxy-3-quinolinecarbonitrile, 0.186 g of 3-bromo-4-methylaniline, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.286 g of 4-(3-bromo-4-methyl-phenylamino)-6,7-dimethoxy-quinoline-3-carbonitrile as a solid, mp 292–294° C.; mass spectrum (EI, m/e): M 397.0446.

EXAMPLE 249

4-(3-Chloro-4-hydroxy-phenylamino)-6,7-dimethoxy-quinoline-3-carbonitrile

A mixture of 0.249 g of 4-chloro-6,7-dimethoxy-3-quinolinecarbonitrile, 0.144 g of 4-amino-2-chlorophenol, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.256 g of 4-(3-chloro-4-hydroxy-phenylamino)-6,7-dimethoxy-quinoline-3-carbonitrile as a solid, mp 230–232° C.; mass spectrum (EI, m/e): M 355.0719.

EXAMPLE 250

6,7-Dimethoxy-4-(2-methylsulfal-phenylamino)-quinoline-3-carbonitrile

A mixture of 0.249 g of 4-chloro-6,7-dimethoxy-3-quinolinecarbonitrile, 0.139 g of 2-(methylmercapto)aniline, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.184 g of 6,7-dimethoxy- 4-(2-methylsulfanyl-phenylamino)-quinoline-3-carbonitrile as a solid, mp 245–247° C.; mass spectrum (EI, m/e): M 351.1051.

EXAMPLE 251

Methyl 2-(dimethylaminomethyleneamino)-4,5-diethoxybenzoate

To a stirred solution of methyl 2-amino-4,5-diethoxybenzoate (4.79 g, 20 mmol) in 20 ml of DMF at 0° C. was added phosphorous oxychloride (2.24 ml, 24 mmol) during 15 m. The mixture was warmed to 55° C. and stirred for 45 m. The resulting solution was diluted with methylene chloride, cooled to 0° C., and treated with 80 ml of pre-cooled N/1 sodium hydroxide during 5 m. The organic layer was separated and washed at 0° C. with with water. The solution was dried and concentrated to give an amber oil; NMR (CDCl$_3$) δ 3.00(s, Me$_2$N).

EXAMPLE 252

1,4-Dihydroquinoline-6,7-diethoxy-4-oxo-3-carbonitrile

To a stirred solution of n-butyllithium (17.6 ml of 2.5 M in hexane; 44 mmol) in 25 ml of THF at −78° C. was added a solution of acetonitrile (2.35 ml, 45 mmol) in 44 ml of THF during 10 m. After stirring at −78° C. for 15 m, the mixture was treated with a solution of ethyl 2-(dimethylaminomethyleneamino)-4,5-diethoxybenzoate (5.83 g, 19.8 mmol) in 30 ml of THF during 30 m. After 30 m at −78° C. the mixture was treated with 5.7 ml (100 mmol) of acetic acid and evaporated to dryness. The residue was stirred in water, and the resulting precipitate was filtered off, washed with water, and dried to give 4.01 g of off-white solid; NMR (DMSO-d$_6$) d 8.58(s, 2-H).

EXAMPLE 253

4-Chloro-6,7-diethoxy-3-quinolinecarbonitrile

In the manner of Example 115 treatment of 1,4-dihydroquinoline-6,7-diethoxy-4-oxo-3-carbonitrile with phosphorous oxychloride gave the title compound as a pink solid, mp 170–175° C.

EXAMPLE 254

4-[3-Chloro-4-(phenylthio)phenylamino]-6,7-diethoxy-3-quinolinecarbonitrile

In the manner of Example 105 reaction of 4-chloro-6,7-diethoxy-3-quinolinecarbonitrile with 3-chloro-4-(phenylthio)aniline gave the title compound as a tan solid, mp 88–94° C.

EXAMPLE 255

4-[3-Chloro-4-(phenylthio)phenylamino]-6,7-dimethoxy-3-quinolinecarbonitrile

In the manner of Example 105 reaction of 4-chloro-6,7-dimethoxy-3-quinolinecarbonitrile with 3-chloro-4-(phenylthio)aniline gave the title compound as a tan solid, mp 124–130° C.

EXAMPLE 256

4-(3-Chloro-4-fluorophenylamino)-6,7-diethoxy-3-quinolinecarbonitrile

In the manner of Example 105 reaction of 4-chloro-6,7-diethoxy-3-quinolinecarbonitrile with 3-chloro-4-fluoroaniline gave the title compound as an off-white solid, mp 194–198° C.

EXAMPLE 257

4-(3-Acetylphenylamino)-6,7-diethoxy-3-quinolinecarbonitrile

In the manner of Example 105 reaction of 4-chloro-6,7-diethoxy-3-quinolinecarbonitrile with 3-aminoacetophenone gave the title compound as an off-white solid, mp 191–194° C.

EXAMPLE 258

4-(N-Methylphenylamino)-6,7-diethoxy-3-quinolinecarbonitrile

In the manner of Example 105 reaction of 4-chloro-6,7-diethoxy-3-quinolinecarbonitrile with N-methylaniline gave the title compound as a tan solid, mp 153–155° C.

EXAMPLE 259

4-(Phenylamino)-6,7-diethoxy-3-quinolinecarbonitrile

In the manner of Example 105 reaction of 4-chloro-6,7-diethoxy-3-quinolinecarbonitrile with aniline gave the title compound as a tan solid, mp 168–170° C.

EXAMPLE 260

4-(4-Fluorophenylamino)-6,7-diethoxy-3-quinolinecarbonitrile

In the manner of Example 105 reaction of 4-chloro-6,7-diethoxy-3-quinolinecarbonitrile with 4-fluoroaniline gave the title compound as a tan solid, mp 177–181° C.

EXAMPLE 261

4-(4-Fluoro-2-methylphenylamino)-6,7-diethoxy-3-quinolinecarbonitrile

In the manner of Example 105 reaction of 4-chloro-6,7-diethoxy-3-quinolinecarbonitrile with 4-fluoro-3-methylaniline gave the title compound as a tan solid, mp 105–108° C.

EXAMPLE 262

4-(3-Chlorophenylamino)-6,7-diethoxy-3-quinolinecarbonitrile

In the manner of Example 105 reaction of 4-chloro-6,7-diethoxy-3-quinolinecarbonitrile with 4-fluoroaniline gave the title compound as a tan solid, mp 188–190° C.

EXAMPLE 263

4-(3-Fluorophenylamino)-6,7-diethoxy-3-quinolinecarbonitrile

In the manner of Example 105 reaction of 4-chloro-6,7-diethoxy-3-quinolinecarbonitrile with 3-fluoroaniline gave the title compound as a tan solid, mp 192–195° C.

EXAMPLE 264

4-(3-Aminophenylamino)-6,7-dimethoxy-3-quinolinecarbonitrile

A stirred mixture of 4-chloro-6,7-dimethoxy-3-quinolinecarbonitrile (3.73 g, 15 mmol), 1,3-diaminobenzene (4.86 g, 45 mmol), pyridine (1.21 ml, 15 mmol), and 45 ml of ethoxyethanol was refluxed for 30 m, cooled, and stirred with aqueous sodium bicarbonate. The resulting solid was filtered, washed with water, and dried. Recrystallization from ethanol gave a brown solid, mp 222–228° C.

EXAMPLE 265

4-(3-Acetamidophenylamino)-6,7-dimethoxy-3-quinolinecarbonitrile

To a stirred solution of 4-(3-aminophenylamino)-6,7-dimethoxy-3-quinolinecarbonitrile (0.96 g, 3.0 mmol) in 9.0 ml of acetic acid at 25° C. was added 0.85 ml (9.0 mmol) of acetic anhydride. After 2 h the solution was evaporated to dryness, and the residue was stirred with methanol. This solution was evaporated, and the residue was recrystallized from ethanol to give 0.50 g of amber solid, mp 147–150° C.

EXAMPLE 266

4-[3-(2-Butynoylamino)phenylamino)]-6,7-dimethoxy-3-quinolinecarbonitrile

Isobutyl chloroformate (0.26 ml, 2.0 mmol) and N-methylmorpholine (0.22 ml, 2.0 mmol) were added to an ice-cold solution of 2-butynoic acid (0.21 g, 2.5 mmol) in 8.5 ml of THF. After 10 m a suspension of 4-(3-aminophenylamino)-6,7-dimethoxy-3-quinolinecarbonitrile (0.32 g, 1.0 mmol) in 6.5 ml of THF was added, and the resulting mixture was stirred at 25° C. for 16 h and diluted with water. The resulting solid was filtered off, washed with water, dried, and recrystallized from methanol to give 0.12 g of off-white solid, mp 193–196° C.

EXAMPLE 267

4-[3-(Hydroxymethyl)phenylamino]-6,7-dimethoxn-3-quinolinecarbonitrile

A stirred mixture of 4-chloro-6,7-dimethoxy-3-quinolinecarbonitrile (7.46 g, 30 mmol), 3-aminobenzyl alcohol (7.39 g, 60 mmol), pyridine (2.43 ml, 30 mmol), and 90 ml of ethoxyethanol was refluxed for 5 h, cooled, and stirred with aqueous sodium bicarbonate. The resulting solid was filtered, washed with water, and dried. Recrystallization from methanol gave a brown solid, mp 250–255° C.

EXAMPLE 268

4-[3-(Chloromethyl)phenylamino]-6,7-dimethoxy-3-quinolinecarbonitrile

To 14 ml of DMF was added phosphorous trichloride (0.70 ml, 8.0 mmol) with stirring at 25–30° C. After 60 m, the mixture was cooled to 0° C., and a suspension of 4-[3-(hydroxymethyl)phenylamino]-6,7-dimethoxy-3-quinolinecarbonitrile (1.34 g, 4.0 mmol) in 6 ml of DMF was added. The mixture was warmed to 25° C., stirred 15 m, recooled in ice bath, and partitioned with methylene chloride-aqueous sodium bicarbonate. The organic layer was washed with water, dried, and concentrated to give 1.15 g of an amber solid; NMR (CDCl$_3$) δ 4.79(s, CH$_2$Cl).

EXAMPLE 269

4-[3-(Acetylthiomethyl)phenylamino]-6,7-dimethoxy-3-quinolinecarbonitrile

To a stirred solution of 4-[3-(chloromethyl)phenylamino]-6,7-dimethoxy-3-quinolinecarbonitrile (0.97 g, 2.7 mmol) in 5.4 ml of DMF was added potassium thioacetate (0.93 g, 8.1 mmol) at 25° C. After 30 m the mixture was partitioned with methylene chloride and water. The organic layer was washed with water, dried, and concentrated. The residue was recrystallized from ethyl acetate to give 0.43 g of yellow solid, mp 172–177° C.

EXAMPLE 270

4-[3-(Thiomethyl)phenylamino]-6,7-dimethoxy-3-quinolinecarbonitrile

A stirred mixture of 4-[3-(acetylthiomethyl)phenylamino]-6,7-dimethoxy-3-quinolinecarbonitrile (1.23 g, 3.13 mmol), 12.5 ml of concentrated ammonium hydroxide, 63 ml of ethanol, and 32 ml of DMF was heated at 85° C. for 2.5 h and then concentrated to dryness. The residue was partitioned with methylene chloride and water. The organic layer was washed with water, dried, and concentrated. The residue was subjected to chromatography on silica gel with methylene chloride-ethyl acetate-methanol to give an off-white solid; mass spectrum (electrospray, m/e) M+H 352.1.

EXAMPLE 271

2-(Dimethylamino-methyleneamino)-3-methoxy-benzoic acid methyl ester

A reaction mixture of 5.0 g (29.9 mmol) of 2-amino-3-methoxy-benzoic acid in 25.0 mL of DMF-DMA was heated at 100–105° C. for 2.5 hr, and then the solvent was removed to give a red-purple viscous oil. After standing in a refrigerator, the oil solidified to give 5.8 g of the product as a red-purple solid in 82.8% yield, mass spectrum (electrospray, m/e): M+H 236.9

EXAMPLE 272

1,4-Dihydro-8-methoxy-4-oxo-3-quinolinecarbonitrile

To 35.0 mL of THF was added 26.6 mL (66.4 mmol) of n-BuLi solution during 5 min at −78° C. To the stirred solution was added a solution of 3.55 mL (67.9 mmol) of CH₃CN in 65 mL of THF during 10 min which time the solution became white suspension, and then continued to stir for 15 min at −78° C. To the suspension was added a solution of 5.8 g (24.5 mmol) of 2-(Dimethylamino-methyleneamino)-3-methoxy-benzoic acid methyl ester in 45 mL of THF during 30 min, and then continued to stir 30 min at −78° C. during which time the mixture gradually became clear. The solution was quenched with 8.5 mL of HOAc. The resulting thick slurry was stirred and warmed to room temperature. After most of the solvent was evaporated, the residue was diluted with cold water. The separate solid was collected by filtration and washed with water. After drying in vacuo, this afforded 3.8 g of the product as an off white solid in 77.6% of yield, m.p. 270° C. (dec.), mass spectrum (electrospray, m/e): M+H 201.1

EXAMPLE 273

4-Chloro-8-methoxy -3-quinolinecarbonitrile

A mixture of 3.8 g (19 mmol) of 1,4-dihydro-8-methoxy-4-oxo-3-quinolinecarbonitrile and 40 mL of phosphorous oxochloride and 5 drops of DMF was refluxed for 0.5 hours. The mixture was evaporated to dryness and diluted with hexanes. The solid was collected and mixed with cold dilute sodium carbonate solution and extracted several times with ethyl acetate. The organic layer was dried over sodium sulfate and filtered through a pad of silica gel. Removal of the solvent gave 3.8 g of 4-chloro-8-methoxy -3-quinolinecarbonitrile as an off white solid in 91% yield, mass spectrum (electrospray, m/e): M+H 219.1.

EXAMPLE 274

4-[(3-Bromophenyl)amino]-8-methoxy-3-quinolinecarbonitrile

A solution of 328.0 mg (1.5 mmol) of 4-chloro-8-methoxy-3-quinolinecarbonitrile, 309.7 mg (1.8 mmol) of 3-bromoaniline and 173.3 mg (1.5 mmol) of pyridine hydrochloride in 15 ml of 2-ethoxyethanol was refluxed under nitrogen for 0.5 hours. The solvent was removed and the residue was diluted with water followed by neutralization to pH 7–8 with diluted sodium carbonate solution. The precipitate was collected and washed with ether and dried in vacuo to give 476.1 mg (89.6%) of the product as a yellow solid, m.p. 210–212° C.; mass spectrum (electrospray, m/e): M+H 353.8, 355.8.

EXAMPLE 275

4-(4-Chloro-2-fluoro-phenylamino)-8-methoxy-quinoline-3-carbonitrile

Using an analogous procedure to that described in Example 274. A reaction mixture of 328.0 mg (1.5 mmol) of 4-chloro-8-methoxy-3-quinolinecarbonitrile, 173.3 mg (1.5 mmol) of pyridine hydrochloride and 240.0 mg (1.7 mmol) of 2-fluoro-4-chloro-aniline in 15 mL of 2-ethoxyethanol was heated at 100° C. for 2 hr. After the work up, 431.3 mg (87.9%) of the product was obtained as an off white solid, m.p. 127° C. (dec.), mass spectrum (electrospray, m/e): M+H 327.8, 329.9.

EXAMPLE 276

4-(3-Hydroxy-4-methyl-phenylamino)-8-methoxy-quinoline-3-carbonitrile

Using an analogous procedure to that described in Example 274. A reaction mixture of 328.0 mg (1.5 mmol) of 4-chloro-8-methoxy -3-quinolinecarbonitrile, 173.3 mg (1.5 mmol) of pyridine hydrochloride and 203.2 mg (1.7 mmol) of 3-hydroxy-4-methyl-aniline in 15 mL of 2-ethoxyethanol was heated at 100° C. for 1.5 hr. After the work up, 407.7 mg (89.4%) of the product was obtained as a yellow solid, m.p. 148–150° C., mass spectrum (electrospray, m/e): M+H 306.9.

EXAMPLE 277

4-(3-Dimethylamino-phenylamino)-8-methoxy-quinoline-3-carbonitrile

Using an analogous procedure to that described in Example 274. A reaction mixture of 250.0 mg (1.1 mmol) of 4-chloro-8-methoxy-3-quinolinecarbonitrile, 273.3 mg (3.0 mmol) of pyridine and 261.4 mg (1.25 mmol) of 3-dimethylaminoaniline hydrochloride in 10 mL of 2-ethoxyethanol was heated at 100° C. for 1.5 hr. The work up gave 294.8 mg (73.4%) of the product as a deep greenish yellow solid, m.p. 222–225° C., mass spectrum (electrospray, m/e): M+H 319.0.

EXAMPLE 278

4-(4-Bromo-3-hydroxy-phenylamino)-8-methoxy-quinoline-3-carbonitrile

Using an analogous procedure to that described in Example 274. A reaction mixture of 250.0 mg (1.1 mmol) of 4-chloro-8-methoxy -3-quinolinecarbonitrile, 131.7 mg (1.1 mmol) of pyridine hydrochloride and 286.7 mg (1.3 mmol) of 4-bromo-3-hydroxy-aniline in 10 mL of 2-ethoxyethanol was heated at 100° C. for 1.5 hr. The work up gave 374.1 mg (88.6%) of the product as a pink solid, m.p. 146° C. (dec.), mass spectrum (electrospray, m/e): M+H 369.9.

EXAMPLE 279

4-(3-Hydroxy-4-methoxy-phenylamino)-8-methoxy-quinoline-3-carbonitrile

Using an analogous procedure to that described in Example 274. A reaction mixture of 200.0 mg (0.92 mmol) of 4-chloro-8-methoxy-3-quinolinecarbonitrile, 105.7 mg (0.92 mmol) of pyridine hydrochloride and 140.6 mg (1.0 mmol) of 5-amino-2-methoxy-phenol in 10 mL of 2-ethoxyethanol was heated at 100° C. for 2 hr. The work up gave 261.6 mg (89.0%) of the product as a deep yellow solid, m.p. 138–140° C. (dec.), mass spectrum (electrospray, m/e): M+H 321.9.

EXAMPLE 280

8-Methoxy-4-(2,4,6-trifluoro-phenylamino)-quinoline-3-carbonitrile

Using an analogous procedure to that described in Example 274. A reaction mixture of 200.0 mg (0.92 mmol) of 4-chloro-8-methoxy-3-quinolinecarbonitrile, 105.7 mg (0.92 mmol) of pyridine hydrochloride and 148.6 mg (1.0 mmol) of 2,4,6-trifluoro-aniline in 10 mL of 2-ethoxyethanol was heated at 100° C. for 2 hr. The work up gave 112.6 mg (37.4%) of the product as a yellow solid, m.p. 297° C. (dec.), mass spectrum (electrospray, m/e): M+H 330.0.

EXAMPLE 281

4-(3-Hydroxy-4-methyl-phenylamino)-7-methoxy-quinoline-3-carbonitrile

To a suspension of 200 mg (0.91 mmol) of 4-chloro-7-methoxy-3-quinolinecarbonitrile and 135.5 mg (1.10 mmol)

of 5-amino-o-cresol in 10 mL of 2-ethoxy ethanol was added 105.6 mg (0.91 mmol) of pyridine hydrochloride. The resulting reaction mixture was refluxed for 1 hr, and then the solvent was removed to give a residue. To the residue was added about 30 mL of water and neutralized to pH 7–8 by addition of diluted sodium carbonate solution. The precipitate was collected by filtration and washed with water and ether. After drying in vacuo, this afforded 277 mg (99%) of the product as a yellow solid, m.p.>250° C., mass (electrospray, m/e): M+H 305.9.

EXAMPLE 282

4-(4-Chloro-2-fluoro-5-hydroxy-phenylamino)-7-methoxy-quinoline-3-carbonitrile

The method of Example 281 was used with 218.6 mg (1.0 mmol) of 4-chloro-7-methoxy-3-quinolinecarbonitrile, 263.5 mg (1.2 mmol) of the aniline and 115.6 mg (1.0 mmol) of pyridine hydrochloride in 10 mL of 2-ethoxyethanol. This afforded a red oil residue. To the residue were added 10 mL of methanol and 1 mL of $NH_4OH$ (28–30%). The resulting mixture was heated at 50° C. for 30 min, and then the solvent was removed to give a residue. To the residue was added water. The separated solid was collected by filtration and washed with water and ether/ethyl acetate (1:1). After drying in vacuo, 142.1 mg (41.4%) of the product was obtained as a brown solid, m.p. 240° C. (dec.); mass (electrospray, m/e): M+H 343.9, 345.8.

EXAMPLE 283

4-(4-Chloro-2-fluoro-phenylamino)-6-methoxy-quinoline-3-carbonitrile

The method of Example 281 was used with 218.6 mg (1 mmol) of 4-chloro-6-methoxy-3-quinolinecarbonitrile, 174.7 mg (1.2 mmol) of 4-chloro- 2-fluoro-aniline and 115.6 mg (1 mmol ) of pyridine hydrochloride in 10 mL of 2-ethoxyethanol. This afforded 319.8 mg of the product as a yellow solid, m.p.>250° C., mass (electrospray, m/e): M+H 325.9, 327.9

EXAMPLE 284

4-(3-Hydroxy-4-methyl-phenylamino)-6-methoxy-quinoline-3-carbonitrile

To a suspension of 218.6 mg (1.0 mmol) of 4-chloro-6-methoxy-3-quinolinecarbonitrile and 147.8 mg (1.20 mmol) of 5-amino-o-cresol in 10 mL of 2-ethoxyethanol was added 115.6 mg (1.0 mmol) of pyridine hydrochloride. The resulting reaction mixture was refluxed for 1 hr, and then the solvent was removed to give a residue . To the residue was added about 30 mL of water and neutralized to pH 7–8 by addition of diluted sodium carbonate solution. The precipitate was collected by filtration and washed with water and ether. After drying in vacuo, this afforded 278.3 mg (91%) of the product as a yellow solid, m.p.>250° C. (dec.), mass (electrospray, m/e): M+H 305.9.

EXAMPLE 285

4-(4-Chloro-2-fluoro-5-hydroxy-phenylamino)-6-methoxy-quinoline3-carbonitrile

The method of Example 282 was used with 218.6 mg (1.0 mmol) of 4-chloro-6-methoxy-3-quinolinecarbonitrile and 263.5 mg (1.2 mmol) of the aniline (cat 800906) in 10 mL of 2-ethoxyethanol was added 115.6 mg (1.0 mmol) of pyridine hydrochloride. This afforded a dark oil residue. To the residue was added 10 mL Of methanol and 1 mL of $NH_4OH$ (28–30%). The resulting mixture was heated at 50° C. for 30 min, and then the solvent was removed and the residue was triturated with water and ether in an ice bath. The separated solid was filtered off and washed with water and ether. After drying in vacuo, 83.2 mg (24.2%) of the product was obtained as a light brown solid, m.p. 228–230° C., mass (electrospray, m/e): M+H 343.8, 345.8.

EXAMPLE 286

4-(3,5-Dichloro-4-hydroxy-phenylamino)-6,7-dimethoxy-quinoline-3-carbonitrile

A reaction mixture of 248.7 mg (1 mmol) of 4-chloro-6,7-dimethoxy-3-quinolinecarbonitrile, 213.6 mg (1.2 mmol) of 4-amino-2,6-dichlorophenol and 115.6 mg (1 mmol) of pyridine hydrochloride in 10 mL of 2-ethoxyethanol was refluxed under $N_2$ for 1 hr. After removal of the solvent, the residue was diluted with water and neutralized to pH 7–8 with diluted sodium carbonate solution. The precipitate was filtered and washed with water and ether/ ethyl acetate (1:1). After drying in vacuo this yielded 346.7 mg (88.8%) of the product as a yellow solid, m.p.>250° C., mass (electrospray, m/e): M+H 389.8, 391.8.

EXAMPLE 287

4-(2-Hydroxy-4-methyl-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 147.8 mg (1.2 mmol) of 6-amino-m-cresol to give 287.5 mg (85.8%) of the product as a light brown solid, m.p.>250° C., mass (electrospray, m/e): M+H 335.9.

EXAMPLE 288

4-(4-Hydroxy-3,5-dimethyl-phenylamino)-6,7-dimethoxy-quinoline-3-carbinitile

Using an analogous procedure to that described in Example 286, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 164.6 mg (1.2 mmol) of 4-amino-2,5-dimethylphenol to give 232.9 mg (66.7%) of the product as a light brown solid, m.p. 234–236° C., mass (electrospray, m/e): M+H 349.9.

EXAMPLE 289

4-(3-Cyano-6,7-dimethoxy-quinolin-4-ylamino)-benzamide

Using an analogous procedure to that described in Example 286, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 163.4 mg (1.2 mmol) of 4-amino-benzamide to give 255.7 mg (73.4%) of the product as a light yellow solid, m.p.>250° C., mass (electrospray, m/e): M+H 348.9.

EXAMPLE 290

4-(5-Chloro-2-hydroxy-phenylamino)-6,7-dimethoxy-quinoline-3-carbonitrile

Using an analogous procedure to that described in Example 286, 248.7 mg (1 mmol) of 4-chloro-6,7- dimethoxy-3-quinolinecarbonitrile in 15 mL of 2-ethoxyethanol and in the presence of 115.6 mg (1 mmol) of pyridine hydrochloride was reacted with 172.3 mg (1.2 mmol) of 2-amino-chlorophenol to give 326.4 mg (91.9%) of the product as a yellow solid, m.p.>250° C., mass (electrospray, m/e): M+H 355.8.

EXAMPLE 291

4-(3,5-Dibromo-4-hydroxy-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 320.3 mg (1.2 mmol) of 4-amino-2,6-dibromophenol to give 427.1 mg (89.2%) of the product as a gray solid, m.p.>250° C., mass (electrospray, m/e): M+H 479.7, 481.6.

EXAMPLE 292

4-(4-Hydroxy-2-methyl-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 147.8 mg (1.2 mmol) of 4-amino-m-cresol to give 304.6 mg (90.9%) of the product as a salmon solid, m.p.>250° C., mass (electrospray, m/e): M+H 335.9

EXAMPLE 293

6,7-Dimethoxy-4-(pyridin-3-ylamino)-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 112.9 mg (1.2 mmol) of 3-amino-pyridine to give 60.6 mg (19.8%) of the product as an orange solid, m.p. 231–233° C., mass (electrospray, m/e): M+H 306.8.

EXAMPLE 294

6.7-Dimethoxy-4-(3-methylsulfanyl-phenylamino)-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 167.1 mg (1.2 mmol) of 3-(methylthio)aniline to give 134.1 mg (38.2%) of the product as an off white solid, m.p.>250° C., mass (electrospray, m/e): M+H 351.9.

EXAMPLE 295

4-(2-Hydroxy-5-methyl-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile, in 15 mL of 2-ethoxyethanol and in the presence of 115.6 mg (1 mmol) of pyridine hydrochloride was reacted with 147.8 mg (1.2 mmol) of 2-amino-p-cresol to give 315.0 mg (94.0%) of the product as a yellow solid, m.p. 198–200° C., mass (electrospray, m/e): M+H 335.8.

EXAMPLE 296

4-(2-Chloro-4-hydroxy-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 270.1 mg (1.5 mmol) of 4-amino-3-chlorophenol to give 299.2 mg (84.3%) of the product as a light brown solid, m.p.>250° C., mass (electrospray, m/e): M+H 355.8, 357.8.

EXAMPLE 297

2-(3-Cyano-6,7-dimethoxy-quinolin-4-ylamino)-benzamide

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 177.0 mg (1.3 mmol) of anthranilamide to give 292.4 mg (84.0%) of the product as a deep yellow solid, m.p. 238–240.5° C., mass (electrospray, m/e): M+H 348.9.

EXAMPLE 298

6,7-Dimethoxy-4-(4-methylsulfanyl-2henalamino)-quinoline-3-carbonitrile

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 181.0 mg (1.3 mmol) of 4-(methylmercapto)aniline to give 334.1 mg (95.2%) of the product as a yellow solid, m.p. 235–237° C., mass (electrospray, m/e): M+H 351.9, 352.9, 353.8, 354.9.

EXAMPLE 299

4-[4-(2-Hydroxy-ethyl)-phenylamino]-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 178.3 mg (1.3 mmol) of 4-aminophenethyl alcohol to give 327.8 mg (93.9%) of the product as an off white yellow solid, m.p. 208–210° C., mass (electrospray, m/e): M+H 349.9.

EXAMPLE 300

4-(2,4-Dihydroxy-phenylamino)-6,7-dimethoxy-quinoline-3-carbonitrile

Using an analogous procedure to that described in Example 286, 248.7 mg (1 mmol) of 4-chloro-6,7- dimethoxy-3-quinolinecarbonitrile in 12 mL of 2-ethoxyethanol and in the presence of 115.6 mg (1 mmol) of pyridine hydrochloride was reacted with 210.0 mg (1.3 mmol) of 4-aminoresorcinol to give 330.4 mg (98.0%) of the product as a deep purple solid, m.p.>250° C., mass (electrospray, m/e): M+H 337.9.

EXAMPLE 301

4-[2-(2-Hydroxy-ethyl)-phenylamino]-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 178.3 mg (1.3 mmol) of 2-aminophenethyl alcohol to give 218.4 mg (64.4%) of the product as a pink solid, m.p 159–162° C., mass (electrospray, m/e): M+H 349.9.

EXAMPLE 302

4-(3-Bromophenylamino)-6,7-dihydroxy-3-quinolinecarbonitrile

A stirred mixture of 4-(3-bromophenylamino)-6,7-dimethoxy-3-quinolinecarbonitrile (15.4 g, 40 mmol) and 100 g of pyridine hydrochloride was heated at 210° C. for 20 m, cooled to 0° C., treated with 100 ml of concentrated ammonium hydroxide, and concentrated to dryness. The residue was stirred with 1 L of water, and the resulting amber solid was filtered off, washed with water, and dried; mass spectrum (electrospray, m/e) M+H 356.1, 358.1.

EXAMPLE 303

4-(3-Bromophenylamino)-6,7-di-n-pronoxy-3-quinolinecarbonitrile

To a stirred mixture of 4-(3-bromophenylamino)-6,7-dihydroxy-3-quinolinecarbonitrile (1.07 g, 3.0 mmol), potassium carbonate (1.66 g, 12.0 mmol), and 12 ml of DMF at 0° C. was added 1-iodopropane (1.17 ml, 12.0 mmol). The mixture was warmed to 25° C., stirred for 5 h, and then partioned at 0° C. with ethyl acetate and water containing HCl to give pH~8. The organic layer was separated, washed with water, dried, and concentrated. The residue was subjected to chromatography on silica gel with methylene chloride-ethyl acetate-acetic acid to give an amorphous solid; mass spectrum (electrospray, m/e) M+H 440.2, 442.2.

EXAMPLE 304

4-[(3-Bromopheyl)-N-acetylamino]-6,7-dihydroxy-3-quinolinecarbonitile

A solution of 4-(3-bromophenylamino)-6,7-dihydroxy-3-quinolinecarbonitrile (1.78 g, 5.0 mmol), dimethylaminopyridine (60 mg, 0.50 mmol), 5.0 ml of acetic anhydride, and 10 ml of pyridine was stirred at reflux temperature for 1.5 h and concentrated to dryness. The residue was stirred with 50 ml of methanol, 5 ml of water, and sodium bicarbonate (2.1 g, 25 mmol) at 25° C. for 16 h and concentrated to dryness. The residue was stirred with water containing acetic acid to give pH~4–5, and the resulting solid was filtered off, washed with water, and dried. A solution of the resulting solid in THF was passed through a pad of silica gel; the filtrate was concentrated to give a tan solid; mass spectrum (electrospray, m/e) M–H 396.3, 398.3.

EXAMPLE 305

4-(3-Bromophenylamino)-6,7-di-n-butoxy-3-quinolinecarbonitrile

A stirred mixture of 4-[(3-bromophenyl)-N-acetylamino]-6,7-dihydroxy-3-quinolinecarbonitrile (0.40 g, 1.0 mmol), 1-bromobutane (0.41 g, 3.0 mmol), potassium carbonate (0.30 g, 2.2 mmol), and 2.0 ml of DMF was stirred at 65–70° C. for 5 h, concentrated to dryness, and partitioned with ethyl acetate and water containing acetic acid to give pH~6. The organic layer was washed with water, dried and concentrated. The residue was stirred with potassium carbonate (0.55 g, 4.0 mmol), and 10 ml of methanol at reflux temperature for 60 m and then evaporated to dryness. The residue was partitioned with methylene chloride and water saturated with carbon dioxide (pH~8–9). The organic layer was separated and washed with water, dried, and concentrated. A solution of the residue in 60:30:1 heptane-ethyl acetate-acetic was filtered through a pad of silica gel. The filtrate was evaporated to give an amorphous solid; mass spectrum (electrospray, m/e) M+H 467.9, 469.9.

EXAMPLE 306

4-Chloro-7-methoxy-3-quinolinecarbonitrile

In the manner of Example 115 treatment of 1,4-dihydroquinolin-7-methoxy-4-oxo-3-carbonitrile with phosphorous oxychloride gave the title compound as a tan solid; mass spectrum (electrospray, m/e) M+H 219.2, 221.2.

EXAMPLE 307

4-(4-Chloro-2-fluorophenylamino)-7-methoxy-3-quinolinecarbonitrile

In the manner of Example 274 reaction of 4-chloro-7-methoxy-3-quinolinecarbonitrile with 4-chloro-2-fluoroaniline gave the title compound as an amber solid, mp 208–210° C.

EXAMPLE 308

4-(4-Chloro-2-fluorophenylamino)-7-hydroxy-3-quinolinecarbonitrile

In the manner of Example 302 reaction of 4-(4-chloro-2-fluorophenylamino)-7-methoxy-3-quinolinecarbonitrile with pyridine hydrochloride at 210° C. gave the title compound, mp 295–305° C.

EXAMPLE 309

4-[(4-Chloro-2-fluorophenylamino)-N-acetylamino]-7-hydroxy-3-quinolinecarbonitrile In the manner of Example 304 peracetylation of 4-(4-chloro-2-fluorophenylamino)-7-hydroxy-3-quinolinecarbonitrile with acetic anhydride in the presence of dimethylaminopyridine followed by de-O-acetylation with sodium bicarbonate in aqueous methanol gave the title compound as an amber solid, mp 182–191° C.

EXAMPLE 310

4-(4-Chloro-2-fluorophenylamino)-7-ethoxy-3-ciuinolinecarbonitrile

In the manner of Example 305 alkylation of 4-[(4-Chloro-2-fluorophenylamino)-N-acetylamino]-7-hydroxy-3-

EXAMPLE 311

4-[(3-Bromophenyl)amino]-6,7-bis(2-methoxyethoxy)-3-quinolinecarbonitrile

In the manner of Example 305 alkylation of 4-(3-bromophenylamino)-6,7-dihydroxy-3-quinolinecarbonitrile with 2-bromoethyl methyl ether in the presence of potassium carbonate in DMF gave the title compound as a light yellow solid, mp 135–138° C.

EXAMPLE 312

4-(4-Hydroxy-2-methyl-phenylamino)-6-methoxy-7-(3-morpholin-4yl-propoxy)-quinoline-3-carbonitrile A mixture of 0.3 g of 4-chloro-6-methoxy-7-(3-morpholin-4-yl-propoxy)-quinoline-3-carbonitrile derivative, 0.12 g of 4-amino-m-cresol, 0.1 g of pyridine hydrochloride and 4 ml of 2-ethoxy ethanol was stirred under nitrogen at reflux temperature for 1.5 hr. The mixture was cooled and added to the mixture of ethyl acetate and saturated solution of sodium bicarbonate, stirred for 15 minutes. Following separation of layers, the organic layer was dried over anhydrous sodium sulfate, filtered and filtrate was evaporated to yield dark oil. The oil was purified by silica gel flash chromatography utilizing a gradient of methylene chloride/methanol (95:5 to 90:10) to give 0.23 g of the title compound as a tan solid, mp 120–126C; mass spectrum (electrospray, m/e): M+H 449.

EXAMPLE 313

4-(3-Bromo-phenylamino)-6-methoxy-7-(3-morpholin-4-yl-propoxy)-quinoline-3-carbonitrile The method of Example 312 was used as well as 0.3 g of 4-chloro-6-methoxy-7-(3-morpholin-4-yl-propoxy)-quinoline-3-carbonitrile, 0.12 ml of 3-bromo aniline, 0.1 g of pyridine hydrochloride and 4.0 ml of 2-ethoxy ethanol. This afforded an oil which was purified by silica gel flash chromatography utilizing a gradient of methylene chloride/methanol (96:4 to 92:8) to give 0.22 g of the title compound as an off white solid,mp 115–118 C; mass spectrum (ES,m/e): M+H499.

EXAMPLE 314

6-Methoxy-4-(2-methylsulfanyl-phenylamino)-7-(3-morpholin-4-yl-propoxy)-quinoline-3-carbonitrile The method of Example 312 was used as well as 0.3 g of 4-chloro-6-methoxy-7-(3-morpholin-4-yl-propoxy)-quinoline-3-carbonitrile, 0.14 ml of 2-(methyl mercapto) aniline, 0.1 g of pyridine hydrochloride and 4.0 ml of 2-ethoxy ethanol. This afforded an oil which was purified by silica gel flash chromatography [methylene chloride/methanol (96:4) ] to give 0.16 g of the title compound as an off white solid, mp 179–180 C.; mass spectrum (ES, m/e): M+H465.

EXAMPLE 315

4-(4-Hydroxy-3,5-dimethyl-phenylamino)-6-methoxy-7-(3-morpholin-4-yl-propoxy)-quinoline-3-carbonitrile The method of Example 312 was used as well as 0.25 g of 4-chloro-6-methoxy-7-(3-morpholin-4-yl- propoxy)-quinoline-3-carbonitrile, 0.12 ml of 4-amino, 2–5 dimethyl phenol, 0.1 g of pyridine hydrochloride and 4.0 ml of 2-ethoxy ethanol. This afforded an oil which was purified by silica gel flash chromatography utilizing a gradient of methylene chloride/methanol (96:4 to 92:8) to give 0.20 g of the title compound as a tan foam, mp 122–125 C.; mass spectrum (ES, m/e): M+H481.

EXAMPLE 316

4-(2-Aminphenylmethylamino)-6,7-diethoxy-3-quinolinecarbonitrile

In the manner of Example 61 reaction of 4-chloro-6,7-diethoxy-3-quinolinecarbonitrile with 2-aminobenzylamine gave the title compound as an off-white solid, mp 173–177° C.

EXAMPLE 317

4-(3,4-Difluorophenylmethylamino)-6,7-diethoxy-3-quinolinecarbonitrile

In the manner of Example 61 reaction of 4-chloro-6,7-diethoxy-3-quinolinecarbonitrile with 3,4-difluorobenzylamine gave the title compound as a tan solid, mp 167–169° C.

EXAMPLE 318

4-Methoxy-but-2-enoic acid [4-(3-bromo-phenylamino)-quinazolin-6-yl]-amide

To a solution of 1 g (3.17 mmol) of 6-amino-4-[(3-bromophenyl)amino]-3-quinolinecarbonitrile and 0.6 g of disopropylethylamine in 21 ml of tetrahydrofuran was added 0.47 g (3.5 mmol) of 4-methoxycrotonoyl chloride at 0° C. with stirring. After 1.5 hr at 0° C. another 0.15 g of acid chloride was added. The mixture was diluted with 75 ml of tetrahydrofuran and stirred with a mixture of brine and saturated sodium bicarbonate. 50 ml of ethyl acetate was added and the organic layer was separated and dried over magnesium sulfate. Solvent was removed and the residue was purified by chromatography on silica gel. Recrystalization from 1-butanol gave 1.25 g of a yellow powder: mass spectrum (electrospray, m/e): M+H 415.0 and 415.9.

EXAMPLE 319

4-(4-Chloro-2-fluoro-5-hydroxy-phenylamino)-6,7-dimethoxy-quinoline-3-carbonitrile A mixture of 0.25 g of 4-chloro-6,7-dimethoxy-3-quinolinecarbonitrile, 0.195 g of 4-chloro-2-fluoro-5-hydroxyaniline, 0.116 g of pyridine hydrochloride, and 3 ml of ethoxyethanol was stirred under nitrogen, at reflux temperature for 1 h. The mixture was cooled and added to 10 ml of water. To this mixture was added sodium carbonate until pH 9. The product was collected, washed with water, and dried to give 0.327 g of 4-(4-chloro-2-fluoro-5-hydroxy-phenylamino)-6,7-dimethoxy-quinoline-3-carbonitrile as a solid, dec>260° C.; mass spectrum (electrospray, m/e): M+H 373.9.

EXAMPLE 320

7-Benzyloxy-4-hydroxy-6-methoxy-quinoline-3-carbonitrile

To a stirred solution of 26.9 ml of n-butyllithium (2.5 M in hexane) in 50 ml of THF at −78° C. was added a 3.51 ml of acetonitrile in 20 ml of THF during 10 min. After stirring at −78° C. for 30 min, the mixture was treated with 10 g of L17741-150 (B. Floyd) in 20 ml of THF during 5 min. After 15 min at −78° C. the stirred mixture was warmed to 0° C. for a further 30 min. It was then treated with 5 ml of acetic acid, warmed to 25° C. and stirred for 30 min. The mixture was evaporated to dryness, and diluted with aqueous sodium bicarbonate. The resulting off-white solid was filtered, washed with water, ethyl acetate and ether. After drying, 4.5 g of 7-benzyloxy-4-hydroxy-6-methoxy-quinoline-3-carbonitrile was obtained as an off-white solid, dec >255° C.; mass spectrum (electrospray, m/e) M+H 307.

EXAMPLE 321

7-Benzyloxy-4-chloro-6-methoxy-quinoline-3-carbonitrile

To a stirred suspension of 1 g of 7-benzyloxy-4-hydroxy-6-methoxy-quinoline-3-carbonitrile in 10 ml of methylene chloride was added 5 ml of oxalyl chloride (2M in methylene chloride), and 2 drops of N,N-dimethylformamide. The mixture was refluxed for 20 min and to it was slowly added aqueous sodium bicarbonate until the bubbling ceased. Following separation of the layers, the organic layer was evaporated to a small volume, then passed through a plug of magnesol. Elution with 50 ml methylene chloride, followed by evaporation provided 0.6 g of 7-benzyloxy-4-chloro-6-methoxy-quinoline-3-carbonitrile as a pale yellow solid, mp 282–284° C.; mass spectrum (electrospray, m/e) M+H 325.

EXAMPLE 322

7-Benzyloxy-4-(4-chloro-2-fluoro-phenylamino)-6-methoxy-quinoline-3-carbonitrile A mixture of 0.200 g of 7-benzyloxy-4-chloro-6-methoxy-quinoline-3-carbonitrile 0.108 g of 4-chloro-2-fluoroaniline, 0.071 g of pyridine hydrochloride, and 3 ml of ethoxyethanol was stirred under nitrogen, at reflux temperature for 1 h. The mixture was cooled and added to 10 ml of water. To this mixture was added sodium carbonate until pH 9. The product was collected, washed with water, and dried to give 0.150 g of 7-Benzyloxy-4-(4-chloro-2-fluoro-phenylamino)-6-methoxy-quinoline-3-carbonitrile hydrochloride as a solid, mp 241–243° C.; mass spectrum (electrospray, m/e): M+H 433.9.

EXAMPLE 323

4-(4-Chloro-2-fluoro-5-hydroxy-phenylamino)-7-methoxy-6-(3-morpholin-4-yl)-propoxyl-quinoline-3-carbonitrile A mixture of 0.35 g of 4-chloro-7-methoxy-6-(3-morpholin-4-yl-propoxy))-3-quinolinecarbonitrile, 0.188 g of 4-chloro-2-fluoro-5-hydroxyaniline, 0.112 g of pyridine hydrochloride, and 4 ml of ethoxyethanol was stirred under nitrogen, at reflux temperature for 1 h. The mixture was cooled and added to 10 ml of water. To this mixture was added sodium carbonate until pH 9. The product was collected, washed with water, and dried to give 0.210 g of 4-(4-Chloro-2-fluoro-5-hydroxy-phenylamino)-7-methoxy-6-(3-morpholin-4-yl)-propoxyl-quinoline-3-carbonitrile as a solid, mp 125–128° C.; mass spectrum (electrospray, m/e): M+H 487.0.

EXAMPLE 324

4-(3-Acetylphenylamino)-6,7-dimethoxy-3-quinolinecarbonitrile

In the manner of Example 274 reaction of 4-chloro-6,7-dimethoxy-3-quinolinecarbonitrile with 3-aminoacetophenone gave the title compound as a tan solid, mp 204–206° C.

EXAMPLE 325

4-(3-Bromophenylamino)-6,7-di-methoxymethyl-3-quinolinecarbonitrile

In the manner of Example 305 treatment of 4-(3-bromophenylamino)-6,7-dihydroxy-3-quinolinecarbonitrile with potassium carbonate and chloromethyl ether in dimethylformamide gave the title compound as a yellow solid: mp=113–116° C.

EXAMPLE 326

N-[4-(3-Bromo-phenylamino)-3-cyano-quinolin-6-yl]-3-chloro-(E) acrylamide and

EXAMPLE 327

N-[4-(3-Bromo-phenylamino)-3-cyano-quinolin-6-yl]-3-chloro-(Z)-acrylamide

To a solution of 0.5 g (1.47 mmol) of of 6-amino-4-[(3-bromophenyl)amino]-3-quinolinecarbonitrile and 0.24 g (1.8 mmol) of diisopropylethyl amine in 3 ml of terahydrofuran at 0° C. with stirring was added 0.21 g (1.7 mmol) of 3-chloro-acryloyl chloride (cis/trans mixture) in 2 ml of tetrahydrofuran. After 40 min at 0° C., the mixture was poured into a saturated solution of sodium bicarbonate and then extracted ether. The organic solution was dried over magnesium sulfate and the sovent was removed. The residue chromatographed on silica gel giving 0.16 g of N-[4-(3-bromo-phenylamino)-3-cyano-quinolin-6-yl]-3-chloro-(E) acrylamide: mass spectrum (electrospray, m/e,): M+H 424.9, 427.0, and 0.12 g of N-[4-(3-bromo-phenylamino)-3-cyano-quinolin-6-yl]-3-chloro-(Z) acrylamide acrylamide: mass spectrum (electrospray, m/e,): M+H 425.0, 427.0

EXAMPLE 328

N-[4-[(3-Bromonhenyl)amino]-3-cyano-6-quinolinyl]-4-morpholino-2-butynamide

Isobutyl chloroformate (0.161 g, 1.1 8 mmol) was dropwise added into an ice cold solution of 4-morpholino-2-butynoic acid (0.25 g, 1.48 mmol) and N-methylmorpholine (0.15 g, 1.48 mmol) in 8 mL of tetrahydrofuran under $N_2$. After stirring for 30 min, a solution of 025 g (0.74 mmol) of 6-amino-4-[(3-bromophenyl)amino]-3-quinolinecarbonitrile in 6 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.096 g (27%) of yellow solid; : mass spectrum (electrospray, m/e,) 490.1, 492.1 (M+H$^+$); mp 145–148° C.

EXAMPLE 329

N-[4-[(3-Bromophenyl)amino]-3-cyano-6-quinolinyl]-4-dimethylamino-2-butynamide

Isobutyl chloroformate (0.342 g, 2.5 mmol) was dropwise added into an ice cold solution of 4-dimethylamino-2- butynoic acid (0.9 g, 3.8 mmol) and N-methyl-morpholine (0.384 g, 3.8mmol) in 50 mL of tetrahydrofaan under N$_2$. After stirring for 30 min, a solution of 0.644 g (1.9 mmol) of 6-amino-4-[(3-bromophenyl)amino]-3-quinolinecarbonitrile in 10 mL of pyridine was added dropwise and the mixture was stirred at 0° C. for 2.5 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.144 g (21%) of yellow solid; mass spectrum (electrospray, m/e,): 447.9, 450.2 (M+H$^+$); mp 180° C. (dec.).

EXAMPLE 330

N-[4-[(3-Bromophenyl)amino]-3-cyano-6-quinolinyl]-4-methoxy-2-butynamide

Isobutyl chloroformate (0.432 g, 3.2 mmol) was dropwise added into an ice cold solution of 4-methoxy-2-butynoic acid (0.72 g, 6.32 mmol) and N-methylmorpholine (0.959 g, 9.78 mmol) in 20 mL of tetrahydrofuran under N$_2$. After stirring for 30 min, a solution of 0.5 g (1.58 mmol) of 6-amino-4-[(3-bromophenyl)amino]-3-quinolinecarbonitrile in 8 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by thin-layer chromatography eluted with 5% methanol in chlorform. The product was collected, and dried in vacuo to give 0.27 g (41%) of yellow solid; mass spectrum (electrospray, m/e,): 435.1, 437.0 (M+H$^+$); mp 197° C. (dec.).

EXAMPLE 331

N-[4-[(3-Bromoohenyl)amino]-3-cyano-6-quinolinyl]-4-t-butyldimethylsiloxy-2-butynamide Isobutyl chloroformate (0.214 g, 1.57 mmol) was dropwise added into an ice cold solution of 4-t-butyldimethylsiloxy-2-butynoic acid (0.336 g, 1.57 mmol) and N-methylmorpholine (0.1 9 g, 1.88 mmol) in 15 mL of tetrahydrofuran under N$_2$. After stirring for 30 min, the reaction mixture was added dropwise into a solution of 0.4 g (1.18 mmol) of 6-amino-4-[(3-bromophenyl)amino]-3-quinolinecarbonitrile in 3 mL of tetrahydrofuran and 1.5 mL of pyridine and stirred at 0° C. for 1 hr. The reaction was quenched with ice water, poured into saturated sodium bicarbonate and brine, and extracted with ethyl acetate. The ethyl acetate layer was concentrated and purified by column chromatography eluted with 60% ethyl acetate in hexane. The product was collected, and dried in vacuo to give 0.22 g (35%) of yellow solid;: mass spectrum (electrospray, m/e,): 535.1189 (M$^+$).

EXAMPLE 332

N-[4-[(3-Bromophenyl)amino]-3-cyano-6-quinolinyl]-4-hydroxy-2-butynamide

N-[4-[(3-Bromophenyl)amino]-3-cyano-6-quinolinyl]-4-t-butyldimethylsiloxy-2-butynamide (60mg, 0.122 mmol) was dissolved in a solution of acetic acid, tetrahydrofuran and water (3:1:1) and stirred overnight at room temperature. The solution was diluted with ethyl acetate and washed with saturated sodium bicarbonate and brine. The ethyl acetate was concentrated to give 42.2 mg (90%) of yellow solid;: mass spectrum (electrospray, m/e,): 421.0311 (M$^+$).

EXAMPLE 333

4-(3-Hydroxymethyl-2-methylphenylamino)-6,7-dimethoxyquinoline-3-carbonitrile

A mixture of 0.248 g (1 mmol)of 4-chloro-6,7-dimethoxyquinoline-3-carbonitrile, 0.151 g (1.1 mmol) of 3-amino-2-methylbenzyl alcohol, 0.116 g (1 mmol) pyridine hydrochloride and 12 ml of 2-ethoxyethanol was heated in a 138–140° C. oil bath for 6 hours; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.32 g (91.5%) of the desired product as light tan crystals. MP 123–125° C.;: mass spectrum (electrospray, m/e,): 349.9(M+H)$^+$.

EXAMPLE 334

4-(2-Amino-4,5-dimethylohenylamino)-6,7-dimethoxyquinoline-3-carbonitrile

A mixture of 0.248 g (1 mmol)of 4-chloro-6,7-dimethoxyquinoline-3-carbonitrile, 0.410 g (3.0 mmol) of 4,5-dimethyl-1,2-diphenylenediamine, 0.116 g (1 mmol) pyridine hydrochloride and 12 ml of 2-ethoxyethanol was heated in a 138–140° C. oil bath for 1 hour; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.587 g of the desired product (impure). The impure product was digested with 50 ml of chloroform and 50 ml of ethyl acetate for 0.5 hour, collected, washed with chloroform and dried to give 0.307 g (88%) of the desired pure product as yellow crystals. MP 260–262° C.;: mass spectrum (electrospray, m/e,): 348.1582(HR).

EXAMPLE 335

4-(4-Ethylphenylamino)-6,7-dimethoxyquinoline-3-carbonitrile

A mixture of 0.248 g (1 mmol)of 4-chloro-6,7-dimethoxyquinoline-3-carbonitrile, 0.14 ml (1.1 mmol) of 4-ethylaniline, 0.116 g (1 mmol) pyridine hydrochloride and 12 ml of 2-ethoxyethanol was heated in a 138–140° C. oil bath for 1 hour; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.325 g (97.5%) of the desired product as light cream crystals. MP 248–250° C.;: mass spectrum (electrospray, m/e,): 333.1462.

EXAMPLE 336

4-(4-Chloro-2-methylphenylamino)-6,7-dimethoxyquinoline-3-carbonitrile

A mixture of 0.248 g (1 mmol) of 4-chloro-6,7-dimethoxy-quinoline-3-carbonitrile, 0.156 g (1.1 mmol) of 4-chloro-2-methylaniline, 0.116 g (1 mmol) pyridine hydrochloride and 12 ml of 2-ethoxyethanol was heated in a 138–140° C. oil bath for 24 hours; progress of the reaction was monitored by TLC. After 24 hours an additional 0.156 g of of 4-chloro-2-methylaniline was added and the heating continued for 24 hours. When TLC indicated the disappearance of starting material, the reaction was cooled and concentrated in vacuo to a thick oil. To this oil was added 50 ml of water followed by 5 ml of 1M NaHCO$_3$, approximately pH 8. The gummy solid was dissolved in chloroform and passed through a pad of hydrous magnesium silicate. The liquid was concentrated in vacuo and the residue triturated 5 times with hexane. The resulting precipitate was collected, washed with hexane, and dried in vacuo at 65° C. to give 0.250 g (71%) of the desired product as brown crystals. MP 227–229° C.;: mass spectrum (electrospray, m/e,): 353.8(M+H)$^+$.

EXAMPLE 337

6,7-Dimethoxy-4-(3-phenoxyphenylamino) quinoline-3-carbonitrile

A mixture of 0.248 g (1 mmol) of 4-chloro-6,7-dimethoxy-quinoline-3-carbonitrile, 0.204 g (1.1 mmol) of 3-phenoxyaniline, 0.116 g (1 mmol) pyridine hydrochloride and 12 ml of 2-ethoxyethanol was heated in a 138–140° C. oil bath for 3 hours; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.309 g (78%) of the desired product as cream crystals. MP 253–254° C.; mass spectrum (electrospray, m/e,): 397.0(M+H)$^+$.

EXAMPLE 338

4-(4-Chloro-3-trifluoromethylphenylamino)-6,7-dimethoxyquinoline-3-carbonitrile

A mixture of 0.248 g (1 mmol) of 4-chloro-6,7-dimethoxy-quinoline-3-carbonitrile, 0.215 g of 4-chloro-3-trifluoromethylaniline, 0.116 g (1 mmol) pyridine hydrochloride and 12 ml of 2-ethoxyethanol was heated in a 138–140° C. oil bath for 1.5 hours; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.266 g (65.5%) of the desired product as cream crystals. MP 265–267° C.; mass spectrum (electrospray, m/e,): 408.2(M+H)$^+$.

EXAMPLE 339

4-(3-Hydroxy-phenylamino)-6,7-dimethoxy-quinoline-3-carbonitrile

Using the method described in Example 105, 0.7 g of 4-chloro-6,7-dimethoxy-3-quinolinecarbonitrile and 0.38 g of 3-aminophenol was converted to 0.83 g of the title compound: mass spectrum (electrospray, m/e,): 321.9, 322.8 (M+H)$^+$

EXAMPLE 340

4-(4-methyl-phenylamino)-6,7-dimethoxy-quinoline-3-carbonitrile

Using the method described in Example 105, 0.7 g of 4-chloro-6,7-dimethoxy-3-quinolinecarbonitrile and 0.317 g of 4-methylphenol was converted to 0.79 g of the title compound: MP=128–130° C.

EXAMPLE 341

4-(3-Hydroxy-4-methyl-phenylamino)-8-methoxy-6-nitro-quinoline-3-carbonitrile

Using the method described in Example 105, 0.5 g of 4-chloro-8-methoxy-6-nitro-3-quinolinecarbonitrile and 0.28 g of 3-hydroxy-4-methylphenol was converted to 0.3 g of the title compound: mass spectrum (electrospray, m/e,): 350.9, 351.9 (M+H)$^+$

EXAMPLE 342

4-(4-Chloro-2-fluoro-phenylamino)-8-methoxy-6-nitro-quinoline-3- carbonitrile

Using the method described in Example 105, 0.5 g of 4-chloro-8-methoxy-6-nitro-3-quinolinecarbonitrile and 0.25 ml of 4-chloro-2-fluoro phenol was converted to 0.08 g of the title compound: mass spectrum (electrospray, m/e,): 372.8, 374.8 (M+H)$^+$

EXAMPLE 343

4-(3-Hydroxy-4-methoxy-phenylamino)-8-methoxy-6-nitro-quinoline-3-carbonitrile

Using the method described in Example 105, 0.5 g of 4-chloro-8-methoxy-6-nitro-3-quinolinecarbonitrile and 0.31 g of 3-hydroxy-4-methoxy phenol was converted to 0.21 g of the title compound: mass spectrum (electrospray, m/e,): 366.9, 367.9 (M+H)$^+$

EXAMPLE 344

6-Amino-4-(3-hydroxy-4-methyl-phenylamino)-8-methoxy-quinoline-3-carbonitrile

Using the method described in Example 196, 0.2 g of 4-(3-hydroxy-4-methyl-phenylamino)-8-methoxy-6-nitro-quinoline-3-carbonitrile and 0.1 g of iron was converted to 0.14 g of the title compound: MP=227° C. (dec)

EXAMPLE 345

6-Amino-4-(3-hydroxy-4-methoxy-phenylamino)-8-methoxy -quinoline-3-carbonitrile

Using the method described in Example 196, 0.1 g of 4-(3-hydroxy-4-methoxy-phenylamino)-8-methoxy-6-nitro-quinoline-3-carbonitrile and 0.09 g of iron was converted to the title compound: MP=215° C. (dec)

EXAMPLE 346

N-{4-[(3-Bromo-4-fluorophenyl)amino]-3-cyano-7-methoxy-6-quinolinyl}-4-bromo-2-butenamide By using the method described in EXAMPLE 172 and not reacting with dimethylamine, a portion of 6-amino-4-(3-bromo-4-fluoro-phenylamino)-7-methoxy-quinoline-3-carbonitrile was converted to the title compound: mass spectrum (electrospray, m/e,): 532.8, 534.8, 536.8 (M+H)$^+$

EXAMPLE 347

N-{4-[(3-Bromophenyl)amino]-3-cyano-7-methoxy-6-quinolinyl}-4-chloro-2-butenamide In the method described in EXAMPLE 198, a side product was isolated that proved to be the title compound: mass spectrum (electrospray, m/e,): 471.25, 473.3(M+H)$^+$

EXAMPLE 348

N-{3-Cyano-4-[(3-iodophenyl)amino]-6-quinolinyl}-2-butynamide

Dissolved 275 mg (3.27 mmol) 2-butynoic acid in 20 ml THF under $N_2$ and chilled to 0° C. Added 420 µl (3.23 mmol) isobutyl chloroformate and 355 µl (3.24 mmol) N-methylmorpholine and stirred for 10 minutes. Added dropwise a solution of 500 mg (1.30 mmol) 6-amino-4-[(3-iodophenyl)amino]-3-quinolinecarbonitrile and after 15 minutes, removed ice bath and stirred overnight at 25° C. Stripped solvent, washed with water and collected solids. Boiled in ethyl acetate, collected, and dried in vacuo, giving 228 mg of orange-brown solid: mass spectrum (electrospray m/e): M+H=453.1.

EXAMPLE 349

N-{3-Cyano-4-[(3-methylphenyl)amino]-6-quinolinyl}-2-propenamide

Dissolved 500 mg (1.82 mmol) of 6-amino-4-[(3-methylphenyl)amino]-3-quinolinecarbonitrile in 1.0 ml DMF and 6 ml THF and chilled to 0° C. under $N_2$. Added 280 µl (2.00 mmol) triethylamine and 166 µl (2.00 mmol) acryloyl chloride. Removed ice bath at 15 minutes and at 1 hour, stripped solvent and slurried residue with dilute sodium bicarbonate. Collected crystals and washed with water. Boiled solids in ethyl acetate, collected and dried in vacuo, giving 238 mg of yellow-orange solid: mass spectrum (electrospray m/e): M+H=329.1.

EXAMPLE 350

N-{4-[(4-Bromophenyl)amino]-3-cyano-6-quinolinyl}-2-butynamide

Dissolved 310 mg (3.68 mmol) 2-butynoic acid in 20 ml THF and chilled to 0° C. under $N_2$. Added 480 µl (3.68 mmol) isobutyl chloroformate and 410 µl (3.72 mmol) N-methylmorpholine. Stirred for 20 minutes and dropwise added a solution of 500 mg (1.47 mmol) 6-amino-4-[(4-bromophenyl)amino]-3-quinolinecarbonitrile in 1 ml DMF and 10 ml THF. Removed ice bath after 15 minutes and stirred at 25° C. overnight. Stripped solvent, slurried residue with water and collected solids. Boiled solids in ethyl acetate, collected, and dried in vacuo, giving 341 mg of yellow solid: mass spectrum (electrospray m/e): M+H= 405.1, 407.1.

EXAMPLE 351

N-{4-[(3-Chloro-4-thiophenoxyphenyl)amino]-3-cyano-6-quinolinyl}-2-propenamide Dissolved 1.00 g (2.48 mmol) 6-amino-4-[(3-chloro-4-thiophenoxyphenyl)amino]-3-quinolinecarbonitrile in 2.0 ml DMF and 12 ml THF and chilled to 0° C. under $N_2$. Added 380 µl (2.73 mmol) triethylamine and 227 µl (2.73 mmol) acryloyl chloride. Removed ice bath at 15 minutes and at 1.5 hours stripped solvent and slurried residue with dilute sodium bicarbonate. Collected solids and washed with water. Recrystallized from ethyl acetate and dried in vacuo, giving 293 mg of yellow-orange solid: mass spectrum (electrospray m/e): M+H=457.3.459.3.

EXAMPLE 352

N-{3-Cyano-4-[(3,4-difluorophenyl)amino]-6-quinolinyl}-2-butynamide

Dissolved 425 mg (5.06 mmol) 2-butynoic acid in 40 ml THF and chilled to 0° C. under $N_2$. Added 556 µl (5.06 mmol) N-methylmorpholine and 658 µl (5.06 mmol) isobutyl chloroformate and stirred for 10 minutes. Added dropwise a solution of 1.00 g (3.37 mmol) 6-amino-4-[(3,4-difluorophenyl)amino]-3-quinolinecarbonitrile in 2.0 ml hot DMF and 20 ml THF. Removed ice bath at 15 minutes and stirred at 25° C. overnight. Stripped solvent, slurried residue with water, and collected solids. Boiled in ethyl acetate, collected solids, and dried in vacuo, giving 735 mg of yellow solid: mass spectrum (electrospray m/e): M+H=363.3

EXAMPLE 353

N-{4-[(3-Chlorophenol)amino]-3-cyano-6-quinolinyl}-2-butynamide

Dissolved 428 mg (5.09 mmol) 2-butynoic acid in 40 ml THF and chilled to 0° C. under $N_2$. Added 560 µl (5.09 mmol) N-methylmorpholine and 662 µl (5.09 mmol) isobutyl chloroformate and stirred for 10 minutes. Added dropwise a solution of 1.00 g (3.39 mmol) 6-amino-4-[(3-chlorophenyl)amino]-3-quinolinecarbonitrile in 2 ml DMF and 20 ml THF. Removed ice bath at 15 minutes and stirred at 25° C. overnight. Stripped solvent, slurried residue with water and collected solids. Boiled in ethyl acetate, collected and dried in vacuo, giving 975 mg of yellow solid: mass spectrum (electrospray m/e): M+H=361.1, 363.2.

EXAMPLE 354

N-{3-Cyano-4-[(3-isopropylphenyl)amino]-6-quinolinyl}-2-butynamide

Dissolved 695 mg (8.27 mmol) 2-butynoic acid in 40 ml THF and chilled to 0° C. under $N_2$. Added 1.08 ml (8.30 mmol) isobutyl chloroformate and 910 µl (8.27 mmol) N-methylmorpholine and stirred for 10 minutes. Dropwise added a solution of 1.00 g (3.31 mmol) 6-amino-4-[(3-isopropylphenyl)amino]-3-quinolinecarbonitrile in 2.0 ml DMF and 15 ml THF. Removed ice bath at 15 minutes and stirred at 25° C. overnight. Stripped solvent, slurried residue with water, and collected solid. Recrystallized from ethyl acetate and dried in vacuo, giving 329 mg of yellow-green solid: mass spectrum (electrospray m/e): M+H=369.2.

EXAMPLE 355

N-{3-Cyano-4-[(3-isopropylphenyl)amino]-6-quinolinyl}-2-propenamide

Dissolved 1.00 g (3.31 mmol) 6-amino-4-[(3-isopropylphenyl)amino]-3-quinolinecarbonitrile in 2.0 ml hot DMF, added 12 ml THF, and chilled to 0° C. under $N_2$. Added 507 µl (3.64 mmol) triethylamine and 303 µl (3.64 mmol) acryloyl chloride. Removed ice bath at 15 minutes and at 1 hour stripped solvent. Slurried residue with dilute sodium bicarbonate, collected solids and washed with water. Recrystallized from ethyl acetate and dried in vacuo, giving 366 mg of orange solid: mass spectrum (electrospray m/e): M+H=357.1.

EXAMPLE 356

6-Amino-4-[(3-isopropylphenyl)amino]-3-quinolinecarbonitrile

Added 0.5 g 10% palladium on carbon to a flask under $N_2$ and covered with 250 ml ethanol. To this added 4.818 g (14.5 mmol) 4-[(3-isopropylphenyl)amino]-6-nitro-3-quinolinecarbonitrile and 1.14 ml (36.2 mmol) anhydrous hydrazine and heated to reflux. At 1.5 hours, filtered hot mixture through celite, stripped solvent, and dried in vacuo, giving 4.30 g of yellow solid: mass spectrum (electrospray m/e): M+H=303.1.

EXAMPLE 357

4-[(3-Isopropylphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.48 g (25.8 mmol) 3-isopropylaniline was heated to reflux under $N_2$. At 4 hours, removed heat and made basic with saturated sodium bicarbonate. Stripped solvents and azeotroped with ethanol. Slurried residue with hexane and collected solids. Dissolved in ethyl acetate, stirred with Darco, filtered through celite, stripped solvent and dried in vacuo, giving 5.289 g of yellow solid: mass spectrum (electrospray m/e): M+H=333.1.

EXAMPLE 358

4-(3-Bromo-phenylamino)-6-(3-pyrrolidin-1-yl-propylamino)-quinoline-3-carbonitrile Dissolved 0.64 g (3.69 mmol) 3-(pyrrolidin-1-yl) propionaldehyde dimethyl acetal in 10 ml water and acidified to pH 1 with concentrated HCl. Heated to 40° C. for 90 minutes, removed heat and neutralized with sodium bicarbonate. Dissolved 500 mg (1.47 mmol) 6-amino-4-(3-bromo-phenylamino)-quinoline-3-carbonitrile in 100 ml ethanol and added acetic acid until pH was 3 to 4. Added the deprotected aldehyde to the amine solution and stirred at 25° C. for 0.5 hour. Gradually added 94 mg (1.47 mmol) sodium cyanoborohydride and stirred overnight. Stripped solvent, partitioned between chloroform and water. Washed organic layer with brine and dried with sodium sulfate. Stripped solvent and filtered through a pad of silica gel, first with 10% methanol/chloroform, then 20% methanol/chloroform/1% ammonium hydroxide. Stripped solvent and dried in vacuo, giving 143 mg of yellow-brown solid: mass spectrum (electrospray m/e): M+H=450, 452.1.

EXAMPLE 359

4-(3-Azido-phenylamino)-6,7-dimethoxy-quinoline-3-carbonitrile

Dissolved 643 mg (2.00 mmol) 4-(3-amino-phenylamino)-6,7-dimethoxy-quinoline-3-carbonitrile in 25 ml 80% acetic acid in water. Chilled to 0° C. and added 152 mg (2.21 mmol) sodium nitrite in 2.2 ml water. After 10 minutes, added 144 mg (2.21 mmol) sodium azide in 2.2 ml water. At 1.5 hours stripped solvent and dissolved residue in hot ethyl acetate. Washed with saturated sodium bicarbonate, water and brine and dried with sodium sulfate. Stripped solvent and redissolved in 60% ethyl acetate/methylene chloride and filtered through a pad of silica gel. Stripped solvent and dried in vacuo, giving 526 mg of brown solid: mass spectrum (electrospray m/e): M+H=347.1.

EXAMPLE 360

6-Amino-4-[(4-Chloro-2-fluorophenyl)amino]-7-methoxy-3-quinolinecarbonitrile

A mixture of 500 mg (1.34 mmol) 4-[(4-chloro-2-fluorophenyl)amino]-7-methoxy-6-nitro-3-quinolinecarbonitrile, 20 ml ethanol and 1.52 ml (6.71 mmol) tin chloride dihydrate was heated to reflux under $N_2$. At 3 hours, removed heat, added ice water and made basic with sodium bicarbonate. Stirred for several hours and extracted with chloroform. Dried organic layer with sodium sulfate, stripped solvent and dried in vacuo, giving 350 mg of green solid: mass spectrum (electrospray m/e): M+H= 342.9, 344.8.

EXAMPLE 361

4-[(4-Chloro-2-fluorophenyl)amino]-7-methoxy-6-nitro-3-quinolinecarbonitrile

A mixture of 5.017 g (19.0 mmol) 4-chloro-7-methoxy-6-nitro-3-quinolinecarbonitrile, 250 ml ethanol, and 2.55 ml 22.8 mmol) 4-chloro-2-fluoroaniline was heated to reflux under $N_2$. At 3.5 hours, removed heat and made basic with saturated sodium bicarbonate. Stripped solvents and azeotroped with ethanol. Slurried residue with hexane, collected solids, and washed with water. Dissolved in ethyl acetate, stirred with Darco, filtered, stripped solvent, and dried in vacuo, giving 6.54 g of yellow solid: mass spectrum (electrospray m/e): M+H=372.8, 374.8.

EXAMPLE 362

4-[(3,4-Dichlorophenyl)amino]-6-nitro-3-quinolinecarbonitrile

A mixture of 5.00 g (21.5 mmol) 4-chloro-6-nitro-3-quinolinecarbonitrile, 250 ml ethanol, and 4.17 g (25.6 mmol) 3,4-dichloroaniline was heated to reflux under $N_2$. At 3.5 hours, removed head and made basic with saturated sodium bicarbonate. Stripped solvents and azeotroped with ethanol. Slurried residue with hexane, collected solids and washed with water. Dissolved in ethyl acetate, stirred with Darco, filtered, stripped solvent and dried in vacuo, giving 2.106 g of yellow solid: mass spectrum (electrospray m/e): M+H=359.1, 361.0.

EXAMPLE 363

6-Amino-4-[(3-methylsulfanylphenyl)amino]-3-quinolinecarbonitrile

A mixture of 4.55 g (13.5 mmol) 4-[(3-methylsulfanylphenyl)amino]-6-nitro-3-quinolinecarbonitrile, 250 ml ethanol, 0.46 g 10% palladium on carbon, and 1.06 ml (33.8 mmol) anhydrous hydrazine was heated to reflux. At 4 hours, added 0.5 equivalents of hydrazine, and at 5 hours, filtered the hot mixture through celite. Stripped the solvent and dried in vacuo, giving 4.068 g brown solid: mass spectrum (electrospray m/e): M+H= 307.1.

EXAMPLE 364

4-[(3-Methylsulfanylphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.18 ml (25.8 mmol) 3-methylsulfanylaniline was heated to reflux under $N_2$. At 2 hours, removed heat and made basic with saturated sodium bicarbonate. Stripped solvents and air dried. Washed residue with hexane, collected solids and washed with water. Dissolved in ethyl acetate, stirred with Darco, stripped solvent and dried in vacuo, giving 4.848 g of yellow solid: mass spectrum (electrospray m/e): M+H=337.1.

EXAMPLE 365

4-[(3-Trifluoromethoxyphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.4 ml (25.3 mmol) 3-trifluoromethoxyaniline was heated to reflux. At 5 hours, removed heat and made basic with saturated sodium bicarbonate. Stripped solvents, slurried residue with hexane, collected, and washed with water. Dissolved in ethyl acetate, stirred with Darco, filtered, stripped solvent, and dried in vacuo, giving 4.537 g of yellow-orange solid: mass spectrum (electrospray m/e): M+H=374.8.

EXAMPLE 366

4-(3-Dimethylamino-phenylamino)-6,7-dimethoxy-quinoline-3-carbonitrile

A 1.25 gram (5 mmole) portion of 4-chloro, 6,7-dimethoxy-quinoline-3-carbonitrile and a 1.05 gram (5 mmole) portion of N,N-dimethyl-1,3-phenylenediamine in 1 ml of 2-methoxyethanol were refluxed for 2 hours in an oil bath at 154 deg. Cooling gave a solid which was recrystallized from water to give 0.4 grams (19%) of 4-(3-Dimethylamino-phenylamino)-6,7-dimethoxy-quinoline-3-carbonitrile which melted at 246–249° C.: mass spectrum (electrospray m/e): (M+H)=349.2., (M+2H)$^{+2}$=174.9.

EXAMPLE 367

6,7-Dimethoxy-4-(4-methoxy-2-methyl-phenylamino)-quinoline-3-carbonitrile

A reaction mixture of 248.7 mg (1 mmol) of 4-chloro-6,7-dimethoxy-3-quinolinecarbonitrile, 164.6 mg (1.2 mmol) of 4-methoxy-2-methyl-aniline and 115.6 mg (1 mmol) of pyridine hydrochloride in 10 mL of 2-ethoxyethanol was refluxed under $N_2$ for 3 hr. After removal of the solvent, the residue was diluted with water and neutralized to pH 7–8 with diluted sodium carbonate solution. The precipitate was filtered and washed with water and ether. After drying in vacuo. this yielded 250.2 mg (71.7%) of the product as a off red solid, m.p.>131° C. (dec.), mass (electrospray, m/e): M+H 349.9.

EXAMPLE 368

3-(3-Cyano-6,7-dimethoxy-quinolin-4-ylamino)-2-methyl-benzoic acid

Using an analogous procedure to that described in EXAMPLE 367, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 196.5 mg (1.3 mmol) of 3-amino-2-methylbenzoicacid to give 89.6 mg (24.7%) of the product as a gray solid, m.p. 242–245° C., mass (electrospray, m/e): M+H 364.0.

EXAMPLE 369

4-(3-Hydroxy-4-methoxy-phenylamino)-6,7-dimethoxy-quinoline-3-carbonitrile

Using an analogous procedure to that described in EXAMPLE 367, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 167.0 mg (1.2 mmol) of 5-amino-2-methoxyphenol to give 313.3 mg (89.3%) of the product as a gray solid, m.p. 254–256° C., mass (electrospray, m/e): M+H 351.2.

EXAMPLE 370

4-(3-Chloro-4-methyl-phenylamino)-6,7-dimethoxy-quinoline-3-carbonitrile

Using an analogous procedure to that described in EXAMPLE 367, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 170.0 mg (1.2 mmol) of 2-chloro-4-amino-toluene to give 350.9 mg (99.4%) of the product as a yellow solid, m.p.>250° C., mass (electrospray, m/e): M+H 353.9, 355.8.

EXAMPLE 371

6,7-Dimethoxy-4-(4-phenoxy-phenylamino)-quinoline-3-carbonitrile

Using an analogous procedure to that described in EXAMPLE 367, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 222.3 mg (1.2 mmol) of 4-phenoxyaniline to give 283.0 mg (71.3%) of the product as a light yellow solid, m.p. 239–241° C., mass (electrospray, m/e): M+H 397.9.

EXAMPLE 372

4-(5-Chloro-2-methoxyphenylamino)-6,7-dimethoxy-quinoline-3-carbonitrile

Using an analogous procedure to that described in EXAMPLE 367, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 189.1 mg (1.2 mmol) of 5-chloro-o-anisidine to give 240.5 mg (65.0%) of the product as a cream solid, m.p. 200–202° C., mass (electrospray, m/e): M+H 369.9, 371.8.

EXAMPLE 373

4-(4-Chloro-2-fluoro-phenylamino)-6,7-dihydroxy-quinoline-3-carbonitrile

A mixture of 0.358 g of 4-(4-chloro-2-fluoro-phenylamino)-6,7-dimethoxy-quinoline-3-carbonitrile and 3 g of pyridine hydrochloride was stirred under nitrogen at 210–220° C. for 20 minutes. The mixture was cooled and added to 50 ml of 3% ammonium hydroxide solution. The product was collected, washed with water, and dried to give 0.302 g of 4-(4-chloro-2-fluoro-phenylamino)-6,7-dihydroxy-quinoline-3-carbonitrile as a solid, mp 270–272° C.;: mass spectrum (EI, m/e): M 329.0363.

EXAMPLE 374

4-(3-Hydroy-2-metyl-phenylamino)-6,7-dimethoxy-quinoline-3-carbonitrile

A mixture of 0.249 g of 4-chloro-6,7-dimethoxy-3-quinolinecarbonitrile, 0.123 g of 3-amino-o-cresol, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.174 g of 4-(3-hydroxy-2-methyl-phenylamino)-6,7-dimethoxy-quinoline-3-carbonitrile as a solid, mp 255–257° C.; mass spectrum (electrospray, m/e): M+H 335.9.

EXAMPLE 375

4-(3-Chloro-4-methoxy-pheylanino)-6,7-dimethon-quinoline-3-carbonitrile

A mixture of 0.249 g of 4-chloro-6,7-dimethoxy-3-quinolinecarbonitrile, 0.158 g of 3-chloro-p-anisidine, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.324 g of 4-(3-chloro- 4-methoxy-phenylamino)-6,7-dimethoxy-quinoline-3-carbonitrile as a solid, mp 278–280° C.; mass spectrum (EI, m/e): M 369.0860.

EXAMPLE 376

6,7-Dimethoxy-4-(4-trifluoromethyl-phenylamino)-quinoline-3-carbonitrile

A mixture of 0.249 g of 4-chloro-6,7-dimethoxy-3-quinolinecarbonitrile, 0.322 g of 4-(trifluoromethyl)aniline, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.268 g of 6,7-dimethoxy-4-(4-trifluoromethyl-phenylamino)-quinoline-3-carbonitrile as a solid, mp 116–118° C.; mass spectrum (EI, m/e): M 373.1031.

EXAMPLE 377

4-(3,4-Dibromophenylamino)-6-nitroquinoline-3-carbonitrile

A mixture of 6.20 g (26.6 mmol) of 4-chloro-6-nitroquinoline-3-carbonitrile and 8.00 g (31.9 mmol) of 3,4-dibromoaniline in 160 mL of EtOH was refluxed under $N_2$ for 5 hr. Satd $NaHCO_3$ was added and volatile material was removed. The residue was slurried with hexane, collected, washed with hexane and $H_2O$ and dried. The insoluble material was repeatedly extracted with boiling EtOAc and the solution was then filtered through silica gel. The solvent was removed to give 3.80 g of 4-(3,4-dibromophenylamino)-6-nitroquinoline-3-carbonitrile as a green solid: mass spectrum (electrospray, m/e): M+H 448.9.

EXAMPLE 378

6-Amino-4-(3-trifluoromethylphenylamino)quinoline-3-carbonitrile

A mixture of 6.0 g (16.8 mmol) of 6-nitro-4-(3-trifluoromethylphenylamino)quinoline-3-carbonitrile and 18.9 g (83.8 mmol) of $SnCl_2.2H_2O$ in 240 mL of EtOH was refluxed under $N_2$ for 1 hr. Ice water was added followed by $NaHCO_3$ to pH 8. The mixture was stirred for 2 hr and then extracted with $CHCl_3$. Darco was added and the extracts were filtered through anhyd $MgSO_4$ and evaporated. The residue was filtered through silica gel with 10% MeOH in $CHCl_3$. Solvent evaporation and drying in vacuo (40° C.) gave 4.87 g of 6-amino-4-(3-trifluoromethylphenylamino) quinoline-3-carbonitrile as a brown solid: mass spectrum (electrospray, m/e): M+H 329.1.

EXAMPLE 379

6-Amino-4-(3,4-dibromophenylamino)quinoline-3-carbonitrile

Prepared from 4.90 g of 4-(3,4-dibromophenylamino)-6-nitroquinoline-3-carbonitrile and 12.4 g of $SnCl_2.2H_2O$ in the same manner as EXAMPLE 378. There was obtained 1.25 g of 6-amino-4-(3,4-dibromophenylamino)quinoline-3-carbonitrile as a brown solid: mass spectrum (electrospray, m/e): M+H 416.9, 418.9.

EXAMPLE 380

N-[3-Cyano-4-(3,4-dibromophenylamino)quinolin-6-yl]acrylamide

6-Amino-4-(3,4-dibromophenylamino)quinoline-3-carbonitrile (0.750 g. 1.79 mmol) in 10 mL of THF was treated with 0.217 g (2.15 mmol) of $Et_3N$ and 0.195 g (2.15 mmol) of acryloyl chloride at 0° C. under $N_2$. After stirring overnight at 25° C., the solvent was evaporated and the residue was slurried with water and collected. The residue was boiled twice with EtOAc and then dried in vacuo (50° C.) to give 0.609 g of N-[3-cyano-4-(3,4-dibromophenylamino)quinolin-6-yl]acrylamide as a brown solid: mass spectrum (electrospray, m/e): 470.9, 472.9.

EXAMPLE 381

N-[4-(3-Bromophenylamino)-3-cyanoquinolin-6-yl]propionamide

Prepared from 1.00 g of 6-amino-4-(3-bromophenylarnino)quinoline-3-carbonitrile, 0.359 g of $Et_3N$ and 0.328 g of propionyl chloride in the same manner as EXAMPLE 380. The yield of N-[4-(3-bromophenylamino)-3-cyanoquinolin-6-yl]propionamide was 0.722 g as a yellow solid: mass spectrum (electrospray, m/e): M+H 395.1, 397.0.

EXAMPLE 382

(E)-But-2-enoic Acid [4-(3-Bromophenylamino)-3-cyanoquinolin-6-yl]amide

A solution of 0.637 g (7.40 mmol) of E-but-2-enoic acid in 25 mL of THF under $N_2$ was chilled in ice. Isobutyl chloroformate (1.01 g, 7.40 mmol) and N-methylmorpholine (0.747 g, 7.40 mmol) were added and the solution was stirred cold for 10 min. A slurry of 1.00 g (2.96 mmol) of 6-amino-4-(3-bromophenylamino)quinoline-3-carbonitrile in 15 mL of THF was added and the mixture was stirred at 25° C. overnight. The mixture was evaporated and the residue was slurried in water, collected and dried. The residue was boiled twice with EtOAc and dried in vacuo (50° C.) to give 0.965 g of (E)-but-2-enoic acid [4-(3-bromophenylamino)-3-cyanoquinolin-6-yl]amide as a yellow solid: mass spectrum (electrospray, m/e): M+H 406.9, 408.9.

EXAMPLE 383

N-[4-(3-Bromophenylamino)-3-cyanoquinolin-6-yl]-2-methylacrylamide

Prepared from 0.500 g of 6-amino-4-(3-bromophenylamino)quinoline-3-carbonitrile, 0.194 g of $Et_3N$ and 0.202 g of methacryloyl chloride in the same manner as EXAMPLE 380. There was obtained 0.317 g of N-[4-(3-bromophenylamino)-3-cyanoquinolin-6-yl]-2-methylacrylamide as a yellow solid: mass spectrum (electrospray, m/e): M+H 406.8, 408.8.

EXAMPLE 384

4-(3-Fluorophenylamino)-6-nitroquinoline-3-carbonitrile

Prepared from 5.00 g of 4-chloro-6-nitroquinoline-3-carbonitrile and 2.86 g of 3-fluoroaniline in the same manner as EXAMPLE 377. The crude product was dissolved in a large volume of EtOAc, treated with Darco and filtered through Celite. Solvent removal and drying in vacuo (50° C.) gave 5.77 g of 4-(3-fluorophenylamino)-6-nitroquinoline-3-carbonitrile as a yellow-orange solid: mass spectrum (electrospray, m/e): M+H 309.2.

EXAMPLE 385

6-Amino-4-(3-fluorophenylamino)quinoline-3-carbonitrile

Prepared from 5.04 g of 4-(3-fluorophenylamino)-6-nitroquinoline-6-carbonitrile and 18.5 g of $SnCl_2.2H_2O$ in the same manner as EXAMPLE 378. Filtration through silica was unnecessary. There was obtained 4.30 g of 6-amino-4-(3-fluorophenylamino)quinoline-3-carbonitrile as yellow-brown crystals: mass spectrum (electrospray, m/e): M+H 279.1.

EXAMPLE 386

4-(3-Dimethylaminophenylamino)-6-nitroquinoline-3-carbonitrile

Prepared from 5.00 g of 4-chloro-6-nitroquinoline-3-carbonitrile, 5.38 g of 3-dimethylaminoaniline dihydrochloride and 5.17 g of triethylamine in the same manner as EXAMPLE 377. The crude product was taken up in EtOAc, treated with Darco, filtered through Celite, evaporated and dried in vacuo (50° C.). The yield of 4-(3-dimethylaminophenylamino)-6-nitroquinoline-3-carbonitrile was 5.62 g as brick red crystals: mass spectrum (electrospray, m/e): M+H 334.2.

EXAMPLE 387

4-(4-Dimethylaminophenylamino)-6-nitroquinoline-3-carbonitrile

Prepared from 5.00 g of 4-chloro-6-nitroquinoline-3-carbonitrile, 5.38 g of 4-dimethylaminoaniline dihydrochloride and 5.17 g of triethylamine in the same manner as EXAMPLE 386. The yield of 4-(4-dimethylaminophenylamino)-6-nitroquinoline-3-carbonitrile was 5.58 g as brick red crystals: mass spectrum (electrospray, m/e): M+H 334.2.

EXAMPLE 388

6-Amino-4-(3-dimethylaminophenylamino)quinoline-3-carbonitrile

A mixture of 5.00 g (15.0 mmol) of 4-(3-dimethylaminophenylamino)-6-nitro-quinoline-3-carbonitrile, 1.20 g (37.5 mmol) of anhyd hydrazine and 0.5 g of 10% Pd/C in 250 mL of EtOH was refluxed under $N_2$ for 1.3 hr. The reaction was filtered through Celite, the Celite was washed with EtOH and the filtrate and washes were combined. Solvent evaporation and drying in vacuo (50° C.) gave 6-amino-4-(3-dimethylaminophenylamino)quinoline-3-carbonitrile as a red brown solid: mass spectrum (electrospray, m/e): 303.9.

EXAMPLE 389

6-Amino-4-(4-dimethylaminophenylamino)quinoline-3-carbonitrile

Prepared from 4-(4-dimethylaminophenylamino)-6-nitroquinoline-3-carbonitrile (5.00 g), 1.20 g of anhyd hydrazine and 0.500 g of 10% Pd/C in the same manner as EXAMPLE 388 155179. After washing first with MeOH (discarded), the product was eluted with DMF. The latter solvent was collected separately, evaporated and the residue was dried in vacuo (50° C.). The yield of 6-amino-4-(4-dimethylaminophenylamino)quinoline-3-carbonitrile was 4.00 g as a yellow solid: mass spectrum (electrospray, m/e): M+H 303.9.

EXAMPLE 390

But-2-ynoic Acid [4-(3-Fluorophenylamino)-3-cyanoquinolin-6-yl]amide

Prepared from 0.756 g of but-2-ynoic acid, 1.23 g of isobutyl chloroformate, 0.908 g of N-methylmorpholine and 1.00 g of 6-amino-4-(3-fluorophenylamino)quinoline-3-carbonitrile in the same manner as EXAMPLE 382. The yield of but-2-ynoic acid [4-(3-fluorophenylamino)-3-cyanoquinolin-6-yl]amide was 1.07 g as a yellow solid: mass spectrum (electrospray, m/e): 345.1.

EXAMPLE 391

N-[3-Cyano-4-(3-dimethylaminophenylamino)quinolin-6-yl]acrylamide

Prepared from 1.00 g of 6-amino-4-(3-dimethylaminophenylamino)quinoline-3-carbonitrile, 0.400 g of triethylamine and 0.360 g of acryloyl chloride in the same manner as EXAMPLE 88. The yield of N-[3-cyano-4-(3-dimethylaminophenylamino)quinolin-6-yl]acrylamide was 0.880 g as an orange solid: mass spectrum (electrospray, m/e): 358.1.

EXAMPLE 392

N-[3-Cyano-4-(4-dimethylaminophenylamino)quinolin-6-yl]acrylamide

Prepared from 1.00 g of 6-amino-4-(4-dimethylaminophenylamino)quinoline-3-carbonitrile, 0.400 g of triethylamine and 0.360 g of acryloyl chloride in the same manner as EXAMPLE 380. The yield of N-[3-cyano-4-(4-dimethylaminophenylamino)quinolin-6-yl]acrylamide was 0.990 g of brown-orange solid: mass spectrum (electrospray, m/e): 358.2.

EXAMPLE 393

But-2-ynoic Acid [3-Cyano-4-(3-dimethylaminophenylamino)quinolin-6-yl]amide

Prepared from 0.694 g of but-2-ynoic acid, 1.13 g of isobutyl chloroformate, 0.833 g of N-methylmorpholine and 1.00 g of 6-amino-4-(3-dimethylaminophenylamino)quinoline-3-carbonitrile in the same manner as EXAMPLE 382. The yield of but-2-ynoic acid [3-cyano-4-(3-dimethylaminophenylamino)quinolin-6-yl]amide was 0.967 g as an orange solid: mass spectrum (electrospray, m/e): M+H 370.2.

EXAMPLE 394

But-2-ynoic Acid [3-Cyano-4-(4-dimethylaminophenylamino)quinolin-6-y]amide

Prepared from 0.694 g of but-2-ynoic acid, 1.13 g of isobutyl chloroformate, 0.833 g of N-methylmorpholine and 1.00 g of 4-(4-dimethylaminophenylamino)quinoline-3- carbonitrile in the same manner as EXAMPLE 382. The yield of but-2-ynoic acid [3-cyano-4-(4-dimethylaminophenylamino)quinolin-6-yl]amide was 1.13 g as a brick red solid: mass spectrum (electrospray, m/e): M+H 370.2.

EXAMPLE 395

4-(3-Bromophenylamino)-6-dimethylaminoquinoline-3-carbonitrile Hydrochloride Prepared from 0.400 g of 4-chloro-6-dimethylaminoquinoline-3-carbonitrile and 3-bromoaniline in the same manner as EXAMPLE 377. The crude product was boiled twice with EtOAc and dried in vacuo (50° C.). The yield of 4-(3-bromophenylamino)-6-dimethylaminoquinoline-3-carbonitrile hydrochloride was 0.621 g as a brown powder: mass spectrum (electrospray, m/e) M+H 366, 368.9.

EXAMPLE 396

6-Dimethylamino-4-(3-methoxyphenylamino) quinoline-3-carbonitrile Hydrochloride Prepared from 0.400 g of 4-chloro-6-dimethylaminoquinoline-3-carbonitrile and 0.256 g of 3-methoxyaniline in the same manner as EXAMPLE 395. The yield of 6-dimethylamino-4-(3-methoxyphenylamino) quinoline-3-carbonitrile was 0.532 g of brown powder: mass spectrum (electrospray, m/e): M+H 318.9.

EXAMPLE 397

2-Bromo-N-[4-(3-bromophenylamino)-3-cyanoquinolin-6-yl]acetamide

Prepared from 1.50 g of 6-amino-4-(3-bromophenylamino)quinoline-3-carbonitrile, 0.538 g of triethylamine and 1.08 g of bromoacetyl bromide in the same manner as EXAMPLE 380. The yield of 2-bromo-N-[4-(3-bromophenylamino)-3-cyanoquinolin-6-yl]acetamide was 1.55 g as a yellow-brown solid: mass spectrum (electrospray, m/e): M+H 458.9, 460.9.

EXAMPLE 398

6-Iodo-4-(3-methoxyphenylamino)quinoline-3-carbonitrile

Prepared from 1.00 g of 4-chloro-6-iodoquinoline-3-carbonitrile and 0.469 g of 3-methoxyaniline in the same manner as EXAMPLE 377. The crude product was filtered through silica gel with 20% EtOAc in $CH_2Cl_2$, evaporated and dried in vacuo (50° C.). The yield of 6-iodo-4-(3-methoxyphenylamino)quinoline-3-carbonitrile was 1.09 g as yellow crystals: mass spectrum (electrospray, m/e): M+H 401.9.

EXAMPLE 399

4-Dimethylamino-but-2-enoic acid [4-(3-chloro-4-fluoro-phenylamino)-3-cyano-7-ethoxy-quinolin-6-yl]-amide 5-Methoxy-2-methyl-4-nitroacetanilide A solution of 182.1 g (1.0 mol) of 5-methoxy-2-methyl-4-nitroaniline in 400 ml acetic acid was heated to reflux. To the hot solution was added 320 ml of acetic anhydride. The mixture was refluxed for V½ hr and then poured onto ice. The solid was collected and washed twice with water and once with conc. $NH_4OH$ (this step converts any di-acetate to mono-acetate). The solid is then air dried. The solid is dissolved in 1400 ml of boiling chloroform, treated with $MgSO_4$ and Norite, and filtered while hot. The filtrate was boiled and 500 ml of hexanes were added. The mixture was cooled in an ice bath. Solid was collected giving 145.9 g (65%) of the product as an orange solid.

5-Ethoxy-2-methyl-4-nitroacetanilide

A mixture of 186 g (830 mmol) of 5-methoxy-2-methyl-4-nitroacetanilide and 105.5 g (2.49 mol) of LiCl in 1115 ml of DMF was mechanically stirred at reflux for 12 hr without using a condenser. The dark orange solution was allow to cool to room temperature and then allowed to stand overnight. To the stirring solution was added 114.65 g (830 mmol) of powdered $K_2CO_3$ and 265.4 ml (3.32 mol) of ethyl iodide. The mixture was slowly heated with stirring. At about 70¼ C a rapid gas evolution ensues (probably ethyl chloride). After most gas has evolved, heating is continued to reflux temperature. The mixture is refluxed for 5 hr and then poured onto ice water. The solid is collected, washed several times with water, and air dried. The solid is dissolved in 2 L of boiling chloroform, treated with $MgSO_4$, and filtered while hot. The filtrate is boiled and diluted with 1.5 L hexanes. The mixture is cooled and solid is collected giving 105 g of a yellow solid (53%).

2-Acetylamino-4-ethoxy-5-nitro-benzoic acid

A solution of 217.3 g of potassium permanganate and 75.23 g of magnesium sulfate in 5000 ml of water was heated to 80° C. Then 119 g (0.5 moles) of 5-ethoxy-2-methyl-4-nitroacetanilide was added in one portion. Heating at reflux was continued. After about 45 minutes (the disappearance of the permanganate color) an additional 37.62 g of magnesium sulfate and then 108.65 g of potassium permanganate were added. After about 45 minutes of additional reflux (the disappearance of the permanganate color) the reaction was filtered hot. The manganese dioxide cake was reserved. Acidification of the filtrate with concentrated hydrochloric acid gave product. The reserved manganese dioxide was boiled with 2000 ml of water, and filtered. Acidification of the filtrate gave additional product. The products were combined and dried to give 68.19 g (50.8%) of the desired product. Starting material could be extracted from the manganese dioxide cake with acetone.

3-Ethoxy-4-nitroaniline

To 600 ml of H2O was slowly added 400 ml conc. $H_2SO_4$. To the hot mixture was added 118.5 g 0.44 mol)) of 2-acetylamino-4-ethoxy-5-nitro-benzoic acid. The mixture was heated to 110–112° C. with stirring. Initially there was a vigorous gas evolution. After I hr., the mixture was poured unto ice. The mixture was made basic with conc. ammonium hydroxide (an exothermic reaction ensued). The mixture was allowed to cool to room temperature and the solid was collected by filtration. The solid was washed several time with 500 ml portions of water and then dried in vacuum and then extracted several times with warm ethyl acetate. The extracts were filtered and solvent was removed giving 57.8 g (71%) of the product.

2-(2-Cyano-2-ethoxycarbonyl-vinylamino)-4-ethoxy-5-nitro-benzoic Acid

A mixture of 58.96 g (0.324 moles) of 3-ethoxy-4-nitroaniline and 77.22 g (0.456 moles) of ethyl (ethoxymethylene) cyano acetate in 210 ml of toluene was refluxed for about 16 hours (overnight). The reaction was cooled in an ice bath, and the product was filtered. It was washed with three portions of ether, then dried to give 94.33 g (95.8%) of the desired product. This can be recrystallized in about 80% yield from methyl cellosolve.

7-Ethoxy-4-hydroxy-6-nitro-quinoline-3-carbonitrile

The yellow starting material 2-(2-cyano-2-ethoxycarbonyl-vinylamino)-4-ethoxy-5-nitro-benzoic acid (37.5 g, 0.123 mol), which had been recrystallized from 2-methoxyethanol, was added as a solid to 2.5L of refluxing (256° C.) Dowtherm in a 5L three-necked flask equipped with a mechanical stirrer and a thermometer under nitrogen. The reaction mixture was stirred vigorously at this temperature for 1.25 hrs, and then allowed to cool to room temperature. The thick reaction mixture was diluted with 2L of ether, filtered and washed with ether to yield 24.2 g of the cyclized product 7-ethoxy-4-hydroxy-6-nitro-quinoline-3-carbonitrile as an off-white solid with a yield of 76%.

The filtrate was evaporated to remove ether and then treated with hexane. The resulting yellow precipitate was collected and washed with hexane to yield 10~15% unreacted starting material, which could be recycled to generate more cyclized product. The resulting filtrate was evaporated to remove hexane and then passed through a thin pad of silica gel to remove colored impurities to regenerate the Dowtherm for more cyclization reactions.

4-Chloro-7-ethoxy-6-nitro-quinoline-3-carbonitrile

In a 1L round-bottomed flask, the nitro compound 7-ethoxy-4-hydroxy-6-nitro-quinoline-3-carbonitrile (20 g, 77 mmol) was refluxed with 120 ml of phosphorus oxychloride under nitrogen for 2.5 hrs. TLC (ethyl acetate: hexane=1:1) showed no starting material left. The volatile reagents were removed by rotary evaporation and further azeotropically removed with toluene at 50° C. The flask containing the solid residue was cooled in an ice bath, and 600 ml of methylene chloride was added to dissolve the residue. The resulting cold methylene chloride solution was added into a vigorously stirred solution of 250 ml ice-cold saturated potassium carbonate solution (53.3 g, 5 eq) and stirred for 30 min. The organic layer was separated, washed and dried to give 18.58 g of 4-chloro-7-ethoxy-6-nitro-quinoline-3-carbonitrile with a yield of 86.9%.

4-(3-Chloro-4-fluoro-phenylamino)-7-ethoxy-6-nitro-quinoline-3-carbonitrile

4-Chloro-7-ethoxy-6-nitro-quinoline-3-carbonitrile (26.8 g 96.5 mmol) and 3-chloro-4-fluoroaniline 14.05 g 96.5 mmol) in 900 ml of iso-propanaol were refluxed under $N_2$ for 3.5 hrs. TLC (ethyl acetate: hexane=1:1) showed no starting material left. After standing at room temperature overnight, the hydrochloride salt was filtered off and washed with isopropanol and ether giving 4-(3-chloro-4-fluoro-phenylamino)-7-ethoxy-6-nitro-quinoline-3-carbonitrile 38.6 g (95%) as a yellow hydrochloride salt.

6-Amino-4-(3-chloro-4-fluoro-phenylamino)-7-ethoxy-quinoline-3-carbonitrile 4-(3-Chloro-4-fluoro-phenylamino)-7-ethoxy-6-nitro-quinoline-3-carbonitrile hydrochloride (38.6 g 91.2 mmol) was mixed with 35.7 g (638 mmol) of iron powder. A solution of 43.9 g (820 mmol) of ammonium chloride in 280 ml of water was added followed by 985 ml of methanol. The mixture was reflux with mechanical stirring under nitrogen for 4 hr at which time TLC indicated complete reduction. The reaction mixture was filtered hot and solids were washed with 500 ml of boiling methanol. After the combined filtrate was evaporated, the residue was partitioned between 1.5L of warm ethyl acetate and 700 ml of saturated sodium bicarbonate solution. The organic layer was dried over magnesium sulfate, treated with Norite, filtered and evaporated to give a solid which was recrystallized from $CHCl_3$-hexanes giving 29.0 g (89%) of 6-amino-4-(3-chloro-4-fluoro-phenylamino)-7-ethoxy-quinoline-3-carbonitrile as a light green solid.

4-Bromo-but-2-enoic acid [4-(3-chloro-4-fluoro-phenylamino)-3-cyano-quinolin-6-yl]-amide To 14.98 g (63.17 mmol) of trimethylsilyl 4-bromo-2-butenoate (prep.: *Synthesis* 745 1983) in 36 ml of methylene chloride, was added 8.82 g (69.5 mmol) of oxalyl chloride, followed by 1 drop of dried DMF. After the solution was stirred for 2 hr, the solvent was evaporated, and further azeotropically distilled with carobon tetrachloride to yield the acid chloride. 6-Amino-4-(3-chloro-4-fluoro-phenylamino)-7-ethoxy-quinoline-3-carbonitrile (19.6 g, 54.9 mmol) was mixed with 11.46 ml (65.91 mmol) of N,N-diisopropylethylamine in 366 ml of anhydrous THF under nitrogen in an ice bath. A solution of the acid chloride prepared above in 183 ml of THF was added over 15 minutes, and then stirred for half an hour at 0° C. The reaction vessel was sealed and stored in the freezer overnight. The reaction solution was rotary evaporated and the residue was partitioned between saturated sodium bicarbonate and ethyl acetate. The organic layer was separated, washed, dried with magnesium sulfate and passed through a thin layer of silica gel to give 32 g of the crude product as an orange solid. The crude product was refluxed with 400 ml of methanol for half an hour. After cooling to room temperature, the solid was collected and washed with methanol followed by hexane to give 21.3 g of beige solid with a yield of 76.5%. It is a mixture of the bromo and chloro compounds. More product could be isolated from the mother liquor.

4-Dimethylamino-but-2-enoic acid [4-(3-chloro-4-fluoro-phenylamino)-3-cyano-7-ethoxy-quinolin-6-yl]-amide The bromo/chloro compounds (19.88 g, 39.53 mmol) were dissolved in 800 ml of THF at 0° C. and 2 equivalent of 2M dimethylamine (39.54 ml, 79.07 mmol) in THF was added in one portion. The reaction solution was stirred at room temperature overnight. Another equivalent of dimethylamine was added. After stirring overnight at room temperature, only 10% of chloro compound was unreacted. The reaction solution was rotary evaporated and the residue was partitioned between ethyl acetate and saturated potassium bicarbonate. The organic layer was dried, filtered and evaporated to give 17 g of orange glass. The crude product was taken up in acetone and purified by column chromatography using acetone as the eluant. The main fractions were pooled and evaporated to give 9.8 g of a yellow glass. It was then dissolved in 350 ml of hot ethyl acetate and evaporated to a concentrated solution. A few drops of methanol was added to assist recrystallization. After standing at room temperature overnight, the beige crystals were filtered to yield 7.09 g of pure 4-dimethylamino-but-2-enoic acid [4-(3-chloro-4-fluoro-phenylamino)-3-cyano-7-ethoxy-quinolin-6-yl]-amide (mp 196–198° C.) with a yield of 38.7%. A lot of product remained in the mother liquors in the steps of chromatography and recrystallization, and could be isolated. The expected yield is about 60%.

We claim:

1. A method of treating or inhibiting colonic polyps in a mammal susceptible to the formation of colonic polyps which comprises providing to said mammal an effective amount of a compound of the formula

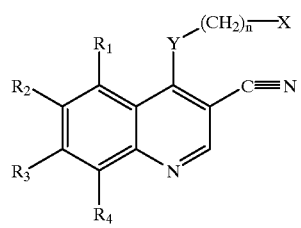

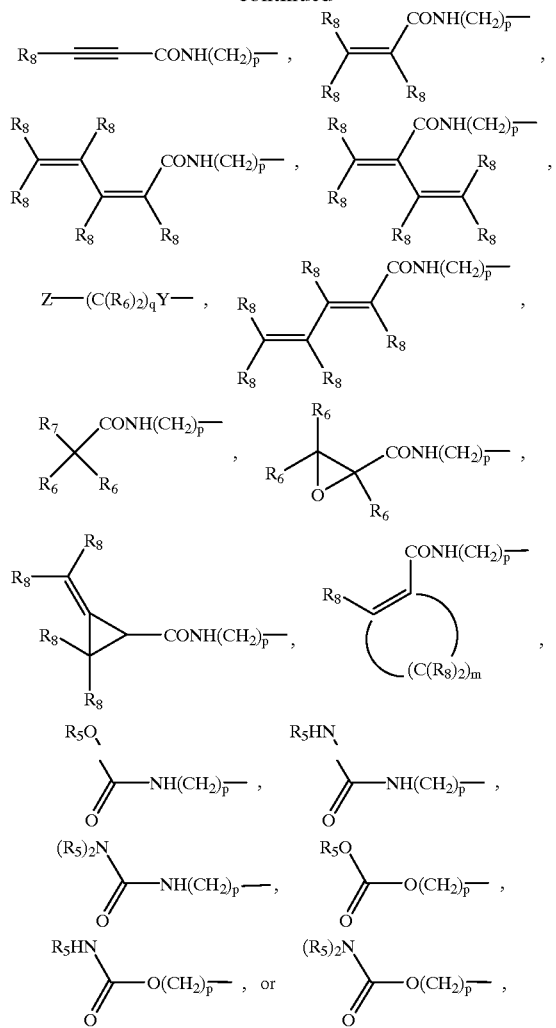

wherein:

X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino, $R_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

$R_6$ is hydrogen, alkyl of 1–6 carbon atoms, or alkenyl of 2–6 carbon atoms;

$R_7$ is chloro or bromo $R_8$ is hydrogen, alkyl of 1–6 carbon atoms, aminoalkyl of 1–6 cabon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents $R_1$, $R_2$, $R_3$, or $R_4$ that are located on contiguous carbon atoms can together be the divalent radical —O—C($R_8$)$_2$—O—;

or a pharmaceutically acceptable salt thereof with the proviso that when Y is —NH—, $R_1$, $R_2$, $R_3$, and $R_4$ are hydrogen, and n is 0, X is not 2-methylphenyl.

2. The method according to claim 1 wherein Y is —NH— and n=0 or a pharmaceutically acceptable salt thereof.

3. The method according to claim 2 wherein X is optionally substituted phenyl or a pharmaceutically acceptable salt thereof.

4. The method according to claim 3 wherein $R_1$ and $R_4$ are hydrogen or a pharmaceutically acceptable salt thereof.

5. The method according to claim 1 in which 4-[(3-bromophenyl)amino]-6,7-diethoxy-3-quinolinecarbonitrile or a pharmaceutically acceptable salt thereof is provided.

6. The method according to claim 1 in which 4-dimethylamino-but-2-enoic acid [4-(3-chloro-4-fluorophenylamino)-3-cyano-7-methoxy-quinolin-6-yl]-amide or a pharmaceutically acceptable salt thereof is provided.

7. The method according to claim 1 in which 4-diethylamino-but-2-enoic acid [4-(3-chloro-4-fluorophenylamino)-3-cyano-7-methoxy-quinolin-6-yl]-amide or a pharmaceutically acceptable salt thereof is provided.

8. The method according to claim 1 in which 4-dimethylamino-but-2-enoic acid [4-(3-bromo-4-fluorophenylamino)-3-cyano-7-methoxy-quinolin-6-yl]-amide or a pharmaceutically acceptable salt thereof is provided.

9. The method according to claim 1 in which 4-dimethylamino-but-2-enoic acid [4-(3-bromophenylamino)-3-cyano-7-ethoxy-quinolin-6-yl]-amide or a pharmaceutically acceptable salt thereof is provided.

10. The method according to claim 1 in which 4-diethylamino-but-2-enoic acid [4-(3-bromophenylamino)-3-cyano-7-ethoxy-quinolin-6-yl]-amide or a pharmaceutically acceptable salt thereof is provided.

11. The method according to claim 1 in which 4-morpholin-4-yl-but-2-enoic acid [4-(3-chloro-4-fluorophenylamino)-3-cyano-7-methoxy-quinolin-6-yl]-amide or a pharmaceutically acceptable salt thereof is provided.

12. The method according to claim 1 in which 4-dimethylamino-but-2-enoic acid [4-(3-bromophenylamino)-3-cyano-7-methoxy-quinolin-6-yl]-amide or a pharmaceutically acceptable salt thereof is provided.

13. The method according to claim 1 in which N-[4-[(3-bromophenyl)amino]-3-cyano-6-quinolinyl]-4-methoxy-2-butynamide or a pharmaceutically acceptable salt thereof is provided.

14. The method according to claim 1 in which N-{4-[(3-chloro-4-fluorophenyl)amino]-3-cyano-6-quinolinyl}-4-dimethylamino-2-butenamide or a pharmaceutically acceptable salt thereof is provided.

15. The method according to claim 1 in which 4-dimethylamino-but-2-enoic acid [4-(3-chloro-4-fluorophenylamino)-3-cyano-7-ethoxy-quinolin-6-yl]-amide or a pharmaceutically acceptable salt thereof is provided.

16. The method according to claim 1 in which a) 4-[(3-bromophenyl)amino]-7-methoxy-3-quinolinecarbonitrile;

b) 4-[(3-bromophenyl)amino]-7-methoxy-6-nitro-3-quinolinecarbonitrile;

c) 6-amino-4-[(3-bromophenyl)amino]-7-methoxy-3-quinolinecarbonitrile;

d) N-[4-[(3-bromophenyl)amino]-3-cyano-7-methoxy-6-quinolinyl]-2-butynamide;

e) N-[4-[(3-bromophenyl)amino]-3-cyano-7-methoxy-6-quinolinyl]-2-propenamide;

f) 4-[(3-bromophenyl)amino]-6-nitro-3-quinolinecarbonitrile;

g) 6-amino-4-[(3-bromophenyl)amino]-3-quinolinecarbonitrile;

h) N-[4-[(3-bromophenyl)amino]-3-cyano-6-quinolinyl]-2-butynamide;

i) N-[4-[(3-bromophenyl)amino]-3-cyano-6-quinolinyl] acetamide;

j) N-[4-[(3-bromophenyl)amino]-3-cyano-6-quinolinyl] butanamide;

k) N-[4-[(3-bromophenyl)amino]-3-cyano-6-quinolinyl]-2-propenamide;

l) N-[4-[(3-bromophenyl)amino]-3-cyano-6-quinolinyl]-2-chloroacetamide;

m) 4-[(3,4-dibromophenyl)amino]-6-nitro-3-quinolinecarbonitrile;

n) 6-amino-4-[(3,4-dibromophenyl)amino]-3-quinolinecarbonitrile;

o) N-[4-[(3,4-dibromophenyl)amino]-3-cyano-6-quinolinyl]-2-butynamide;

p) 6-nitro-4-[(3-trifluoromethylphenyl)amino]-3-quinolinecarbonitrile;

q) 6-amino-4-[(3-trifluoromethylphenyl)amino]-3-quinolinecarbonitrile;

r) N-[4-[(3-trifluoromethylphenyl)amino]-3-cyano-6-quinolinyl]-2-butynamide;

s) 4-[(3-bromophenyl)amino]-6,7-dimethoxy-3-quinolinecarbonitrile;

t) 4-[(3-fluorophenyl)amino]-6,7-dimethoxy-3-quinolinecarbonitrile;

u) 4-(cyclohexyamino)-6,7-dimethoxy-3-quinolinecarbonitrile;

v) 4-[(3-bromophenyl)amino]-6,7-dihydroxy-3-quinolinecarbonitrile;

w) 8-[(3-bromophenyl)amino]-[1,3]-dioxolo[4,5-g]quinoline-7-carbonitrile;

x) 4-[(3-chlorophenyl)amino]-6,7-dimethoxy-3-quinolinecarbonitrile;

y) 4-[(3-trifluoromethylphenyl)amino]-6,7-dimethoxy-3-quinolinecarbonitrile;

z) 4-[(3,4-dimethoxyphenyl)amino]-6,7-dimethoxy-3-quinolinecarbonitrile;

aa) 4-[(methylphenyl)amino]-6,7-dimethoxy-3-quinolinecarbonitrile;

bb) 4-[(3-cyanophenyl)amino]-6,7-dimethoxy-3-quinolinecarbonitrile;

cc) 4-[(4-fluorophenyl)amino]-6,7-dimethoxy-3-quinolinecarbonitrile;

dd) 4-[(3-(hydroxymethyl)phenyl)amino]-6,7-dimethoxy-3-quinolinecarbonitrile;

ee) 4-(3-bromophenoxy)-6,7-dimethoxy-3-quinolinecarbonitrile;

ff) 4-[(4-bromophenyl)sulfanyl]-6,7-dimethoxy-3-quinolinecarbonitrile;

gg) N-[4-[(3-bromophenyl)amino]-3-cyano-6-quinolinyl]-3(E)-chloro-2-propenamide;

hh) N-[4-[(3-bromophenyl)amino]-3-cyano-6-quinolinyl]-3(Z)-chloro-2-propenamide;
ii) N-[4-[(3-bromophenyl)amino]-3-cyano-6-quinolinyl]-2-methyl-2-propenamide;
jj) N-[4-[(3,4-dibromophenyl)amino]-3-cyano-6-quinolinyl]-2-propenamide;
kk) N-[4-[(5-bromo-3-pyridinyl)amino]-6,7-dimethoxy-3-quinolinecarbonitrile;
ll) 4-[(3-bromophenyl)amino]-6,7-bis(methoxymethoxy)-3-quinolinecarbonitrile;
mm) N-[4-[(3-bromophenyl)amino]-3-cyano-6-quinolinyl]-4-hydroxy-2-butynamide;
nn) N-[4-[(3-bromophenyl)amino]-3-cyano-6-quinolinyl]-4-morpholino-2-butynamide;
oo) N-[4-[(3-bromophenyl)amino]-3-cyano-6-quinolinyl]-4-dimethylamino-2-butynamide;
pp) N-[4-[(3-bromophenyl)amino]-3-cyano-6-quinolinyl]-4-methoxy-2-butynamide;
qq) 4-(3-bromophenylmethylamino)-6,7-diethoxy-3-quinolinecarbonitrile;
rr) 4-(3-phenylmethylamino)-6,7-diethoxy-3-quinolinecarbonitrile;
ss) 4-(3,4-dimethoxyphenylmethylamino)-6,7-diethoxy-3-quinolinecarbonitrile;
tt) 4-(3,4-dichlorophenylmethylamino)-6,7-diethoxy-3-quinolinecarbonitrile;
uu) 4-methoxy-but-2-enoic acid [4-(3-bromo-phenylamino)-3-cyano-quinolin-6-yl]-amide;
vv) 4-(4-chloro-2-fluoro-phenylamino)-7-(3-chloro-propoxy)-6-methoxy-quinoline-3-carbonitrile;
ww) 4-(4-chloro-2-fluoro-phenylamino)-6-methoxy-7-(3-morpholin-4-yl-propoxy)-quinoline-3-carbonitrile;
xx) 7-(2-dimethylamino-ethoxy)-4-(3-hydroxy-4-methyl-phenylamino)-6-methoxy-quinoline-3-carbonitrile;
yy) 4-(3-hydroxy-4-methyl-phenylamino)-6-methoxy-7-(2-morpholin-4-yl-ethoxy)-quinoline-3-carbonitrile; or
zz) 4-(4-chloro-2-fluoro-5-hydroxy-phenylamino)-7-(3-dimethylamino-propoxy)-6-methoxy-quinoline-3-carbonitrile;

or a pharmaceutically acceptable salt thereof is provided.

17. The method according to claim 1 in which
a) 4-(4-chloro-2-fluoro-5-hydroxy-phenylamino)-6-methoxy-7-(3-morpholin-4-yl-propoxy)-quinoline-3-carbonitrile;
b) 4-(4-chloro-2-fluoro-5-hydroxy-phenylamino)-7-(2-dimethylamino-ethoxy)-6-methoxy-quinoline-3-carbonitrile;
c) 4-(4-chloro-2-fluoro-5-hydroxy-phenylamino)-6-methoxy-7-(2-morpholin-4-yl-ethoxy)-quinoline-3-carbonitrile;
d) N-[3-cyano-4-(3-fluorophenylamino)quinolin-6-yl] acrylamide;
e) 6,7-dimethoxy-4-(3-nitrophenylamino)quinoline-3-carbonitrile;
f) 4-(3-bromophenylamino)-6-ethoxy-7-methoxyquinoline-3-carbonitrile;
g) 6-ethoxy-4-(3-hydroxy-4-methylphenylamino)-7-methoxyquinoline-3-carbonitrile;
h) 4-dimethylamino-but-2-enoic acid [4-(3-bromo-phenylamino)-3-cyano-quinolin-6-yl]-amide;
i) 4-diethylamino-but-2-enoic acid [4-(3-bromo-phenylamino)-3-cyano-quinolin-6-yl]-amide;
j) 4-rmethylamino-but-2-enoic acid [4-(3-bromo-phenylamino)-3-cyano-quinolin-6-yl]-amide;
k) 4-[(3-bromophenyl)amino]-8-methyl-6-nitro-3-quinolinecarbonitrile;
l) 4-[(3-bromophenyl)amino]-8-dimethylaminomethyl-6-nitro-3-quinolinecarbonitrile;
m) 6-amino-4-[(3-bromophenyl)amino]-8-dimethylaminomethyl-3-quinolinecarbonitrile;
n) N-{4-[(3-bromophenyl)amino]-3-cyano-8-dimethylaminomethyl-6-quinolinyl}-2-butynamide;
o) N-{4-[(3-bromophenyl)amino]-3-cyano-8-dimethylaminomethyl-6-quinolinyl}-2-propenamide;
p) N-{4-[(3-bromophenyl)amino]-3-cyano-8-dimethylaminomethyl-6-quinolinyl}acetamide;
q) 4-[(3-chloro-4-fluorophenyl)amino]-7-methoxy-6-(morpholinopropoxy)-3-quinolinecarbonitrile;
r) 4-[(3-bromophenyl)amino]-7-methoxy-6-(morpholinopropoxy)-3-quinolinecarbonitrile;
s) 4-[(4-chloro-2-fluorophenyl)amino]-7-methoxy-6-(morpholinopropoxy)-3-quinolinecarbonitrile;
t) 4-[(3-hydroxy-4-methylphenyl)amino]-7-methoxy-6-(morpholinopropoxy)-3-quinolinecarbonitrile;
u) N-{3-cyano-4-[(3-iodophenyl)amino]-6-quinolinyl}-2-propenamide;
v) 6-amino-4-[(3-iodophenyl)amino]-3-quinolinecarbonitrile;
w) 4-[(3-iodophenyl)amino]-6-nitro-3-quinolinecarbonitrile;
x) N-{3-cyano-4-[(3-methylphenyl)amino]-6-quinolinyl}-2-butynamide;
y) 6-amino-4-[(3-methylphenyl)amino]-3-quinolinecarbonitrile;
z) 6-nitro-4-[(3-methylphenyl)amino]-3-quinolinecarbonitrile;
aa) N-{4-[(3-chlorophenyl)amino]-3-cyano-6-quinolinyl}-2-propenamide;
bb) 6-amino-4-[(3-chlorophenyl)amino]-3-quinolinecarbonitrile;
cc) 4-[(3-chlorophenyl)amino]-6-nitro-3-quinolinecarbonitrile;
dd) N-{3-cyano-4-[(3-methoxyphenyl)amino]-6-quinolinyl}-2-propenamide;
ee) N-{3-cyano-4-[(3-methoxyphenyl)amino]-6-quinolinyl}-2-butynamide;
ff) N-{3-cyano-4-[(3-methoxyphenyl)amino]-6-quinolinyl}-4-piperidino-2-butynamide;
gg) 6-amino-4-[(3-methoxyphenyl)amino]-3-quinolinecarbonitrile;
hh) 4-[(3-methoxyphenyl)amino]-6-nitro-3-quinolinecarbonitrile;
ii) N-{4-[(3-chloro-4-fluoro-phenyl)amino]-3-cyano-6-quinolinyl}-2-butynamide;
jj) N-{4-[(3-chloro-4-fluorophenyl)amino]-3-cyano-6-quinolinyl}-2-propenamide;
kk) N-{4-[(3-chloro-4-fluorophenyl)amino]-3-cyano-6-quinolinyl}-4-diethylamino-2-butenamide;
ll) N-{4-[(3-chloro-4-fluorophenyl)amino]-3-cyano-6-quinolinyl}-4-morpholino-2-butenamide;
mm) N-{4-[(3-chloro-4-fluorophenyl)amino]-3-cyano-6-quinolinyl}-2-morpholin-4-ylmethyl-2-propenamide;
nn) 6-amino-4-[(3-chloro-4-fluorophenyl)amino]-3-quinolinecarbonitrile;

oo) 4-[(3-chloro-4-fluorophenyl)amino]-6-nitro-3-quinolinecarbonitrile;

pp) N-{4-[(4-bromophenyl)amino]-3-cyano-6-quinolinyl}-2-propenamide;

qq) 6-amino-4-[(4-bromophenyl)amino]-3-quinolinecarbonitrile;

rr) [(4-bromophenyl)amino]-6-nitro-3-quinolinecarbonitrile;

ss) N-{3-cyano-4-[(3,4-difluorophenyl)amino]-6-quinolinyl]-2-propenamide;

tt) 6-amino-4-[(3,4-difluorophenyl)amino]-3-quinolinecarbonitrile;

uu) 4-[(3,4-difluorophenyl)amino]-6-nitro-3-quinolinecarbonitrile;

ww) N-{4-[(3-chloro-4-thiophenoxyphenyl)amino]-3-cyano-6-quinolinyl}-2-butynamide;

xx) 6-amino-4-[(3-chloro-4-thiophenoxyphenyl)amino]-3-quinolinecarbonitrile;

yy) 4-[(3-chloro-4-thiophenoxyphenyl)amino]-6-nitro-3-quinolinecarbonitrile; or zz) N-{3-cyano-4-[(3-cyanophenyl)amino]-6-quinolinyl}-2-propenamide;

or a pharmaceutically acceptable salt thereof.

18. The method according to claim 1 in which a) N-{3-cyano-4-[(3-cyanophenyl)amino]-6-quinolinyl}-4-piperidino-2-butynamide;

b) 6-amino-4-[(3-cyanophenyl)amino]-3-quinolinecarbonitrile;

c) 4-[(3-cyanophenyl)amino]-6-nitro-3-quinolinecarbonitrile;

d) N-{3-cyano-4-[(3-ethynylphenyl)amino]-6-quinolinyl}-2-butynamide;

e) N-{3-cyano-4-[(3-ethynylphenyl)amino]-6-quinolinyl}-2-propenamide;

f) N-{3-cyano-4-[(3-ethynylphenyl)amino]-6-quinolinyl}-4-piperidino-2-butynamide;

g) 6-amino-4-[(3-ethynylphenyl)amino]-3-quinolinecarbonitrile;

h) 4-[(3-ethynylphenyl)amino]-6-nitro-3-quinolinecarbonitrile;

I) N-{4-[(3-bromophenyl)amino]-3-cyano-6-quinolinyl}-4-piperidino-2-butynamide;

j) N-{4-[(3-bromophenyl)amino]-3-cyano-6-quinolinyl}-4-dipropylamino-2-butynamide;

k) N-{4-[(3-bromophenyl)amino]-3-cyano-6-quinolinyl}-2-morpholin-4-ylmethyl-2-propenamide;

l) N-{4-[(3-bromo-4-fluorophenyl)amino]-3-cyano-6-quinolinyl}-4-dimethylamino-2-butenamide;

m) N-{4-[(3-bromo-4-fluorophenyl)amino]-3-cyano-6-quinolinyl}-4-diethylamino-2-butenamide;

n) N-{4-[(3-bromo-4-fluorophenyl)amino]-3-cyano-6-quinolinyl}-4-morpholino-2-butenamide;

o) N-{4-[(3-bromo-4-fluorophenyl)amino]-3-cyano-7-methoxy-6-quinolinyl}-4-morpholino-2-butenamide;

p) 4-[(3-bromophenyl)amino]-7-ethoxy-6-methoxy-3-quinolinecarbonitrile;

q) 7-ethoxy-4-[(3-hydroxy-4-methylphenyl)amino]-6-methoxy-3-quinolinecarbonitrile;

r) N-[4-[(3-chloro-4-fluorophenyl)amino]-3-cyano-6-quinolinyl]-4-dimethylamino-(z)-2-butenamide;

s) N-[4-[(3-chloro-4-fluorophenyl)amino]-3-cyano-6-quinolinyl]-4-methoxy-(z)-2-butenamide;

t) 4-[[4-[(3-bromophenyl)amino]-3-cyano-6-quinolinyl]amino]-2-methylene-4-oxo-butanoic acid;

u) N-[4-[(3-bromophenyl)amino]-3-cyano-6-quinolinyl]-4-diethylamino-2-butynamide;

v) N-[4-[(3-bromophenyl)amino]-3-cyano-6-quinolinyl]-4-(n-ethylpiperazino)-2-butynamide;

w) N-[4-[(3-chloro-4-fluorophenyl)amino]-3-cyano-6-quinolinyl]-4-diethylamino-2-butynamide;

x) N-[4-[(3-bromophenyl)amino]-3-cyano-6-quinolinyl]-4-(n-methylpiperazino)-2-butynamide;

y) N-[4-[(3-bromophenyl)amino]-3-cyano-6-quinolinyl]-4-(n-isopropyl-n-methylamino)-2-butynamide;

z) N-[4-[(3-bromophenyl)amino]-3-cyano-6-quinolinyl]-4-diisopropylamino-2-butynamide;

aa) N-[4-[(3-chloro-4-fluorophenyl)amino]-3-cyano-6-quinolinyl]-4-dimethylamino-2-butynamide;

bb) N-[4-[-(3-chloro-4-fluorophenyl)amino]-3-cyano-6-quinolinyl]-4-methoxy-2-butynamide;

cc) 4-[(3-bromo-4-fluorophenyl)amino]-6-nitro-3-quinolinecarbonitrile;

dd) 6-amino-4-[(3-bromo-4-fluorophenyl)amino]-3-quinolinecarbonitrile;

ee) N-[4-[(3-bromo-4-fluorophenyl)amino]-3-cyano-6-quinolinyl]-4-dimethylamino-2-butynamide;

ff) 4-diethylamino-but-2-enoic acid [4-(3-bromo-phenylamino)-3-cyano-7-methoxy-quinolin-6-yl]-amide;

gg) 4-morpholin-4-yl-but-2-enoic acid [4-(3-bromo-phenylamino)-3-cyano-7-methoxy-quinolin-6-yl]-amide;

hh) 4-(3-chloro-4-fluoro-phenylamino)-7-methoxy-6-nitro-quinoline-3-carbonitrile;

ii) 6-amino-4-(3-chloro-4-fluoro-phenylamino)-7-methoxy-quinoline-3-carbonitrile;

jj) 4-(3-bromo-4-fluoro-phenylamino)-7-methoxy-6-nitro-quinoline-3-carbonitrile;

kk) 6-amino-4-(3-bromo-4-fluoro-phenylamino)-7-methoxy-quinoline-3-carbonitrile;

ll) 4-diethylamino-but-2-enoic acid [4-(3-bromo-4-fluorophenylamino)-3-cyano-7-methoxy-quinolin-6-yl]-amide;

mm) 4-(3-bromo-phenylamino)-7-ethoxy-6-nitro-quinoline-3-carbonitrile;

nn) 6-amino4-(3-bromo-phenylamino)-7-ethoxy-quinoline-3-carbonitrile;

oo) 4-bromo-but-2-enoic acid [4-(3-bromo-phenylamino)3-cyano-7-ethoxy-quinolin-6-yl]-amide;

pp) 4-morpholin-4-yl-but-2-enoic acid [4-(3-bromo-phenylamino)-3-cyano-7-ethoxy-quinolin-6-yl]-amide;

qq) 6-amino-4-(3-bromo-phenylamino)-8-methoxy-quinoline-3-carbonitrile;

rr) 6-amino-4-(3-bromo-phenylamino)-8-methoxy-quinoline-3-carbonitrile;

ss) 4-bromo-but-2-enoic acid [4-(3-bromo-phenylamino)-3-cyano-8-methoxy-quinolin-6-yl]-amide;

tt) 4-dimethylamino-but-2-enoic acid [4-(3-bromo-phenylamino)-3-cyano-8-methoxy-quinolin-6-yl]-amide;

uu) 4-diethylamino-but-2-enoic acid [4-(3-bromo-phenylamino)-3-cyano-8-methoxy-quinolin-6-yl]-amide;

vv) 4-morpholin-4-yl-but-2-enoic acid [4-(3-bromo-phenylamino)-3-cyano-8-methoxy-quinolin-6-yl]-amide;

ww) 4-dimethylamino-but-2-ynoic acid [4-(3-bromo-phenylamino)-3-cyano-7-methoxy-quinol-6-yl]-amide;

xx) 4-(4-chloro-2-fluoro-phenylamino)-6,7-dimethoxy-quinoline-3-carbonitrile;

yy) 4-(3-hydroxy-4-methyl-phenylamino)-6,7-dimethoxy-quinoline-3-carbonitrile; or zz) 4-(3-dimethylamino-phenylamino)-6,7,8-trimethoxy-quinoline-3-carbonitrile;

or a pharmaceutically acceptable salt thereof is provided.

19. The method according to claim 1 in which a) 4-(3-hydroxy-4-methyl-phenylamino)-6,7,8-trimethoxy-quinoline-3-carbonitrile;

b) 4-(4-chloro-2-fluoro-phenylamino)-6,7,8-trimethoxy-quinoline-3-carbonitrile;

c) 4-(4-chloro-2-fluoro-phenylamino)-5,8-dimethoxy-quinoline-3-carbonitrile;

d) 4-(3-hydroxy-4-methyl-phenylamino)-5,8-dimethoxy-quinoline-3-carbonitrile;

e) 4-(3-bromo-phenylamino)-5,8-dimethoxy-quinoline-3-carbonitrile;

f) 4-(3-bromo-phenylamino)-6,7,8-trimethoxy-quinoline-3-carbonitrile;

g) 4-(3-dimethylamino-phenylamino)-5,8-dimethoxy-quinoline-3-carbonitrile;

h) 4-(4-chloro-2-fluoro-5-hydroxy-phenylamino)-5,8-dimethoxy-quinoline-3-carbonitrile;

i) 4-(4-chloro-2-fluoro-5-hydroxy-phenylamino)-6,7,8-trimethoxy-quinoline-3-carbonitrile;

j) 4-(3-hydroxy-2-methyl-phenylamino)-6,7-dimethoxy-quinoline-3-carbonitrile;

k) 4-(2-hydroxy-6-methyl-phenylamino)-6,7-dimethoxy-quinoline-3-carbonitrile;

l) 4-(3-bromo-4-methyl-phenylamino)-6,7-dimethoxy-quinoline-3-carbonitrile;

m) 4-(3-chloro-4-hydroxy-phenylamino)-6,7-dimethoxy-quinoline-3-carbonitrile;

n) 6,7-dimethoxy-4-(2-methylsulfanyl-phenylamino)-quinoline-3-carbonitrile;

o) 1,4-dihydroquinoline-6,7-diethoxy-4-oxo-3-carbonitrile;

p) 4-[3-chloro-4-(phenylthio)phenylamino]-6,7-diethoxy-3-quinolinecarbonitrile;

q) 4-[3-chloro-4-(phenylthio)phenylamino]-6,7-dimethoxy-3-quinolinecarbonitrile;

r) 4-(3-chloro-4-fluorophenylamino)-6,7-diethoxy-3-quinolinecarborntrile;

s) 4-(3-acetylphenylamino)-6,7-diethoxy-3-quinolinecarbonitrile;

t) 4-(n-methylphenylamino)-6,7-diethoxy-3-quinolinecarbonitrile;

u) 4-(phenylamino)-6,7-diethoxy-3-quinolinecarborntrile;

v) 4-(4-fluorophenylamino)-6,7-diethoxy-3-quinolinecarbonitrile;

w) 4-(4-fluoro-2-methylphenylamino)-6,7-diethoxy-3-quinolinecarbonitrile;

x) 4-(3-chlorophenylamino)-6,7-diethoxy-3-quinolinecarbonitrile;

y) 4-(3-fluorophenylamino)-6,7-diethoxy-3-quinolinecarbonitrile;

z) 4-(3-aminophenylamino)-6,7-dimnethoxy-3-quinolinecarbonitrile;

aa) 4-(3-acetamidopbenylamino)-6,7-dimethoxy-3-quinolinecarbonitrile;

bb) 4-[3-(2-butynoylamino)phienylamino)]-6,7-dimethoxy-3-quinolinecarbonitrile;

cc) 4-[3-(hydroxymethyl)phenylamino]-6,7-dimetboxy-3-quinolinecarbonitrile;

dd) 4-[3-(chloromethyl)phenylamino]-6,7-dimethoxy-3-quinolinecarbonitrile;

ee) 4-[3-(acetylthiomethyl)phenylamino]-6,7-dimethoxy-3-quinolinecarbonitrile;

ff) 4-[3-(thiomethyl)phenylamino]-6,7-dimethoxy-3-quinolinecarbonitrile;

gg) 4-[(3-bromophenyl)amino]-8-methoxy-3-quinolinecarbonitrile;

hh) 4-(4-chloro-2-fluoro-phenylamino)-8-methoxy-quinoline-3-carbonitrile;

ii) 4-(3-hydroxy-4-methyl-phenylamino)-8-methoxy-quinoline-3-carbonitrile;

ii) 4-(3-dimethylamino-phenylamino)-8-methoxy-quinoline-3-carbonitrile;

kk) 4-(4-bromo-3-hydroxy-phenylamino)-8-methoxy-quinoline-3-carbonitrile;

ll) 4-(3-hydroxy-4-methoxy-phenylamino)-8-methoxy-quinoline-3-carbonitrile;

mm) 8-methoxy-4-(2,4,6-trifluoro-phenylamino)-quinoline-3-carbonitrile;

nn) 4-(3-hydroxy-4-methyl-phenylamino)-7-methoxy-quinoline-3-carbonitrile;

oo) 4-(4-chloro-2-fluoro-5-hydroxy-phenylamino)-7-methoxy-quinoline-3-carbonitrile;

pp) 4-(4-chloro-2-fluoro-phenylamino)-6-methoxy-quinoline-3-carbonitrile;

qq) 4-(3-hydroxy-4-methyl-phenylamino)-6-methoxy-quinoline-3-carbonitrile;

rr) 4-(4-chloro-2-fluoro-5-hydroxy-phenylamino)-6-methoxy-quinoline3-carbonitrile;

ss) 4-(3,5-dichloro-4-hydroxy-phenylamino)-6,7-dimethoxy-quinoline-3-carbonitrile;

tt) 4-(2-hydroxy-4-methyl-phenylamino)-6,7-dimethoxy-quinoline-3-carbonitrile;

uu) 4-(4-hydroxy-3,5-dimethyl-phenylamino)-6,7-dimethoxy-quinoline-3-carbinitile;

vv) 4-(5-chloro-2-hydroxy-phenylamino)-6,7-dimethoxy-quinoline-3-carbonitrile;

ww) 4-(3,5-dibromo-4-hydroxy-phenylamino)-6,7-dimethoxy-quinoline-3-carbonitrile;

xx) 4-(4-hydroxy-2-methyl-phenylamino)-6,7-dimethoxy-quinoline-3-carbonitrile;

yy) 6,7-dimethoxy-4-(pyridin-3-ylamino)-quinoline-3-carbonitrile; or zz) 6,7-dimethoxy-4-(3-methylsulfanyl-phenylamino)-quinoline-3-carbonitrile;

or a pharmaceutically acceptable salt thereof is provided.

20. The method according to claim I in which a) 4-(2-hydroxy-5-methyl-phenylamino)-6,7-dimethoxy-quinoline-3-carbonitrile;

b) 4-(2-chloro-4-hydroxy-phenylamino)-6,7-dimethoxy-quinoline-3-carbonitrile;

c) 6,7-dimethoxy-4-(4-methylsulfanyl-phenylamino)-quinoline-3-carbonitrile;

d) 4-[4-(2-hydroxy-ethyl)-phenylamino]-6,7-dimethoxy-quinoline-3-carbonitrile;

e) 4-(2,4-dihydroxy-phenylamino)-6,7-dimethoxy-quinoline-3-carbonitrile;
f) 4-[2-(2-hydroxy-ethyl)-phenylamino]-6,7-dimethoxy-quinoline-3-carbonitrile;
g) 4-(3-bromophenylamino)-6,7-dihydroxy-3-quinolinecarbonitrile;
h) 4-(3-bromophenylamino)-6,7-di-n-propoxy-3-quinolinecarbonitrile;
I) 4-[(3-bromophenyl)-n-acetylamino]-6,7-dihydroxy-3-quinolinecarbonitrile;
j) 4-(3-bromophenylamino)-6,7-di-n-butoxy-3-quinolinecarbonitrile;
k) 4-(4-chloro-2-fluorophenylamino)-7-methoxy-3-quinolinecarbonitrile;
l) 4-(4-chloro-2-fluorophenylamino)-7-hydroxy-3-quinolinecarbonitrile;
m) 4-[(4-chloro-2-fluorophenylamino)-n-acetylamino]-7-hydroxy-3-quinolinecarbonitrile;
n) 4-(4-chloro-2-fluorophenylamino)-7-ethoxy-3-quinolinecarbonitrile;
o) 4-[(3-bromophenyl)amino]-6,7-bis(2-methoxyethoxy)-3-quinolinecarbonitrile;
p) 4-(2-aminphenylmethylamino)-6,7-diethoxy-3-quinolinecarbonitrile;
q) 4-(3,4-difluorophenylmethylamino)-6,7-diethoxy-3-quinolinecarbonitrile;
r) 4-methoxy-but-2-enoic acid [4-(3-bromo-phenylamino)quinazolin-6-yl]-amide;
s) 7-benzyloxy-4-(4-chloro-2-fluoro-phenylamino)-6-methoxy-quinoline-3-carbonitrile;
t) 4-(4-chloro-2-fluoro-5-hydroxy-phenylamino)-7-methoxy-6-(3-morpholin-4-yl)-propoxyl-quinoline-3-carbonitrile;
u) N-[4-(3-bromo-phenylamino)-3-cyano-quinolin-6-yl]-3-chloro-(e) acrylamide;
v) N-[4-(3-bromo-phenylamino)-3-cyano-quinolin-6-yl]-3-chloro-(z)-acrylamide;
w) N-[4-[(3-bromophenyl)amino]-3-cyano-6-quinolinyl]-4-morpholino-2-butynamide;
x) N-[4-[(3-bromophenyl)amino]-3-cyano-6-quinolinyl]-4-dimethylamino-2-butynamide;
y) N-[4-[(3-bromophenyl)amino]-3-cyano-6-quinolinyl]-4-t-butyldimethylsiloxy-2-butynamide;
z) N-[4-[(3-bromophenyl)amino]-3-cyano-6-quinolinyl]-4-hydroxy-2-butynamide;
aa) 4-(3-hydroxymethyl-2-methylphenylamino)-6,7-dimethoxyquinoline-3-carbonitrile;
bb) 4-(2-amino-4,5-dimethylphenylamino)-6,7-dimethoxyquinoline-3-carbonitrile;
cc) 4-(4-ethylphenylamino)-6,7-dimethoxyquinoline-3-carbonitrile;
dd) 4-(4-chloro-2-methylphenylamino)-6,7-dimethoxyquinoline-3-carbonitrile;
ee) 6,7-dimethoxy-4-(3-phenoxyphenylamino)quinoline-3-carbonitrile;
ff) 4-(4-chloro-3-trifluoromethylphenylamino)-6,7-dimethoxyquinoline-3-carbonitrile;
gg) 4-(3-hydroxy-phenylamino)-6,7-dimethoxy-quinoline-3-carbonitrile;
hh) 4-(4-methyl-phenylamino)-6,7-dimethoxy-quinoline-3-carbonitrile;
ii) 4-(3-hydroxy-4-methyl-phenylamino)-8-methoxy-6-nitro-quinoline-3-carbonitrile;
jj) 4-(4-chloro-2-fluoro-phenylamino)-8-methoxy-6-nitro-quinoline-3-carbonitrile;
kk) 4-(3-hydroxy-4-methoxy-phenylamino)-8-methoxy-6-nitro-quinoline-3-carbonitrile;
ll) 6-amino-4-(3-hydroxy-4-methyl-phenylamino)-8-methoxy-quinoline-3-carbonitrile;
mm) 6-amino-4-(3-hydroxy-4-methoxy-phenylamino)-8-methoxy-quinoline-3-carbonitrile;
nn) N-{4-[(3-bromo-4-fluorophenyl)amino]-3-cyano-7-methoxy-6-quinolinyl}-4-bromo-2-butenamide;
oo) N-{4-[(3-bromophenyl)amino]-3-cyano-7-methoxy-6-quinolinyl}-4-chloro-2-butenamide;
pp) N-{3-cyano-4-[(3-iodophenyl)amino]-6-quinolinyl}-2-butynamide;
qq) N-{3-cyano-4-[(3-methylphenyl)amino]-6-quinolinyl}-2-propenamide;
rr) N-{4-[(4-bromophenyl)amino]-3-cyano-6-quinolinyl}-2-butynamide;
ss) N-{4-[(3-chloro-4-thiophenoxyphenyl)amino]-3-cyano-6-quinolinyl}-2-propenamide;
tt) N-{3-cyano-4-[(3,4-difluorophenyl)amino]-6-quinolinyl}-2-butynamide;
uu) N-{4-[(3-chlorophenyl)amino]-3-cyano-6-quinolinyl}-2-butynamide;
vv) N-{3-cyano-4-[(3-isopropylphenyl)amino]-6-quinolinyl}-2-butynamide;
ww) N-{3-cyano-4-[(3-isopropylphenyl)amino]-6-quinolinyl}-2-propenamide;
xx) 6-amino-4-[(3-isopropylphenyl)amino]-3-quinolinecarbonitrile;
yy) 4-[(3-isopropylphenyl)amino]-6-nitro-3-quinolinecarbonitrile; or
zz) 4-(3-bromo-phenylamino)-6-(3-pyrrolidin-1-yl-propylamino)quinoline-3-carbonitrile;
or a pharmaceutically acceptable salt thereof.
21. The method according to claim 1 in which
a) 4-(3-azido-phenylamino)-6,7-dimethoxy-quinoline-3-carbonitrile;
b) 6-amino-4-[(4-chloro-2-fluorophenyl)amino]-7-methoxy-3-quinolinecarbonitrile;
c) 4-[(4-chloro-2-fluorophenyl)amino]-7-methoxy-6-nitro-3-quinolinecarbonitrile;
d) 4-[(3,4-dichlorophenyl)amino]-6-nitro-3-quinolinecarbonitrile;
e) 6-amino-4-[(3-methylsulfanylphenyl)amino]-3-quinolinecarbonitrile;
f) 4-[(3-methylsulfanylphenyl)amino]-6-nitro-3-quinolinecarbonitrile;
g) 4-[(3-trifluoromethoxyphenyl)amino]-6-nitro-3-quinolinecarbonitrile;
h) 4-(3-dimethylamino-phenylamino)-6,7-dimethoxy-quinoline-3-carbonitrile;
I) 6,7-dimethoxy-4-(4-methoxy -2-methyl-phenylamino)-quinoline-3-carbonitrile;
j) 4-(3-hydroxy-4-methoxy-phenylamino)-6,7-dimethoxy-quinoline-3-carbonitrile;
k) 4-(3-chloro4-methyl-phenylamino)-6,7-dimethoxy-quinoline-3-carbonitrile;
l) 6,7-dimethoxy-4-(4-phenoxy-phenylamino)-quinoline-3-carbonitrile;
m) 4-(5-chloro-2-methoxy-phenylamino)-6,7-dimethoxy-quinoline-3-carbonitrile;

n) 3-(3-cyano-6,7-dimethoxy-quinolin-4-ylamino)-2-methyl-benzoic acid;

o) 4-(4-chloro-2-fluoro-phenylamino)-6,7-dihydroxy-quinoline-3-carbonitrile;

p) 4-(3-hydroxy-2-methyl-phenylamino)-6,7-dimethoxy-quinoline-3-carbonitrile;

q) 4-(3-chloro-4-methoxy-phenylamino)-6,7-dimethoxy-quinoline-3-carbonitrile;

r) 6,7-dimethoxy-4-(4-trifluoromethyl-phenylamino)-quinoline-3-carbonitrile;

s) 4-(3,4-dibromophenylamino)-6-nitroquinoline-3-carbonitrile;

t) 6-amino-4-(3-trifluoromethylphenylamino)quinoline-3-carbonitrile;

u) 6-amino-4-(3,4-dibromophenylamino)quinoline-3-carbonitrile;

v) N-[3-cyano-4-(3,4-dibromophenylamino)quinolin-6-yl]acrylamide;

w) N-[4-(3-bromophenylamino)-3-cyanoquinolin-6-yl]propionamide;

x) (e)-but-2-enoic acid [4-(3-bromophenylamino)-3-cyanoquinolin-6-yl]amide;

y) N-[4-(3-bromophenylamino)-3-cyanoquinolin-6-yl]-2-methylacrylamide;

z) 4-(3-fluorophenylamino)-6-nitroquinoline-3-carbonitrile;

aa) 6-amino-4-(3-fluorophenylamino)quinoline-3-carbonitrile;

bb) 4-(3-dimethylaminophenylamino)-6-nitroquinoline-3-carbonitrile;

cc) 4-(4-dimethylaminophenylamino)-6-nitroquinoline-3-carbonitrile;

dd) 6-amino-4-(3-dimethylaminophenylamino)quinoline-3-carbonitrile;

ee) 6-amino-4-(4-dimethylaminophenylamino)quinoline-3-carbonitrile;

ff) but-2-ynoic acid [4-(3-fluorophenylamino)-3-cyanoquinolin-6-yl]amide;

gg) N-[3-cyano-4-(3-dimethylaminophenylamino)quinolin-6-yl]acrylamide;

hh) N-[3-cyano-4-(4-Dimethylaminophenylamino)quinolin-6-yl]acrylamide;

ii) but-2-ynoic acid [3-cyano-4-(3-dimethylaminophenylamino)quinolin-6-yl]amide;

jj) but-2-ynoic acid [3-cyano-4-(4-dimethylaminophenylamino)quinolin-6-yl]amide;

kk) 4-(3-bromophenylamino)-6-dimethylaminoquinoline-3-carbonitrile hydrochloride;

ll) 6-dimethylamino-4-(3-methoxyphenylamino)quinoline-3-carbonitrile hydrochloride;

mm) 2-bromo-n-[4-(3-bromophenylamino)-3-cyanoquinolin-6-yl]acetamide;

nn) 6-iodo-4-(3-methoxyphenylamino)quinoline-3-carbonitrile;

oo) 4-(4-hydroxy-2-methyl-phenylamino)-6-methoxy-7-(3-morpholin-4-yl-propoxy)-quinoline-3-carbonitrile;

pp) 4-(3-bromo-phenylamino)-6-methoxy-7-(3-morpholin-4-yl-propoxy)-quinoline-3-carbonitrile;

qq) 6-methoxy-4-(2-methylsulfanyl-phenylamino)-7-(3-morpholin-4-yl-propoxy)-quinoline-3-carbonitrile; or rr) 4-(4-hydroxy-3,5-dimethyl-phenylamino)-6-methoxy-7-(3-morpholin-4-yl-propoxy)-quinoline-3-carbonitrile;

or a pharmaceutically acceptable salt thereof is provided.

\* \* \* \* \*